(12) United States Patent
Wels et al.

(10) Patent No.: US 12,023,353 B2
(45) Date of Patent: Jul. 2, 2024

(54) METHODS AND COMPOUNDS FOR IMPROVED IMMUNE CELL THERAPY

(71) Applicant: Chemotherapeutisches Forschungsinstitut Georg-Speyer-Haus, Frankfurt am Main (DE)

(72) Inventors: Winfried Wels, Frankfurt (DE); Anja Waldmann, Offenbach (DE); Congcong Zhang, Frankfurt (DE); Manuel Kaulich, Frankfurt am Main (DE)

(73) Assignee: Chemotherapeutisches Forschungsinstitut Georg-Speyer-Haus, Frankfurt am Main (DE)

( * ) Notice: Subject to any disclaimer, the term of this patent is extended or adjusted under 35 U.S.C. 154(b) by 739 days.

(21) Appl. No.: 16/757,198

(22) PCT Filed: Oct. 18, 2018

(86) PCT No.: PCT/EP2018/078539
§ 371 (c)(1),
(2) Date: Apr. 17, 2020

(87) PCT Pub. No.: WO2019/077037
PCT Pub. Date: Apr. 25, 2019

(65) Prior Publication Data
US 2021/0128615 A1 May 6, 2021

(30) Foreign Application Priority Data
Oct. 18, 2017 (EP) .................................. 17197125

(51) Int. Cl.
*A61K 35/17* (2015.01)
*C07K 16/24* (2006.01)
*C12N 5/0783* (2010.01)
*C12N 15/11* (2006.01)
*C12N 15/113* (2010.01)

(52) U.S. Cl.
CPC ............ *A61K 35/17* (2013.01); *C07K 16/244* (2013.01); *C07K 16/248* (2013.01); *C12N 5/0646* (2013.01); *C12N 15/11* (2013.01); *C12N 15/1136* (2013.01); *C07K 2317/76* (2013.01); *C12N 2310/14* (2013.01); *C12N 2310/20* (2017.05); *C12N 2501/2312* (2013.01); *C12N 2501/2315* (2013.01)

(58) Field of Classification Search
CPC .. A61K 35/17; A61K 39/0011; C07K 16/244; C07K 16/248; C12N 5/0646; C12N 15/11; C12N 15/1136
USPC ......................................... 435/455, 326, 328
See application file for complete search history.

(56) References Cited

U.S. PATENT DOCUMENTS

| | | |
|---|---|---|
| 2010/0015161 A1 | 1/2010 | Winqvist et al. |
| 2011/0150832 A1 | 6/2011 | Nemunaitis et al. |
| 2019/0038671 A1 * | 2/2019 | Fan .................... C07K 16/2818 |

FOREIGN PATENT DOCUMENTS

| | | | | |
|---|---|---|---|---|
| EP | 3184548 A1 * | 6/2017 | ....... | A61K 39/00117 |
| WO | 2016/126213 A1 | 8/2016 | | |
| WO | WO-2016126213 A1 * | 8/2016 | ............. | A61K 35/15 |
| WO | 2017/001572 A1 | 1/2017 | | |

OTHER PUBLICATIONS

Sandeep Nayar et al., "Extending the lifespan and efficacies of immune cells used in adoptive transfer for cancer immunotherapies—A review", ONCOIMMUNOLOGY, vol. 4, No. 4, p. e1002720 (11 pages), XP055435793, Mar. 19, 2015.
Zhang et al., "Interleukin-10: An Immune-Activating Cytokine in Cancer Immunotherapy", Journal of Clinical Oncology, vol. 34, No. 29, pp. 3576-3578, XP055436182, Oct. 10, 2016.
International Search Report and Written Opinion, International Patent Application No. PCT/EP2018/078539, dated Jun. 12, 2018 (16 pages).

* cited by examiner

*Primary Examiner* — Anne Marie S Wehbe
*Assistant Examiner* — Hanan Isam Abuzeineh
(74) *Attorney, Agent, or Firm* — Merchant & Gould P.C.

(57) ABSTRACT

The present invention pertains to methods and compounds useful in a therapy involving the administration of immune cells to a patient. The method of the invention involves the modification of cells of the immune system with agonists or antagonists of immune regulators such as Interleukin-10 (IL-10) or IL-6, in order to enhance and improve the immunological potential of the immune cells for therapy. Cells modified according to the method of the invention can be administered to a patient to support a treatment of proliferative diseases such as cancer or autoimmune disorders.

10 Claims, 13 Drawing Sheets

Figure 1:
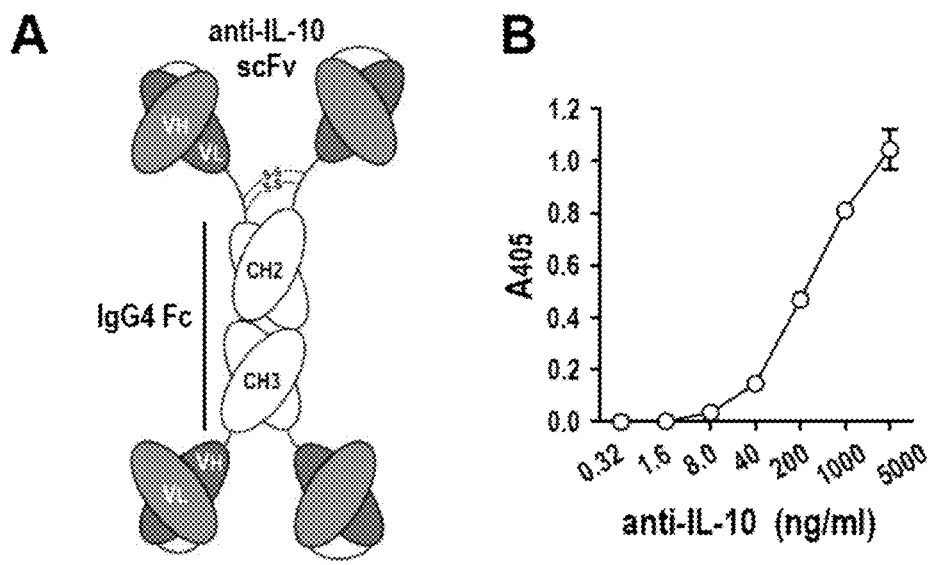
Figure 1:
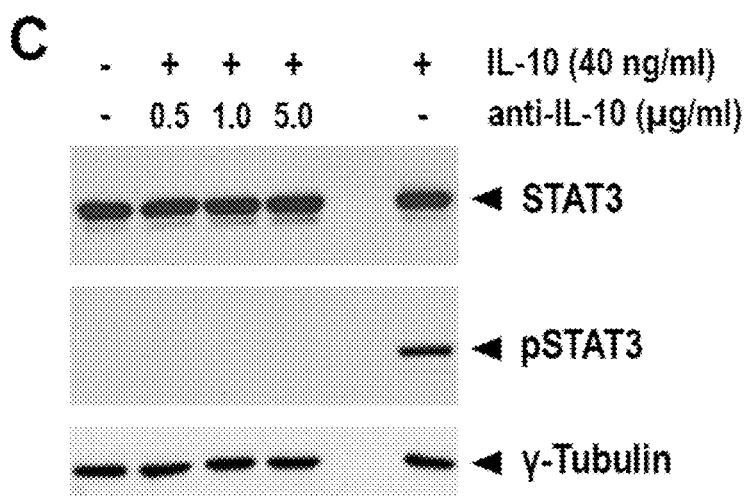
Figure 1:
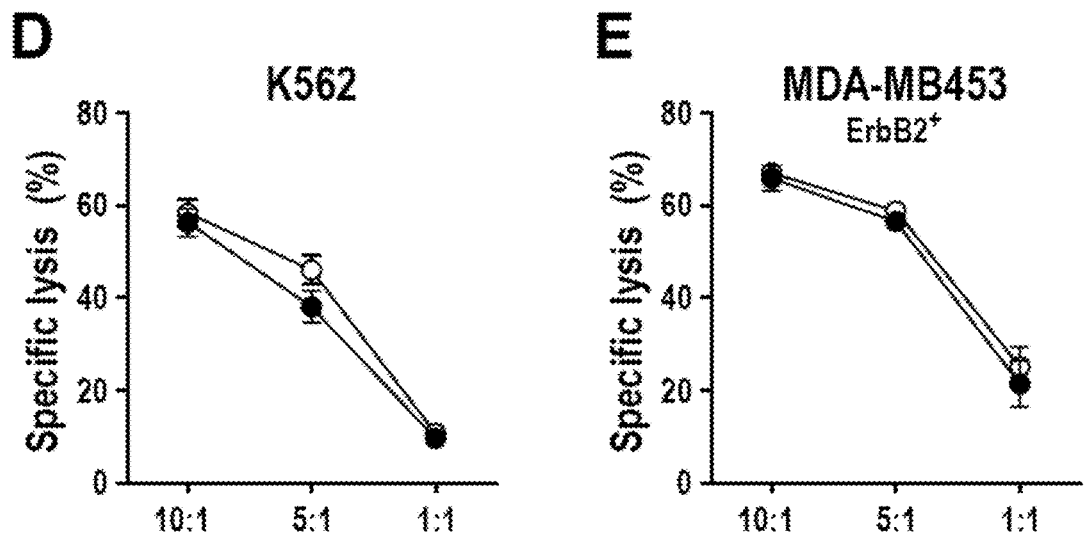

Specification includes a Sequence Listing.

A

B NK cells

C CAR NK cells

D Monocytes / macrophages

METHODS AND COMPOUNDS FOR IMPROVED IMMUNE CELL THERAPY

FIELD OF THE INVENTION

The present invention pertains to methods and compounds useful in a therapy involving the administration of immune cells to a patient. The method of the invention involves the modification of cells of the immune system with agonists or antagonists of immune regulators such as Interleukin-10 (IL-10) or IL-6, in order to enhance and improve the immunological potential of the immune cells for therapy. Cells modified according to the method of the invention can be administered to a patient to support a treatment of proliferative diseases such as cancer or autoimmune disorders. Particular embodiments of the invention provide a combination of IL-10 antagonists with agonists of the pro-inflammatory cytokines IL-15 and IL-12 in immune effector cells such as genetically engineered T cells or natural killer cells, or others.

DESCRIPTION

Natural killer (NK) cells and T cells are important cell types for the development of adoptive cancer immunotherapies. During the past decades different approaches were developed to enhance potency and antitumour activity of these effector lymphocytes. Before infusion into patients, T cells, tumour-infiltrating lymphocytes (TILs) and NK cells can be activated and expanded ex vivo through stimulation with soluble cytokines such as interleukin (IL)-2 or IL-15, or by exposure to feeder cells that express membrane-anchored cytokines and stimulatory ligands. Also monoclonal antibodies specific for tumour-associated antigens, bispecific T-cell engagers (BiTEs), bi- and trispecific killer cell engagers (BiKEs, TriKEs) and immune checkpoint inhibitors can increase antitumour activity of NK and T cells. Genetic modification of effector lymphocytes constitutes another approach to enhance their activity, and remarkable progress has been made in the clinical development of T cells engineered to express T-cell receptors (TCRs) or chimeric antigen receptors (CARs) with defined tumour cell specificity. Likewise, NK cells can be genetically modified to express CARs that mediate specific recognition and lysis of cancer cells, thereby overcoming endogenous resistance mechanisms in tumour cells.

In addition to direct killing of tumour cells, lymphocytes like NK cells and T cells can contribute to tumour control by recruitment of and cross-talk with other immune cells, to a large part mediated by the secretion of cytokines and chemokines. Hence, in addition to direct antitumour effects, adoptive transfer of NK cells and T cells can result in the induction of protective endogenous antitumour immunity as demonstrated in immunocompetent mouse models. This implies that NK and T cells could be employed as on-site tumour vaccination agents, which release a broad spectrum of tumour antigens by tumour cell lysis for uptake and presentation by antigen presenting cells (APCs). Improved antigen presentation is also intended by adoptive cell therapy with myeloid cells like macrophages and dendritic cells (DCs). However, together with pro-inflammatory factors such as interferon (IFN)-γ, adoptively transferred immune effector cells may also secrete immunoregulatory molecules like IL-10, which can downmodulate the activity of bystander immune cells thereby limiting therapeutic efficacy.

IL-10 is an immunomodulatory cytokine with a pleiotropic role in the regulation of the immune response. It was first discovered as cytokine synthesis inhibitory factor (CSIF) in Th2 T cells. Subsequently, IL-10 expression was also found in many different immune cells, including CD4+ and CD8+ T cells, NK cells, monocytes/macrophages, and activated B cells. High expression of IL-10 has been observed in cytokine-activated NK cells as well as in CAR-engineered NK cells. Serum analysis also demonstrated a marked increase in IL-10 concentration in the blood of patients treated with CAR T cells. Although IL-10 was shown to directly stimulate cytotoxic CD8+ T cells, it also promotes the development of regulatory T (Treg) cells and contributes to the shift towards a Th2 type T-cell response. This can in turn downmodulate antitumour activity of effector T cells. Indeed, enhanced IL-10 expression was reported in different human tumours, and elevated levels of circulating IL-10 were correlated with poor prognosis for patients with hematological and solid cancers. Furthermore, susceptibility to prostate, breast, cervical and gastric cancers has been associated with IL-10 promoter polymorphisms and increased IL-10 production.

It is generally accepted that IL-10 dampens adaptive immunity mainly through the direct suppression of the activity of APCs, including both dendritic cells and macrophages. IL-10 blocks MyD88-dependent toll-like receptor (TLR) signaling, prevents the differentiation of monocytes into DCs, and inhibits the maturation of DCs leading to the downregulation of IFN-γ-induced MHC II and costimulatory molecules like CD80 and CD86. Autocrine production of IL-10 also suppressed DC migration to draining lymph nodes. Conversely, inhibition of IL-10 with a neutralizing antibody restored the capacity of DCs to activate T cells. IL10 can further impair the formation of peptide-MHC II complexes in macrophages, suppressing cell-mediated antigen presentation. In addition, IL-10 inhibits the production of pro-inflammatory cytokines like IL-1β, IL-12, G-CSF, GM-CSF and TNF-α in bystander immune cells. Of note, also the bidirectional NK-DC crosstalk through IFN-γ, IL-12 and TNF-α to enhance T-cell priming can be significantly diminished by IL-10. Similar to IL-10, also IL-6 has multiple immunoregulatory activities.

It was therefore an object of the present invention to provide novel approaches to increase the therapeutic potential of immune cells, preferably for use in the context of adoptive immune cell transfer, for example, in the treatment of cancer.

The above problem is solved in a first aspect by a method for enhancing the immunological activity of a target immune effector cell, the method comprising the steps of:
 (a) Providing a target immune effector cell,
 (b) Inhibiting in said target immune effector cell the expression, function, stability or secretion of one or more endogenous regulators of immunity of said target immune effector cell.

In some embodiments the above method is used for the production of an immune effector cell with enhanced immunological activity. In these aspects and embodiments, the method may comprise an additional step (c) subsequent to step (b): harvesting said target immune effector cells. Prior to step (c), the method optionally may include a step (b') comprising culturing said immune effector cells for an amount of time sufficient for the manifestation of the enhanced immunological activity in said cells.

In some preferred embodiments of the invention "enhancing" shall be understood to be increasing or enhancing the immunological activity of a target immune cell. An immunological activity is preferably the potential of a target immune cell to immunologically identify and/or to kill a target cell afflicted with a disease such as an infected cell or a tumour cell and/or to enhance antigen presentation and antitumour activity of bystander immune cells.

In the context of the herein disclosed invention the term "endogenous regulators of immunity of said target immune effector cell" are preferably proteins selected from the group consisting of IL-1, IL-4, IL-6, IL-10, IL-17, transforming growth factor (TGF)-β, CCL-2/MCP-1, CCL-5/RANTES, indoleamine 2,3-deoxygenase (IDO), vascular endothelial growth factor (VEGF), galectins, fibrinogen-like protein 2 (FGL2), CTLA-4, and/or PD-1, or any combination of these regulators. In preferred embodiments the endogenous regulator of immunity of said target immune effector cell is IL-10 or is IL-6.

In some embodiments the "endogenous regulator of immunity" is an endogenously expressed regulator of immunity. In preferred embodiments step (b) of inhibiting in said target immune effector cell the expression, function, stability or secretion of one or more endogenous regulators of immunity of said target immune effector cell, pertains to an alteration performed within the target immune effector cell which has the effect of inhibiting the expression, function, stability or secretion of one or more endogenous regulators of immunity within the very same cell to which the alteration was performed. The term "same cell" in this specific context is not meant to refer to the same cell type, but to the same cellular entity. Therefore "inhibiting" in this specific embodiment is not dependent on cell-to-cell communication such as cell-to-cell binding or secretion of molecules. Such endogenously expressed regulators of immunity are preferably proteins which are either secreted (and therefore are soluble proteins) or are membrane-bound proteins such as membrane-anchored proteins. In some embodiments the endogenously expressed regulator of immunity is a cytokine or chemokine, preferably an extracellular secreted or extracellular membrane bound cytokine or chemokine, most preferably selected from IL-1, IL-4, IL-6, IL-10, IL-17, TGF-β, CCL-2/MCP-1, and CCL-5/RANTES; and preferably is IL-10, IL-6 and/or IL4.

In some other preferred embodiments of the invention the endogenously expressed regulator of immunity is not a component of the cellular Major Histocompatibility Complex (MHC) or T-cell receptor (TCR) complex. In particular, in this embodiment the endogenously expressed regulator of immunity is not HLA or CD3, and also not another protein involved in T-cell interactions such as CD7.

In other embodiments the "endogenous regulators of immunity of said target immune effector cell" are proteins or cellular factors which are known to act as a negative regulator of the immune function of the target immune cell. The invention hence suggests using in this context an inhibitor of such a negative regulator, and/or inhibiting by any other means such a negative regulator in the target immune cell, in order to enhance the immunological activity of a target immune effector cell for the herein disclosed therapeutic purposes.

In one additional embodiment the method of the invention may further comprise an additional step of bringing into contact the target immune effector cell with an activator or agonist of immune function of the target immune cell. Preferred activators or agonists of the invention are selected from pro-inflammatory cytokines. The term "pro-inflammatory cytokine" shall pertain to immunoregulatory cytokines which favour inflammation. Typically, pro-inflammatory cytokines comprise IL-2, LIF, IFN-γ, IFN-α, OSM, CNTF, GM-CSF, TWEAK, IL-11, IL-12, single-chain IL-12, IL-15, IL-15 hyper-agonist, IL-18, IL-19, IL-20, IL21, IL-8, IL-16, IL-22, IL-23, IL-31, IL-32, GM-CSF, and TNF-α; preferred pro-inflammatory cytokines of the invention are selected from IL-2, IL-12, single-chain IL-12, IL-15, IL-15 hyper-agonist, IL-18, IL-21, GM-CSF, TNF-α, or endoplasmic reticulum (ER)-retained or membrane anchored variants thereof, or any combination of these compounds, and in particular are single chain IL-12 and IL-15 hyper-agonist.

In particular embodiments of the invention the method involves the co-expression of such an activator and/or agonist of immune function, and which preferably is an agonist of IL-12 and/or IL-15, and preferably is selected from IL-15 hyper-agonist or single-chain IL-12. It is in this embodiment preferred that the method of the invention involves a co-expression in said target immune effector cell of an anti-IL-10 antibody (or a molecule comprising an antigen-binding fragment of an anti-IL-10 antibody) together with either an agonist and/or activator of IL-15 or an agonist and/or activator of IL-12, preferably of IL-15 hyper-agonist or single-chain IL-12. This embodiment is particularly useful to target immune effector cells which do not endogenously express, or do not endogenously express sufficient amounts of, IL-12 and/or IL-15 respectively.

In the context of the invention, in some preferred embodiments, said activator or agonist of immune function of the target immune effector cell is not an endogenous regulator of immune function of said target cell.

In some embodiments the activator or agonist of immune function is brought into contact with the target immune effector cell by expression of said activator or agonist in said cell, for example by introducing into the cell an expression construct encoding any one or a combination of the above disclosed activators or agonists. Other embodiments pertain to the use of mRNA of such activator or agonists which is contacted with the cell in order to allow for protein translation of the activator or agonists by the target cell. Other embodiments pertain to the use of isolated protein of the activator or agonists which can be used directly to induce and enhance immune cell activity. In some preferred embodiments the expression and/or introduction of said activator or agonist of immune function of the target immune effector cell is introduced together with the inhibitor of the endogenous regulator of the target immune effector cell. Preferably, a pro-inflammatory cytokine may be expressed together with an antibody construct encoding an inhibitory antibody specific for said endogenous regulator of immunity of said target immune effector cell. Co-expression can be affected by two separate constructs or using one genetic construct as for example shown in the appended examples. Hence, preferred constructs include the single chain IL12 and IL-15 hyper-agonist constructs shown in SEQ ID NO: 9 to 12, which are fused to the IL-10 ER retained antibody construct of the invention. Similar constructs using the other disclosed antibodies and agonists of immune function of the target immune effector cell can be envisioned by the skilled artisan in view of the present disclosure.

In the context of the invention the term "target immune effector cell" is a cell having a function in the adaptive or innate immune response of a host to infections or cancer. The target immune effector cell may be any cell of the immune system such as but not limited to any of the following (or combinations of these): monocytic cell, macrophage, dendritic cell, B cell, T cell, such as a T helper cell, Th17 T cell, cytotoxic T cell, mast cell, NK cell or NKT cell, but is preferably selected from the group consisting of a monocytic cell, macrophage, dendritic cell, B cell, T cell, NK cell or NKT cell. In alternative or additional embodiments of the invention said target immune effector cell is a mammalian cell, preferably a human cell, more preferably a human cell obtained from a patient in need of an adoptive immune cell treatment.

In the method of the invention "inhibiting" in said target immune effector cell the expression, function, stability or secretion of one or more endogenous regulators of immunity of said target immune effector cell preferably comprises bringing into contact the target immune effector cell with an inhibitor of said negative regulator of immunity. Bringing into contact may involve simply admixing the cells with the inhibitor, or may involve the expression of the inhibitor in said cells, or alternatively transfection or transduction of said inhibitor into said cells.

Preferably, inhibiting in said target immune effector cell the expression, function, stability or secretion of one or more endogenous regulators of immunity of said target immune effector cell comprises introducing into the target immune effector cell a vector for expression of an inhibitor of said regulator of immunity.

Yet more preferably, inhibiting in said target immune effector cell the expression, function, stability or secretion of one or more endogenous regulators of immunity of said target immune effector cell involves (i) the use of an inhibitory antibody specific for said endogenous regulator of immunity, (ii) the use of an antisense nucleic acid construct targeting the expression of said endogenous regulator of immunity, or (iii) the use of a gene editing approach introducing a deleterious mutation into the gene sequence of said endogenous regulator of immunity.

In some embodiments of the invention modifying the immunological activity of a target immune effector cell involves any one of the following: (i) increased cytotoxicity of said target immune effector cell compared to a control, (ii) increased expression of pro-inflammatory cytokines, such as IL-1$\beta$, IL-12, G-CSF, GM-CSF and preferably TNF-$\alpha$, preferably in bystander immune cells, (iii) induction of a tumour suppressing macrophage M1 phenotype.

In the context of the herein disclosed aspects and embodiments of the invention said endogenous regulator of immunity is preferably IL-10 or IL-6. Hence, in these aspects and embodiments the inhibiting in said target immune effector cell the expression, function, stability or secretion of one or more endogenous regulators of immunity of said target immune effector cell involves the use of an inhibitor of IL-10 or IL-6.

As used herein, the term "IL-10 inhibitor" means a substance that affects a decrease in the amount or rate of IL-10 expression or activity. Such a substance can act directly, for example, by binding to IL-10 and decreasing the amount or rate of IL-10 expression or activity. An IL-10 inhibitor can also decrease the amount or rate of IL-10 expression or activity, for example, by binding to IL-10 in such a way as to reduce or prevent interaction of IL-10 with an IL-10 receptor; by binding to IL-10 and modifying it, such as by removal or addition of a moiety; and by binding to IL-10 and reducing its stability. An IL-10 inhibitor can also act indirectly, for example, by binding to a regulatory molecule or gene region so as to modulate regulatory protein or gene region function and affect a decrease in the amount or rate of IL-10 expression or activity. Thus, an IL-10 inhibitor can act by any mechanisms that result in a decrease in the amount or rate of IL-10 expression or activity.

An IL-10 inhibitor can be, for example, a naturally or non-naturally occurring macromolecule, such as a polypeptide, peptide, peptide-mimetic, nucleic acid, carbohydrate or lipid. An IL-10 inhibitor further can be an antibody, or antigen-binding fragment thereof, such as a monoclonal antibody, humanized antibody, chimeric antibody, miniantibody, nanobody, bifunctional antibody, single chain antibody (scFv), variable region fragment (Fv or Fd), Fab or F(ab)2. An IL-10 inhibitor can also be polyclonal antibodies specific for IL-10. An IL-10 inhibitor further can be a partially or completely synthetic derivative, analog or mimetic of a naturally occurring macromolecule, or a small organic or inorganic molecule.

An IL-10 inhibitor that is an antibody can be, for example, an antibody that binds to IL-10 and inhibits binding to an IL-10 receptor, or alters the activity of a molecule that regulates IL-10 expression or activity, such that the amount or rate of IL-10 expression or activity is decreased. An antibody useful in a method of the invention can be a naturally occurring antibody, including monoclonal or polyclonal antibodies or fragments thereof, or a non-naturally occurring antibody, including but not limited to a single chain antibody, mini-antibody, nanobody, chimeric antibody, bi-functional antibody, complementarity determining region-grafted (CDR-grafted) antibody and humanized antibody or an antigen-binding fragment thereof.

An IL-10 inhibitor that is a nucleic acid can be, for example, an anti-sense nucleotide sequence, an RNA molecule, or an aptamer sequence. An anti-sense nucleotide sequence can bind to a nucleotide sequence within a cell and modulate the level of expression of IL-10, IL-10 receptor or modulate expression of another gene that controls the expression or activity of IL-10. Similarly, an RNA molecule, such as a catalytic ribozyme, can cleave a specific mRNA and alter the expression of the IL-10 gene, or another gene that controls the expression or activity of IL-10. An aptamer is a nucleic acid sequence that has a three dimensional structure capable of binding to a molecular target.

An IL-10 inhibitor that is a nucleic acid also can be a double-stranded RNA molecule for use in RNA interference methods. RNA interference (RNAi) is a process of sequence-specific gene silencing by post-transcriptional RNA degradation, which is initiated by double-stranded RNA (dsRNA) homologous in sequence to the silenced gene. A suitable double-stranded RNA (dsRNA) for RNAi contains sense and antisense strands of about 21 contiguous nucleotides corresponding to the gene to be targeted that form 19 RNA base pairs, leaving overhangs of two nucleotides at each 3' end. dsRNAs of about 25-30 nucleotides have also been used successfully for RNAi. dsRNA can be synthesized in vitro and introduced into a cell by methods known in the art.

It is preferred that inhibiting in said target immune effector cell the expression, function, stability or secretion of one or more endogenous regulators of immunity of said target immune effector cell involves bringing into contact said target immune effector cell with an IL-10 antibody, preferably wherein the IL-10 antibody binds and thereby inactivates IL-10.

In some preferred embodiments of the invention, the IL-10 inhibitor is an anti-IL-10 antibody. An IL-10 antibody according to the invention is preferably (i) added to said target immune effector cell as a protein preparation, or more preferably (ii) is expressed as a genetic construct in said cell, for example wherein the genetic construct encodes a secreted antibody, or a membrane associated antibody, or an endoplasmic reticulum (ER)-located antibody. Such methods for the cellular expression of antibody constructs which are targeted to cellular compartments or are indicated for antibody secretion are well known to the skilled artisan.

It shall be understood that the above said with regard to IL-10 inhibitors equally applies to any other herein disclosed or suggested inhibitor of a regulator of target immune cell function in accordance with the present invention. In particular the above said with regard to IL-10 equally applies to IL-6 inhibitors. The amino acid sequence of IL-10 (UniProt accession number P22301) is provided herein in SEQ ID NO: 28. The amino acid sequence of IL6 (UniProt accession number P05231) is provided in SEQ ID NO: 29. The amino acid sequences of other preferred endogenous immune regulators can be derived from public databases such as UniProt (www.uniprot.org) which can be reached for example via the mentioned gene names according to the HGNC Database of October 2017, HUGO Gene Nomenclature Committee (HGNC), EMBL Outstation—Hinxton, European Bioinformatics Institute, Wellcome Trust Genome Campus, Hinxton, Cambridgeshire, CB10 1SD, UK (https://www.genenames.org; Gray K A, Yates B, Seal R L, Wright M W, Bruford E A. gene-names.org: the HGNC resources in 2015. Nucleic Acids Res. 2015 January; 43 (Database issue):D1079-85. doi: 10.1093/nar/gku1071. PMID:25361968).

In alternative or additional embodiments said IL-10 antibody comprises one or more variable light chain sequences and variable heavy chain sequences of the BT-063 antibody as disclosed in PCT/EP2010/068569, and preferably is a homodimer of two antibody chains each comprising two scFv fragments of BT-063 (tetravalent anti-IL-10 antibody). Other antibodies useful for inhibiting IL-10 are the anti-IL-10 antibodies disclosed in U.S. Pat. No. 7,662,379 B2 (incorporated herein by reference).

In other preferred embodiments said IL-10 antibody comprises at least one anti-IL-10 single chain antibody, wherein the single chain antibody comprises one variable heavy chain sequence and one variable light chain sequence of the anti-IL-10 antibody, connected by a linker peptide. In certain embodiments, the linker peptide is a glycine-serine linker. In further embodiments, the linker peptide comprises or consists of the sequence of glycine and serine, e.g., (GGGGS)$_n$, wherein n is an integer from 1 to 5, such as 1, 2, 3, 4, 5. Other linker peptides used for the design of single chain constructs are well known in the art. In further embodiments, the anti-IL-10 single chain antibody further comprises an endoplasmic reticulum retention sequence located at the carboxyterminus of the anti-IL-10 single chain antibody, comprising or consisting of the sequence lysine-aspartic acid-glutamic acid-leucine (KDEL). In other embodiments, the anti-IL-10 single chain antibody further comprises a transmembrane domain located at the carboxyterminus of the anti-IL-10 single chain Fv antibody. In further embodiments, the anti-IL-10 single chain Fv antibody further comprises a spacer sequence such as a hinge sequence located between the anti-IL-10 single chain Fv antibody and the transmembrane domain.

It shall be understood that the above said with regard to IL-10 inhibitors derived from antibody BT-063 equally applies to IL-10 inhibitors derived from other anti-IL-10 antibodies which like BT-063 block the interaction of IL-10 with IL-10 receptors, including but not limited to the anti-IL-10 antibodies disclosed in U.S. Pat. No. 7,662,379 B2, or anti-IL-10 antibodies generated by immunization of a mammal with IL-10 or isolated from random antibody libraries using IL-10, following procedures well known to the skilled artisan.

Preferred inhibitors of IL-10 according to the invention are any of the herein disclosed antibody constructs, as well as antigen binding fragments or derivatives thereof, or antisense compounds. The invention shall therefore in preferred embodiments pertain to an antibody, or antibody-like compound, derived from or similar to an antibody encoded by a nucleic acid which is at least 80%, preferably 90%, most preferably 95% (or 99%) identical to a sequence shown in SEQ ID No: 1, 3, 5, 7, 9, or 11. Alternatively, the invention shall pertain to an antibody, or antibody-like compound, derived from or similar to an antibody having an amino acid sequence which is at least 80%, preferably 90%, most preferably 95% (or 99%) identical to a sequence shown in SEQ ID No: 2, 4, 6, 8, 10 or 12. Preferably, the sequence identity is in some embodiments calculated based on the variable domain sequences of the antibody constructs of the examples (table 1). Most preferably, the antibodies encompassed by the present invention are those who have complementarity determining regions (CDR) 1 to 3 identical to the CDRs shown in any of the enclosed IL-10 antibody sequences (SEQ ID NO: 1 to 12). In some embodiments antibodies, or antibody-like compounds, are preferred which have in their CDR sequences not more than 3, preferably not more than 2, most preferably only 1, amino acid exchange, addition or deletion compared to the CDR sequences of any of the antibodies shown in SEQ ID Nos: 1 to 12.

In additional embodiments said inhibitor of an endogenous regulator of immunity of said target immune effector cell comprises at least one anti-IL-6 single chain antibody, wherein the single chain antibody comprises one variable heavy chain sequence and one variable light chain sequence of the humanized anti-IL-6 antibody olokizumab as disclosed in Shaw et al. mAbs 6: 774-782, 2014, connected by a linker peptide. In further embodiments, the anti-IL-6 single chain antibody further comprises an endoplasmic reticulum retention sequence located at the carboxyterminus of the anti-IL-6 single chain antibody, comprising or consisting of the sequence lysine-aspartic acid-glutamic acid-leucine (KDEL). In other embodiments, the anti-IL-6 single chain antibody further comprises a transmembrane domain located at the carboxyterminus of the anti-IL-6 single chain Fv antibody. In further embodiments, the anti-IL-6 single chain Fv antibody further comprises a spacer sequence such as a hinge sequence located between the anti-IL-6 single chain Fv antibody and the transmembrane domain. Other antibodies useful for inhibiting IL-6 are the anti-IL-6 antibodies disclosed in U.S. Pat. No. 7,612,182 B2, WO2016160923 A1, U.S. Pat. No. 9,187,560 B2, EP2087005 B1 (incorporated herein by reference). It shall be understood that the above said with regard to IL-6 inhibitors derived from antibody olokizumab equally applies to IL-6 inhibitors derived from other anti-IL-6 antibodies which like okolizumab block the interaction of IL-6 with IL-6 receptors, including but not limited to the anti-IL-6 antibodies disclosed in U.S. Pat. No. 7,612,182 B2, WO2016160923 A1, U.S. Pat. No. 9,187,560 B2, EP2087005 B1, or anti-IL-6 antibodies generated by immunization of a mammal with IL-6 or isolated from random antibody libraries using IL6, following procedures well known to the skilled artisan.

Preferred inhibitors of IL-6 according to the invention are any of the herein disclosed antibody constructs or antisense compounds. The invention shall therefore in preferred embodiments pertain to an antibody, or antibody-like compound, derived from or similar to an antibody encoded by a nucleic acid which is at least 80%, preferably 90%, most preferably 95% (or 99%) identical to a sequence shown in SEQ ID No: 13, 15, or 17. Alternatively, the invention shall pertain to an antibody, or antibody-like compound, derived from or similar to an antibody having an amino acid sequence which is at least 80%, preferably 90%, most preferably 95% (or 99%) identical to a sequence shown in SEQ ID No: 14, 16 or 18. Preferably, the sequence identity is in some embodiments calculated based on the variable domain sequences of the antibody constructs of the examples (table 1). Most preferably, the antibodies encompassed by the present invention are those who have complementarity determining regions (CDR) 1 to 3 identical to the CDRs shown in any of the enclosed IL-6 antibody sequences (SEQ ID NO: 13 to 18). In some embodiments antibodies, or antibody-like compounds, are preferred which have in their CDR sequences not more than 3, preferably not more than 2, most preferably only 1, amino acid exchange, addition or deletion compared to the CDR sequences of any of the antibodies of SEQ ID Nos: 13 to 18.

The person of skill may use other prior art antibodies targeting immune cell regulators to construct similar inhibitory compounds as the herein disclosed constructs for IL-10 and IL6.

Preferred embodiments of the invention are inhibitors that are antibodies or antibody derived compounds, or alternatively T-cell receptor (TCR) derived binding constructs, or artificial antigen binding constructs such as designed ankyrin repeat proteins (DARPins) or engineered lipocalins (anticalins). The term antibody in the context of the invention may refer to any antigen binding protein which is derived from an antibody. Antibodies of the invention include any immunoglobulin molecule which specifically binds to an antigen. Antibodies can be intact immunoglobulins derived from natural sources or from recombinant sources and can be immunoreactive portions of intact immunoglobulins. Antibodies are typically dimers of immunoglobulin molecules. The antibodies in the present invention may exist in a variety of forms including, for example, polyclonal antibodies, monoclonal antibodies, Fv, Fab and F(ab)2, as well as single chain antibodies (scFv) and humanized antibodies (more information on antibody technologies may be obtained from ANTIBODIES: A LABORATORY MANUAL—SECOND EDITION, 2014 by Cold Spring Harbor Laboratory Press, Cold Spring Harbor, New York, incorporated herein by reference).

The invention shall also include the use of "antibody fragments", a term which refers to a portion of an intact antibody and refers to the antigen specificity determining variable regions of an intact antibody. Examples of antibody fragments include, but are not limited to, Fab, Fab', F(ab')2, and Fv fragments, linear antibodies, scFv antibodies, and multispecific antibodies formed from antibody fragments. Such fragments for example may be used in fusion proteins to obtain multivalent antibody constructs. The term "mini-antibody" (or minibody) refers to a single chain polypeptide that comprises a secretion signal, a variable heavy chain fragment, a variable light chain fragment and a constant chain fragment. After expression in a cell, the mini-antibody is secreted from the cell by virtue of the secretion signal.

Antisense inhibitors of other regulators of the invention, for example of IL-1, IL-4, IL-17, TGF-β, CCL-2/MCP-1, CCL-5/RANTES, indoleamine 2,3-deoxygenase (IDO), vascular endothelial growth factor (VEGF), galectins, fibrinogen-like protein 2 (FGL2), CTLA-4, or PD1 can be easily designed according to their mRNA sequences or by using publically available siRNA resources such as the human siGENOME siRNA Library of Dharmacon® (see http://dharmacon.gelifesciences.com/). Similar libraries or design tools are available for shRNA or CRISPR/Cas9 mediated gene editing using guide nucleic acid sequences. All these approaches are based on the sequence complementarity of an antisense construct and the target mRNA or gene sequence.

Preferred antisense constructs of the invention are for example guideRNAs according to any one of SEQ ID Nos: 19 to 26, which are used for targeted IL-10 gene manipulation. The gRNA sequence in the sequence protocol is provided always as DNA sequence, but the skilled artisan knows that depending on the gene editing approach it may be used either as RNA or DNA molecules. Another preferred antisense construct of the invention is the shRNA sequence (mature sequence) provided in SEQ ID NO: 27.

Other inhibitors of the target regulators include for example for IL-1: the IL-1 receptor antagonist anakinra, the soluble decoy receptor rilonacept and the neutralizing monoclonal anti-IL-1β antibody canakinumab. For IL-4, for example, dupilumab is known, which is a fully human monoclonal antibody that binds to a subunit of the IL-4 receptor. For IL-17: the fully human monoclonal antibody secukinumab, a humanized IgG4 specific for IL-17 (ixekizumab) and a fully human antibody that targets the IL-17 receptor A (brodalumab); further IL-17 antibodies are also disclosed in WO 2007/149032 (included herein by reference). Inhibitory antibodies to TGF-β are for example disclosed in US20020176858 (included herein by reference). Methods for the inhibition of CCL-2 are for example reviewed and disclosed in Kirk P S, et al. "Inhibition of CCL2 Signaling in Combination with Docetaxel Treatment Has Profound Inhibitory Effects on Prostate Cancer Growth in Bone." International Journal of Molecular Sciences. 2013; 14(5):10483-10496. doi:m.3390/ijms140510483 (included herein by reference). CCl-2 inhibitors include neutralizing antibodies and peptides blocking receptor binding. Antibodies and siRNA inhibiting CCL-5 are for example disclosed in Kan Y J et al J Cell Physiol. 2015 August; 230(8):1883-94. doi: 10.1002/jcp.24918 (included herein by reference). Inhibitors of IDO include for example, but are not limited to, 1-methyl-tryptophan, β-(3 benzofuranyl)-alanine, β-[3-benzo(b)thienyl]-alanine, 6-nitro-tryptophan, and derivatives thereof. Further references and disclosure with regard to IDO inhibitors may be derived from US 2009/0155311 (included herein by reference). VEGF inhibitors are well known in the art, as an example the antibodies provided in any of the documents WO 98/35958, WO 00/09495, WO 00/27820, WO 00/59509, WO 98/11223, WO 00/27819, WO 01/55114, WO 01/58899 and EP 0 769 947 may be used. Antibodies against the proteins CTLA-4 and PD-1 are for example ipilimumab and nivolumab, respectively. A small molecular weight inhibitor of galectin-3 is for example known as 3,3'-dideoxy-3,3'-bis-[4-(3-fluorophenyl)-1H-1,2,3-triazol-1-yl]-1,1'-sulfanediyl-di-β-D-galactopyranoside (33DFTG, previously called TD139; Mackinnon A C, et al. "Regulation of transforming growth factor-beta1-driven lung fibrosis by galectin-3". Am J Respir Crit Care Med. 2012; 185: 537-546, incorporated herein by reference). An inhibitory antibody of FGL2 is for example used in Yan J, Kong L-Y, Hu J, et al. "FGL2 as a Multimodality Regulator of Tumor-Mediated Immune Suppression and Therapeutic Target in Gliomas." JNCI Journal of the National Cancer Institute. 2015; 107(8):djv137. doi:10.1093/jnci/djv137 (incorporated herein by reference).

In other preferred embodiments inhibiting in said target immune effector cell the expression, function, stability or secretion of one or more endogenous regulators of immunity of said target immune effector cell involves bringing into contact said target immune effector cell with an IL-10 inhibitor that is a nucleic acid, such as an anti-IL-10 antisense nucleic acid. Such a nucleic acid construct could involve expression of an anti-IL-10 shRNA in said target immune effector cell. Alternatively, the nucleic acid IL-10 inhibitor of the invention may be a nucleic acid construct suitable for targeted gene editing. This may involve bringing into contact said target immune effector cell with at least one gene editing nuclease, such as CAS9 and a guide nucleic acid, such as a guide RNA (gRNA), specific for IL-10. Here the gRNA or gDNA construct is the IL-10 inhibitor of the invention.

In some preferred embodiments the method of the invention is performed in vivo for example by administration of one or more compounds for inhibiting in said target immune effector cell in vivo the expression, function, stability or secretion of one or more endogenous regulators of immunity of said target immune effector cell. In alternative embodiments the method of the invention is performed in vitro or ex vivo. In these embodiments target immune cells are provided in cell culture and used in the method. In such embodiments the method of the invention may further comprise a subsequent step (c) culturing and/or expanding said target immune effector cells.

In another aspect of the invention a method for modifying an immune response in a subject is provided, the method comprising performing the method for enhancing the immunological activity of a target immune effector cell as described herein, and administering said treated target immune effector cells to the subject. The method is usually applied when treating a disorder in the subject. Further, the method may optionally comprise prior to step (a) a step of obtaining a biological sample of the subject and isolating therefrom said target immune effector cells (autologous cell therapy). In alternative embodiments the method may comprise prior to step (a) a step of obtaining a biological sample of a different subject and isolating therefrom said target immune effector cells (heterologous cell therapy).

As used herein, the term "autologous cell therapy" refers to the implantation, transplantation, infusion, or transfer of cultured cells back into the individual from whom the cells were obtained. For example, immune cells may be obtained from a subject having cancer, expanded into a cell culture, then subjected to the methods of the invention, and reintroduced into the patient in order to boost the subject's immune response. Examples of cells that are useful for autologous culture include but are not limited to stem cells (e.g., hematopoietic stem cells, totipotent stem cells, pluripotent stem cells, fetal stem cells, embryonic stem cells, mesenchymal stem cells, and induced pluripotent stem cells), progenitor cells (e.g., bone marrow stromal cells, angioblasts and endothelial progenitor cells), immune cells (e.g. the above listed immune cells, and in particular T cells, B cells, NK cells, NKT cells, monocytes, macrophages, dendritic cells, granulocytes).

In another embodiment the method for cell therapy of a subject as described above may comprise the use of an established cell line as a target immune effector cell.

The subject in context of the invention is preferably a patient, such as a mammal and preferably a human suffering from a disease, such as cancer.

The method may in some embodiments further comprise a step of introducing into said target immune effector cells an antibody targeting tumour cells, a T-cell receptor (TCR), chimeric antigen receptor (CAR), and/or one or more pro-inflammatory cytokines such as IL-2, IL-12, single-chain IL-12, IL-15, IL-15 hyper-agonist, IL-18, IL-21, GM-CSF, TNF-α, or endoplasmic reticulum-retained or membrane-anchored variants thereof, or any combination of these compounds. In particular embodiments of the invention the method involves the co-expression of such an activator and/or agonist of immune function, and which preferably is an agonist of IL-12 and/or IL-15, and preferably is selected from IL-15 hyper-agonist or single-chain IL-12. It is in this embodiment preferred that the treatment of the invention involves a co-expression in said target immune effector cell of an anti-IL-10 antibody (or a molecule comprising an antigen-binding fragment of an anti-IL-10 antibody) together with either an agonist and/or activator of IL-15 or an agonist and/or activator of IL-12, preferably of IL-15 hyper-agonist or single-chain IL-12. This may be done preferably in target immune effector cells comprising anti-tumour effectors such as CARS or other therapeutic molecules.

As mentioned before, the method for autologous or heterologous cell transfer of the invention is suitable and useful in treating a disease in the subject, preferably a cancer such as brain cancer, colon cancer, renal cancer, head and neck cancer, squamous cell carcinoma, pancreatic cancer, uterine cancer, glioblastoma, medulloblastoma, sarcoma, liver cancer, breast cancer, lung cancer, prostate cancer, ovarian cancer, skin cancer (e.g., carcinoma, melanoma), or liquid cancers such as leukemia or lymphoma, and the like, or an immune disorder such as systemic lupus erythematosus, rheumatoid arthritis, multiple sclerosis, and similar autoimmune disorders. Preferred cancers are also ErbB2 expressing cancers.

In another aspect, an inhibitor of an endogenous regulator of immunity of a target immune effector cell is provided for use in a method for autologous or heterologous cell transfer as described herein above. In some embodiments the immune effector cell is obtained by a method for enhancing the immunological activity of a target immune effector cell as described herein before.

The immune effector cell for use according to the invention may comprise an inhibitor of an endogenous regulator of immunity of a target immune effector cell.

Yet another aspect then pertains to the use of an inhibitor of an endogenous regulator of immunity of a target immune effector cell in a method according to the invention.

In another aspect the invention provides a use of an inhibitor of an endogenous regulator of immunity of a target immune effector cell in adoptive cell therapy for the treatment of a disease such as cancer in a subject.

In all aspects of the invention the inhibitor of an endogenous regulator of immunity of a target immune effector cell is preferably an IL-10 or an IL-6 inhibitor as described before.

In addition the invention further pertains to the following set of items:

Item 1. An in vitro method for enhancing the immunological activity of a target immune effector cell, the method comprising the steps of:
 (a) Providing a target immune effector cell,
 (b) Inhibiting in said target immune effector cell the expression, function, stability or secretion of one or more endogenous regulators of immunity of said target immune effector cell.

Item 2. The in vitro method according to item 1, wherein said endogenous regulator of immunity of said target immune effector cell is a protein having a suppressive activity towards the immunological activity, growth or proliferation of said target immune effector cell, and preferably wherein said protein is selected from IL-1, IL-4, IL-6, IL-10, IL-17, transforming growth factor (TGF)-β, CCL-2/MCP-1, CCL-5/RANTES, indoleamine 2,3-deoxygenase (IDO), vascular endothelial growth factor (VEGF), galectins, fibrinogen-like protein 2 (FGL2), CTLA-4, and/or PD-1; and preferably is IL-10 or IL-6.

Item 3. The method according to items 1 or 2, wherein the target immune effector cell is selected from a monocytic cell, macrophage, dendritic cell, B cell, T cell, NK cell or NKT cell.

Item 4. The method according to any one of items 1 to 3, wherein step (b) comprises bringing into contact the target immune effector cell with an inhibitor of said endogenous regulator of immunity.

Item 5. The method according to any one of items 1 to 4, wherein step (b) involves (i) the use of an inhibitory antibody specific for said endogenous regulator of immunity, (ii) the use of an antisense nucleic acid construct targeting and inhibiting the expression of said endogenous regulator of immunity, or (iii) the use of a gene editing approach introducing a deleterious mutation into the gene sequence of said endogenous regulator of immunity.

Item 6. The method according to any one of items 1 to 5, further comprising a step of bringing into contact the target immune effector cell with an activator or agonist of immune function of the target immune cell, such as a pro-inflammatory cytokine.

Item 7. The method according to item 5, wherein said inhibitory antibody is an anti-IL-10 or anti-IL-6 antibody, or an antigen binding fragment thereof, preferably wherein the anti-IL-10 or anti-IL-6 antibody, or antigen binding fragment thereof, binds and thereby inactivates IL-10 or IL-6, respectively.

Item 8. The method according to item 7, wherein said anti-IL-10 or anti-IL-6 antibody, or antigen binding fragment thereof, (i) is added to said target immune effector cell as a protein preparation, or preferably (ii) is expressed as a genetic construct in said cell, for example as a secreted antibody, or as a membrane-associated antibody, or as an endoplasmic reticulum (ER)-located antibody.

Item 9. An inhibitor of an endogenous regulator of immunity of a target immune effector cell for use in the treatment of a disease, wherein the treatment comprises performing the method according to any one of items 1 to 8, and administering said target immune effector cells having an enhanced immunological activity to the subject.

Item 10. The inhibitor for use according to item 9, wherein the treatment further comprises prior to step (a) a step of obtaining a biological sample of the subject and isolating therefrom said target immune effector cells (autologous cell therapy).

Item 11. The inhibitor for use according to item 9 or 10, wherein the disease is cancer.

Item 12. The inhibitor for use according to any one of items 9 to 11, further comprising a step of introducing into said target immune effector cells an antibody targeting tumour cells, a T-cell receptor (TCR), chimeric antigen receptor (CAR), and/or one or more pro-inflammatory cytokines such as IL-2, IL-12, single-chain IL-12, IL-15, IL-15 hyperagonist, IL-18, IL-21, GM-CSF, TNF-α, or endoplasmic reticulum (ER)-retained or membrane anchored variants thereof, or any combination of these compounds.

Item 13. An immune effector cell for use in the treatment of a disease, wherein the immune effector cell is obtained or is obtainable by a method according to any one of items 1 to 8.

Item 14. Use of an inhibitor of an endogenous regulator of immunity of a target immune effector cell in a method according to any one of items 1 to 9.

Item 15. In vitro use of an inhibitor of an endogenous regulator of immunity of a target immune effector cell in adoptive cell therapy for the treatment of a disease such as cancer in a subject.

The present invention will now be further described in the following examples with reference to the accompanying figures and sequences, nevertheless, without being limited thereto. For the purposes of the present invention, all references as cited herein are incorporated by reference in their entireties. In the Figures:

FIG. 1: Inhibition of IL-10 activity by a recombinant tetravalent anti-IL-10 mini-antibody. (A) Schematic representation of recombinant tetravalent anti-IL-10 mini-antibody. (B) ELISA demonstrating binding of anti-IL-10 mini-antibody (anti-IL-10) to immobilized IL-10. (C) Inhibition of IL-10-induced STAT5 phosphorylation by anti-IL-10 mini-antibody. (D) Natural cytotoxicity of NK cells against NK-sensitive $K_562$ erythroleukemia cells and (E) CAR-mediated cytotoxicity of CAR-engineered ErbB2-specific NK cells against ErbB2-positive MDA-MB453 human breast carcinoma cells in the absence or presence of 2 µg/mL of anti-IL-10 mini-antibody was tested in 2 hour co-culture assays at the indicated effector to target cell (E:T) ratios.

Figure 2:
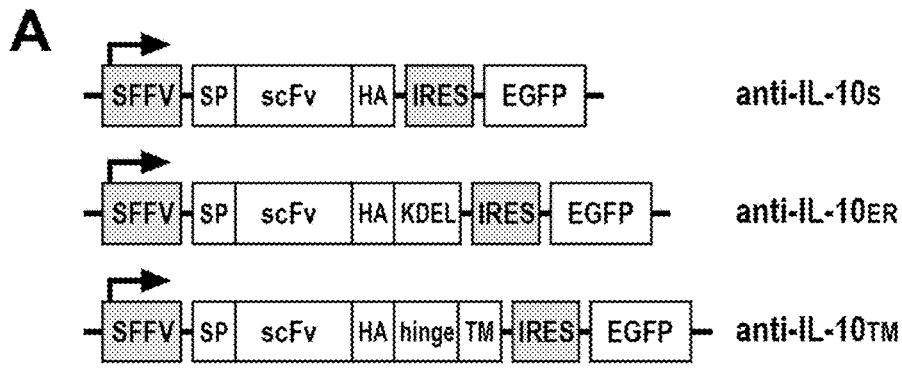
Figure 2:
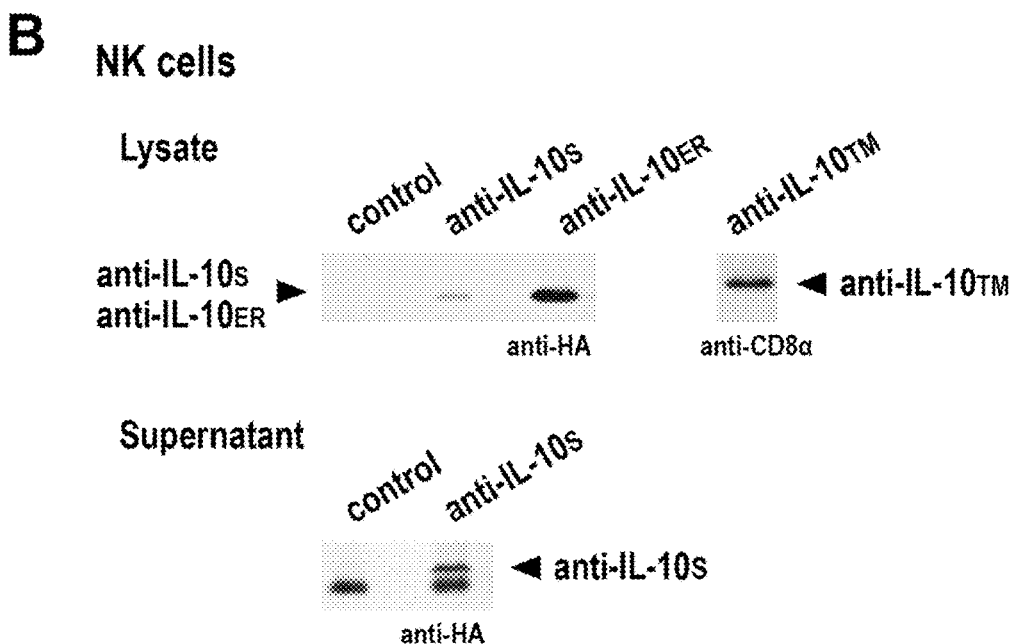
Figure 2:
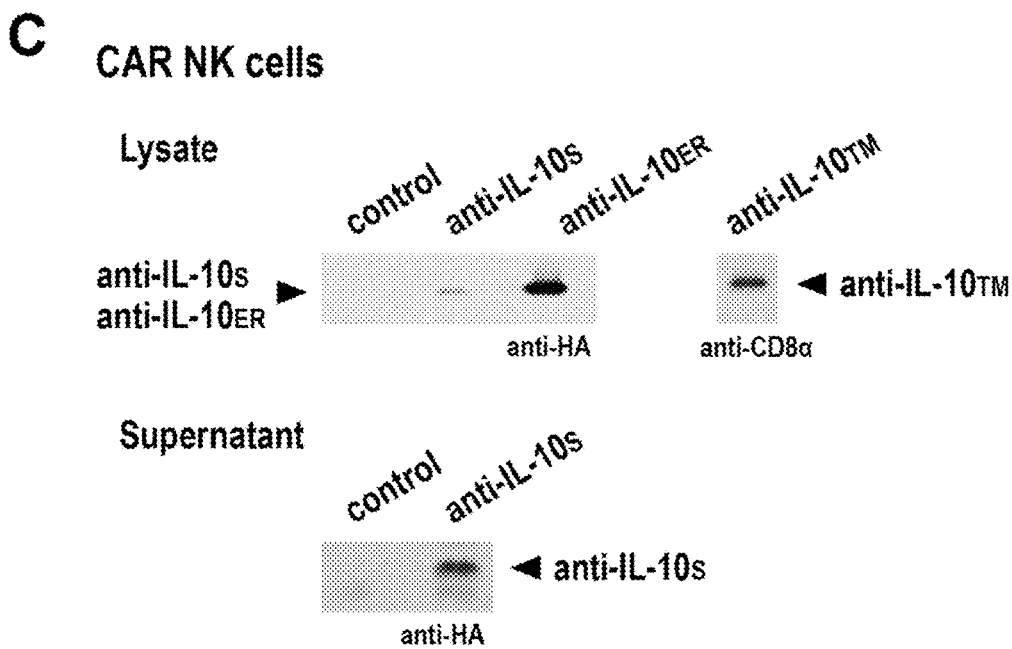

FIG. 2: Intracellular expression of IL-10-neutralizing antibodies in NK and CAR NK cells. (A) Schematic representation of lentiviral vectors for intracellular expression of anti-IL-10 antibodies. Successful expression of secreted (anti-IL10S), ER-retained (anti-IL-10ER) and membrane-anchored (anti-IL-10TM) anti-IL-10 antibodies in lentivirally transduced NK cells (B) and CAR-engineered NK cells expressing an ErbB2-specific chimeric antigen receptor (C) was demonstrated by immunoblot analysis of whole cell lysates or culture supernatants with antibodies detecting an HA-tag (anti-HA) or the CD8a hinge region (anti-CD8a) included in the molecules.

Figure 3:
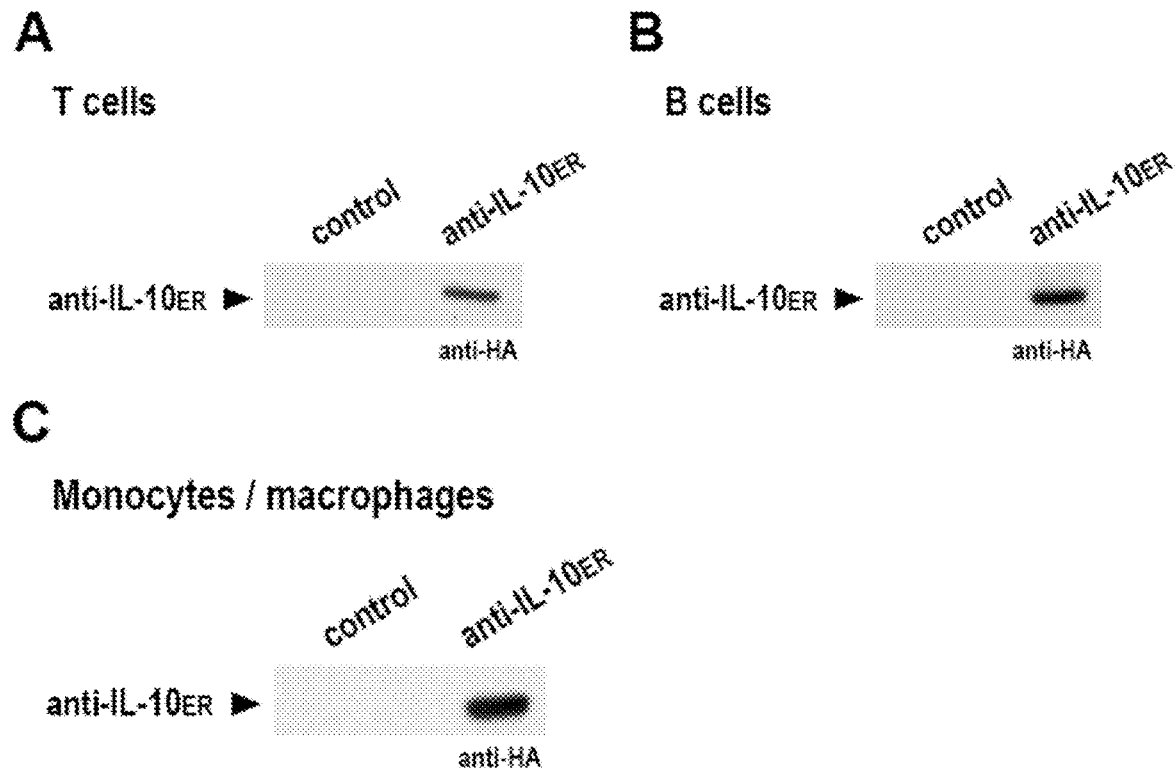

FIG. 3: Intracellular expression of IL-10-neutralizing antibodies in different types of immune effector cells. Intracellular expression of ER-retained anti-IL-10 antibody (anti-IL-10ER) in T cells (A), B cells (B), and macrophages/monocytes (C) was demonstrated by immunoblot analysis of whole cell lysates with an antibody detecting an HA-tag (anti-HA) included in the molecule.

Figure 4:
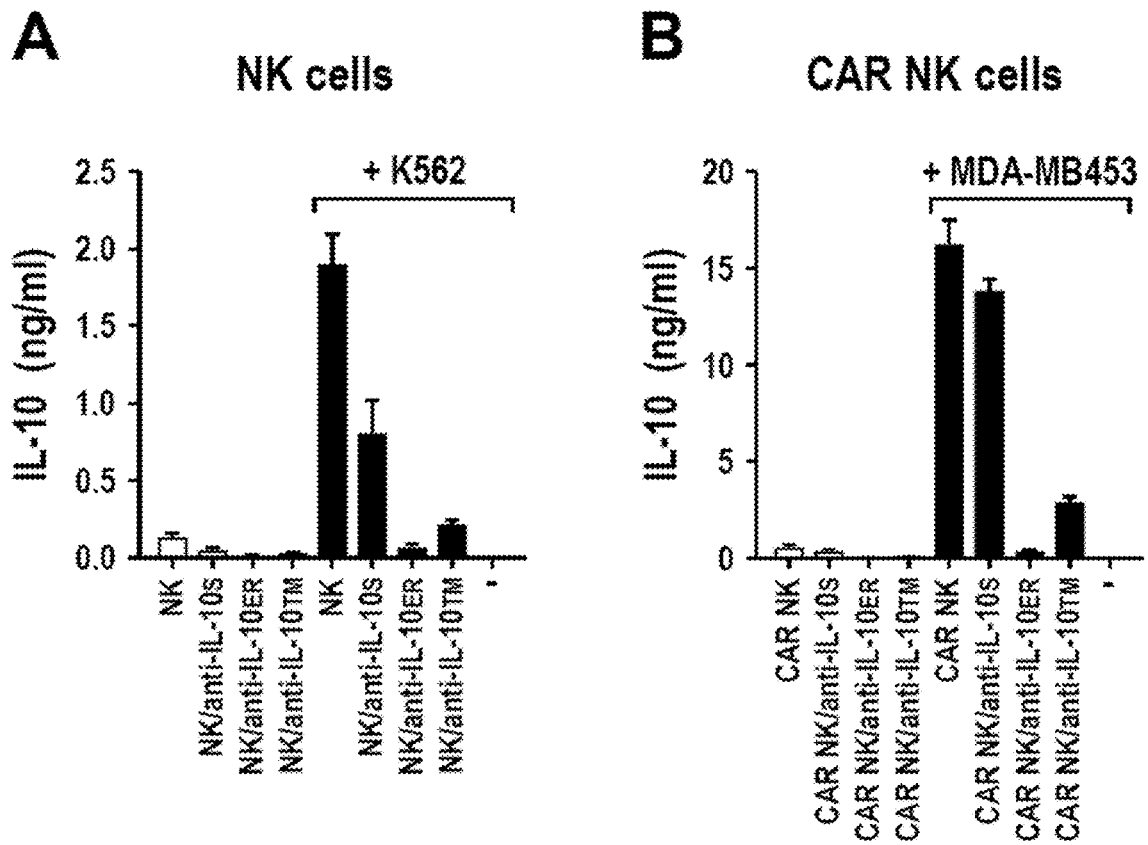
Figure 4:
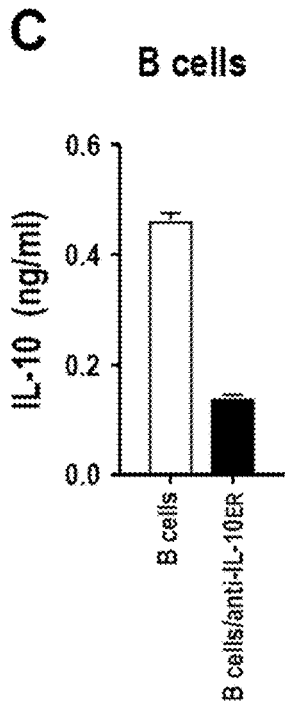

FIG. 4: Inhibition of IL-10 production by intracellular expression of IL-10 neutralizing antibodies. The effect of intracellular expression of anti-IL-10S, anti-IL-10ER and anti-IL-10TM antibodies on activation-induced production of IL-10 by NK cells (A) and NK cells genetically engineered to express an ErbB2-specific CAR (B) was investigated by measuring IL-10 concentrations in culture supernatants upon co-culture with NK-sensitive K562 erythroleukemia cells or ErbB2-expressing MDA-MB453 breast carcinoma cells, respectively. Unmodified NK and CAR NK cells were included for comparison. Similarly, the effect of intracellular expression of recombinant anti-IL-10ER antibody on constitutive IL-10 production by cells of the B-cell lineage was investigated (C).

Figure 5:
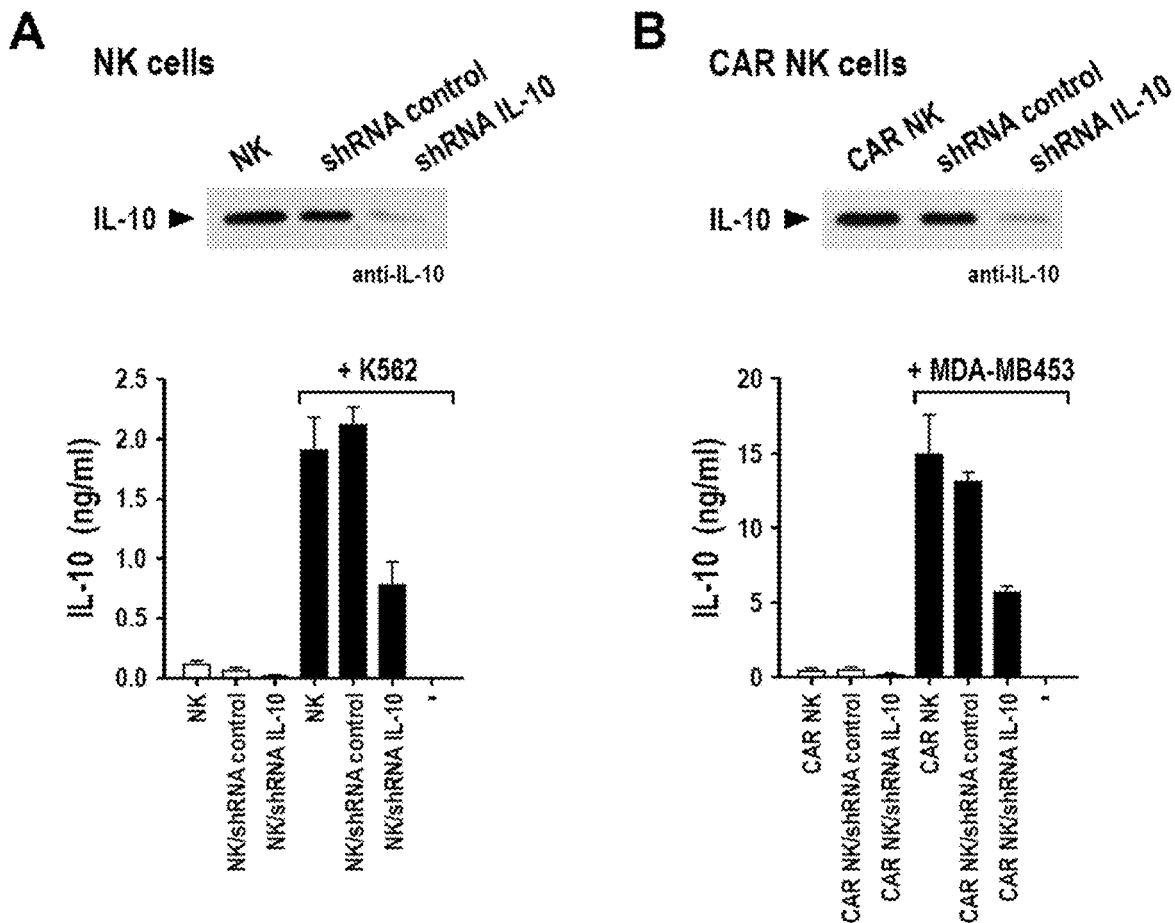

FIG. 5: Silencing of IL-10 expression by IL-10-specific shRNA. The effect of expression of an IL-10-specific shRNA on activation-induced production of IL-10 by NK cells (A) and NK cells genetically engineered to express an ErbB2-specific CAR (B) was investigated by analyzing IL-10 amounts in whole cell lysates after unspecific activation of the cells with PMA/ionomycin (upper panels) and by measuring IL-10 concentrations in culture supernatants upon co-culture with NK-sensitive K562 erythroleukemia cells or ErbB2-expressing MDA-MB453 breast carcinoma cells, respectively (lower panels). Unmodified NK and CAR NK cells as well as NK and CAR NK cells transduced with an irrelevant control shRNA vector were included as controls.

Figure 6:
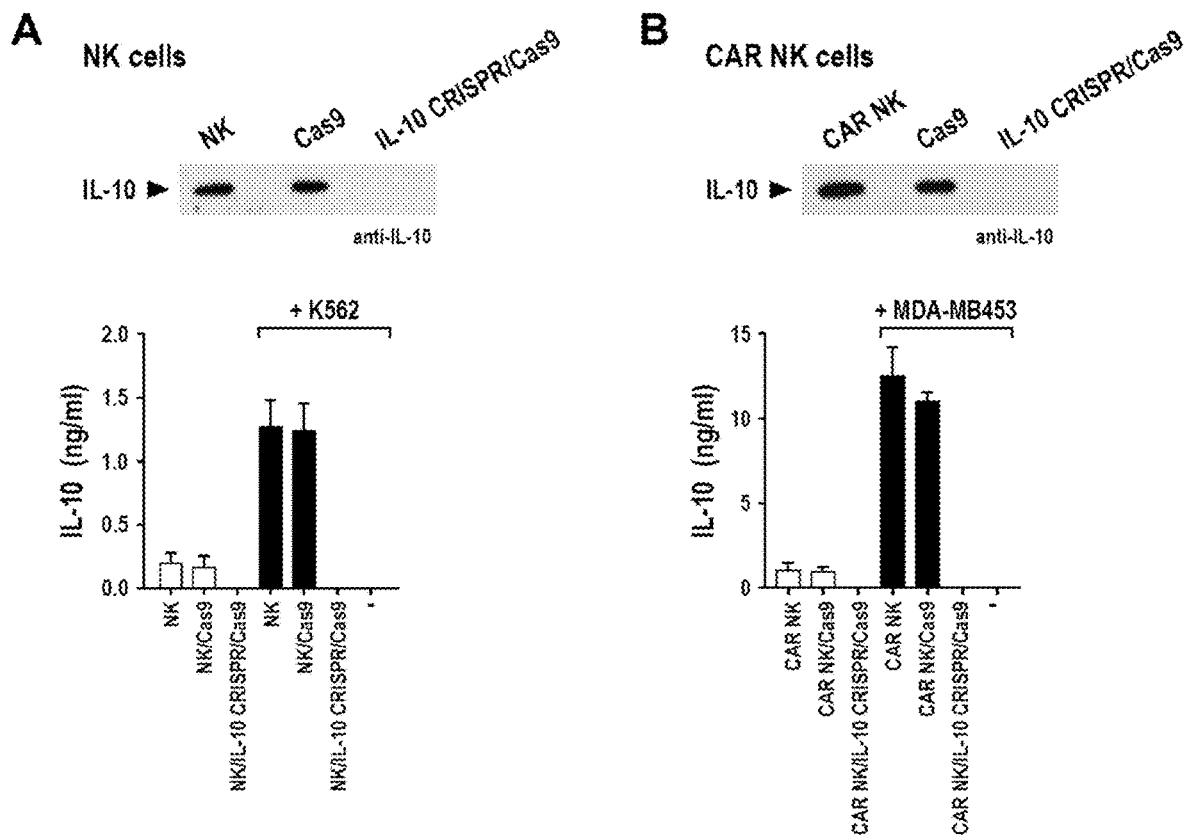

FIG. 6: Downregulation of IL-10 expression by CRISPR/Cas9-mediated gene editing. The effect of targeted knockout of IL-10 expression using the CRISPR/Cas9 system on activation-induced production of IL-10 by NK cells (A) and NK cells genetically engineered to express an ErbB2-specific CAR (B) was investigated by analyzing IL-10 amounts in whole cell lysates after unspecific activation of the cells with PMA/ionomycin (upper panels) and by measuring IL-10 concentrations in culture supernatants upon co-culture with NK-sensitive K562 erythroleukemia cells or ErbB2-expressing MDA-MB453 breast carcinoma cells, respectively (lower panels). Unmodified NK and CAR NK cells as well as NK and CAR NK cells only expressing Cas9 nuclease in the absence of IL-10-specific guide RNA (Cas9) were included as controls.

Figure 7:
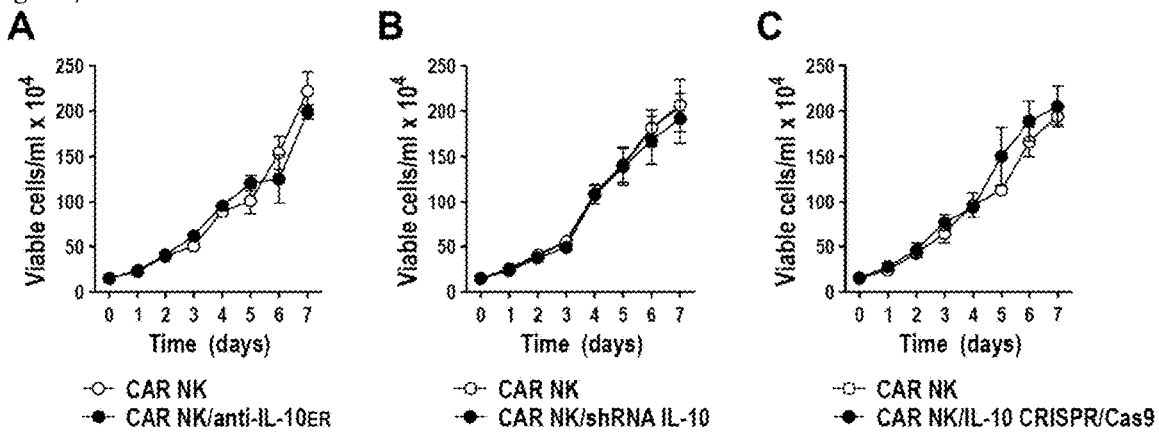

FIG. 7: Viability and proliferation of immune effector cells after downregulation of IL-10 production. To assess possible consequences of downregulation of IL-10 expression on the growth of immune effector cells, NK cells genetically engineered to express an ErbB2-specific CAR together with an ER-retained anti-IL-10 antibody (anti-IL-10ER) (A), IL-10-specific shRNA (shRNA IL-10) (B), or Cas9 nuclease and IL-m-specific guide RNA (IL-10 CRISPR/Cas9) (C) were seeded in 24-well cell culture plates on day 0 at a cell density of $1.5 \times 10^5$ cells/mL, and cell growth was monitored by counting viable cells using trypan blue exclusion once per day for a period of 7 days. CAR NK cells with undisturbed IL-10 expression were included as controls.

Figure 8:
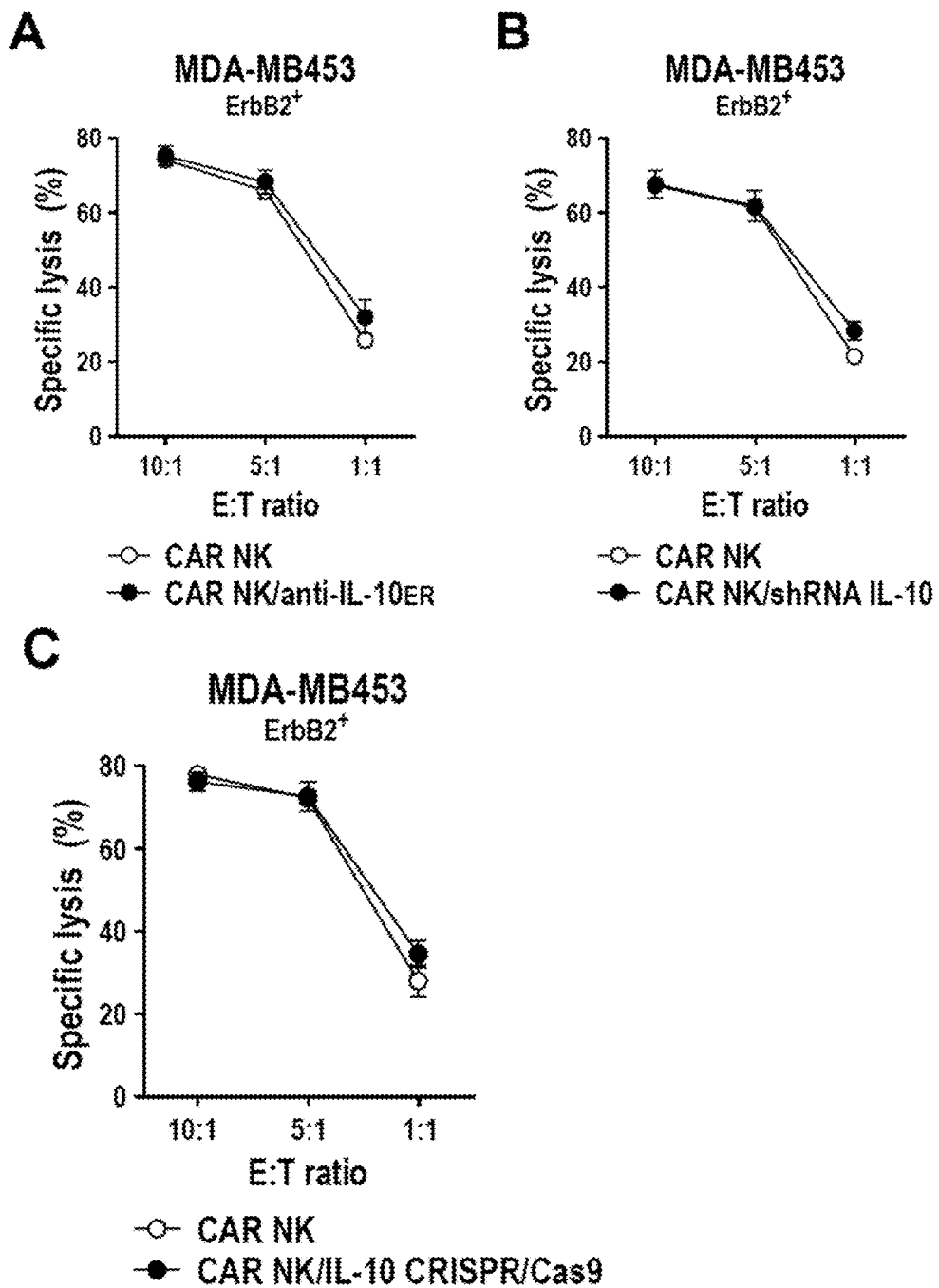

FIG. 8: Antitumour activity of immune effector cells after downregulation of IL-10 production. To assess possible consequences of downregulation of IL-10 expression on specific cytotoxicity and direct antitumour activity, CAR-mediated cytotoxicity of CAR-engineered ErbB2-specific NK cells also expressing an ER-retained anti-IL-10 antibody (anti-IL-10ER) (A), IL-10-specific shRNA (shRNA IL-10) (B), or Cas9 nuclease together with IL-10-specific guide RNA (IL-10 CRISPR/Cas9) (C) against ErbB2-positive MDA-MB453 human breast carcinoma cells was tested in 2 hour co-culture assays at the indicated E:T ratios. CAR NK cells with undisturbed IL-10 expression were included for comparison.

Figure 9:
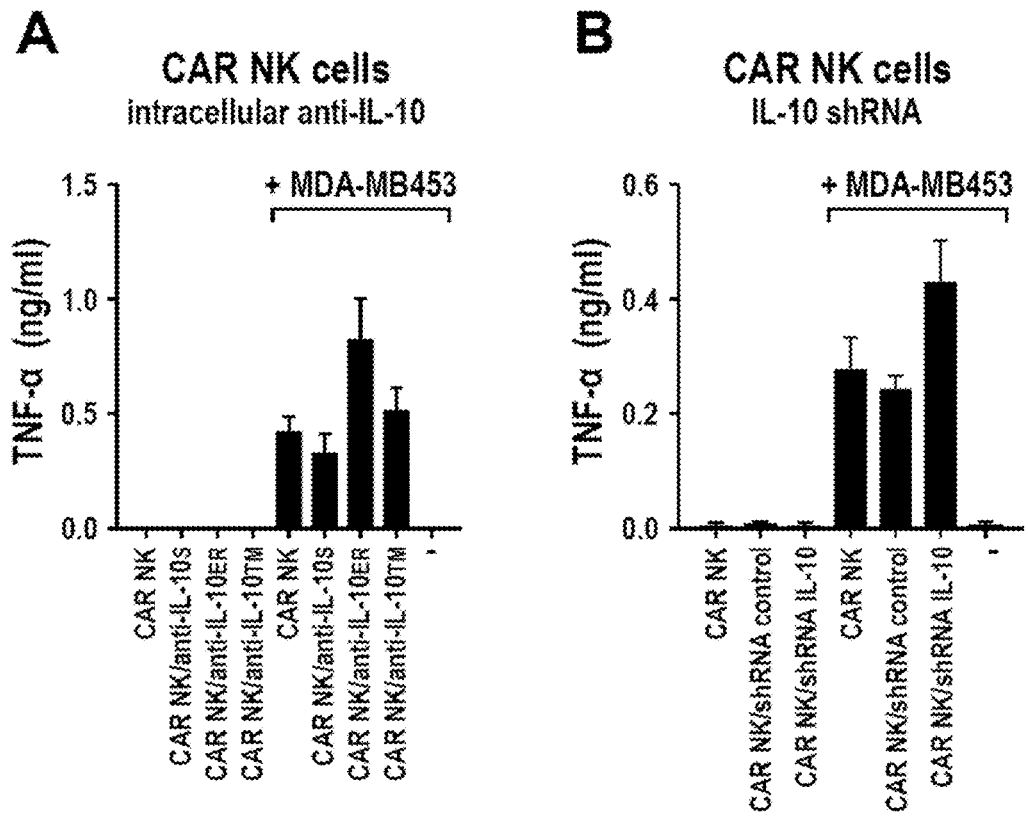

FIG. 9: Downregulation of IL-10 production in immune effector cells enhances production of the pro-inflammatory cytokine TNF-α. ErbB2-specific CAR NK cells transduced with lentiviral vectors encoding anti-IL-10S, anti-IL-10ER, anti-IL-10TM (A) or IL-m-specific shRNA (B) were cultured in the absence or presence of ErbB2-expressing MDA-MB453 breast carcinoma cells for 6 hours. CAR NK cells with undisturbed IL-10 expression and CAR NK cells transduced with an irrelevant shRNA construct were included as controls. TNF-α concentration in culture supernatants was measured using a cytometric bead array.

Figure 10:
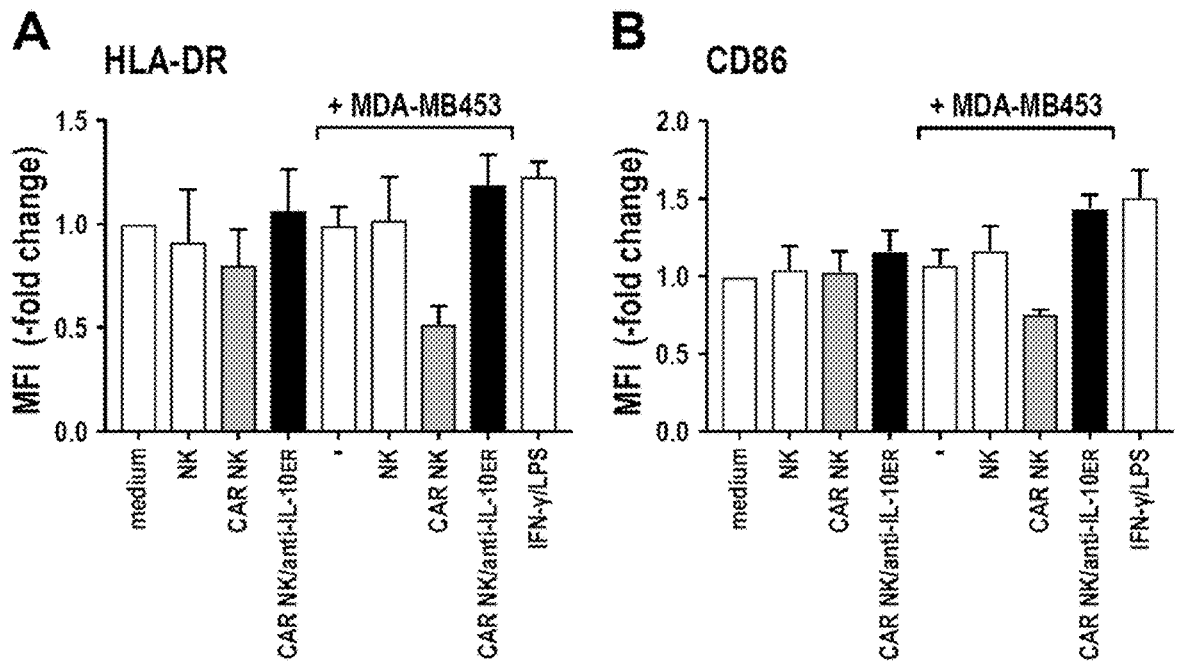
Figure 10:
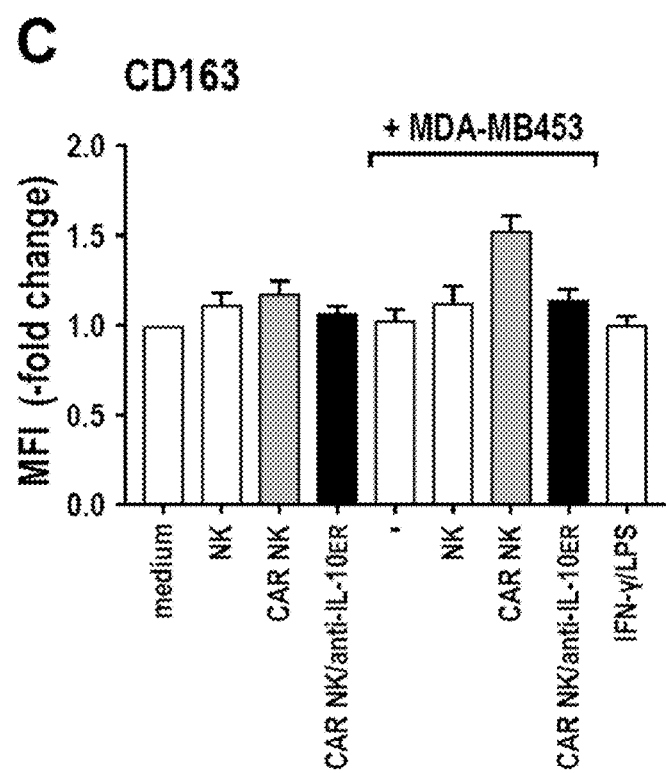

FIG. 10: Downregulation of IL-10 production in immune effector cells prevents polarization of bystander macrophages towards a tumour-promoting M2 phenotype. Transwell assays were performed with macrophages cultured in the bottom chamber, separated by a membrane from co-cultured ErbB2-specific CAR NK cells in the upper chamber. CAR NK cells co-expressing anti-IL-10ER were either kept alone, or co-cultured in the upper chamber with ErbB2-expressing MDA-MB453 breast carcinoma cells. Unmodified NK cells without CAR and anti-IL-10ER expression and CAR NK cells without anti-IL10ER expression were included as controls. For comparison, macrophages cultured in the absence of NK cells were treated with IFN-γ and LPS. After 24 hours, macrophages were harvested and polarization was investigated by measuring the surface markers HLA-DR (A), CD86 (B) and CD163 (C) by flow cytometry with specific antibodies. MFI: mean fluorescence intensity (geometric mean).

Figure 11:
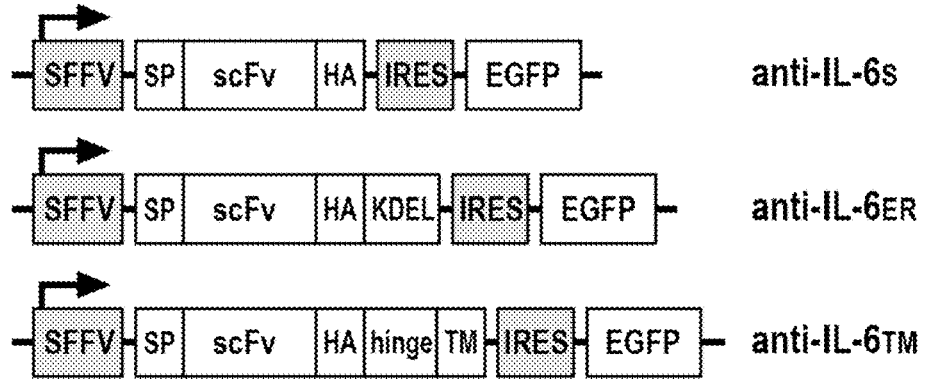
Figure 11:
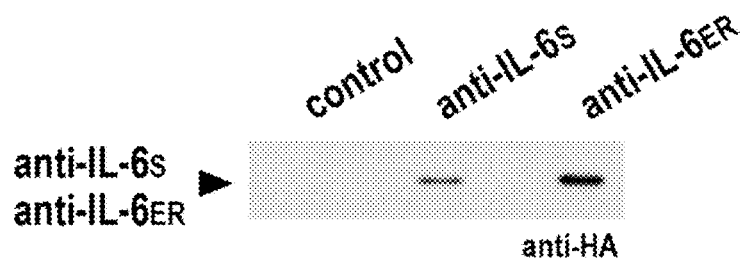
Figure 11:
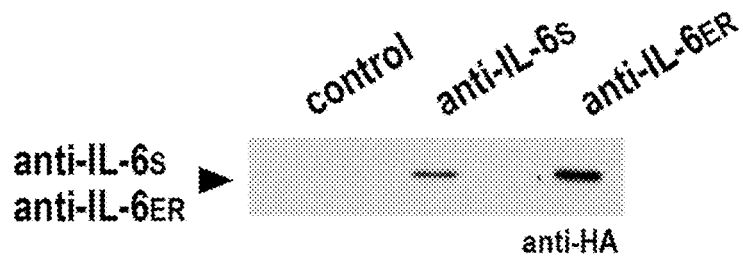
Figure 11:
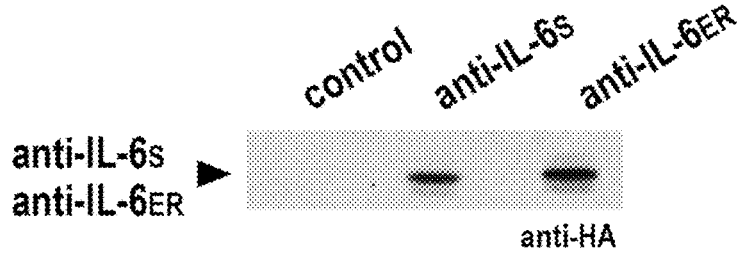

FIG. 11: Intracellular expression of IL-6-neutralizing antibodies in different types of immune effector cells. (A) Schematic representation of lentiviral vectors for intracellular expression of anti-IL-6 antibodies. Shown are constructs for expression of secreted (anti-IL-6S), ER-retained (anti-IL-6ER) and membrane-anchored (anti-IL-6TM) anti-IL-6 antibodies in lentivirally transduced immune effector cells. SFFV: spleen focus forming virus promoter; SP: signal peptide; scFv: single chain antibody; HA: HA-tag for immunological detection; KDEL: KDEL ER retention sequence; hinge: CD8a hinge region; TM: CD28 transmembrane domain; IRES: internal ribosome entry site; EGFP: enhanced green fluorescent protein sequence (marker gene). Successful expression of secreted (anti-IL-6S) and ER-retained (anti-IL-6ER) anti-IL-6 antibodies in lentivirally transduced NK cells (B), CAR-engineered NK cells expressing an ErbB2-specific chimeric antigen receptor (C), and macrophages/monocytes (D) was demonstrated by immunoblot analysis of whole cell lysates with an antibody detecting an HA-tag (anti-HA) included in the molecule.

Figure 12:
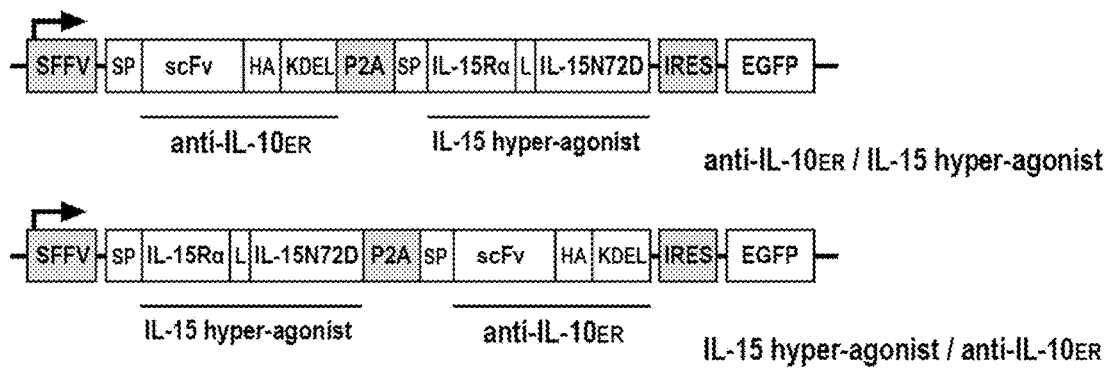
Figure 12:
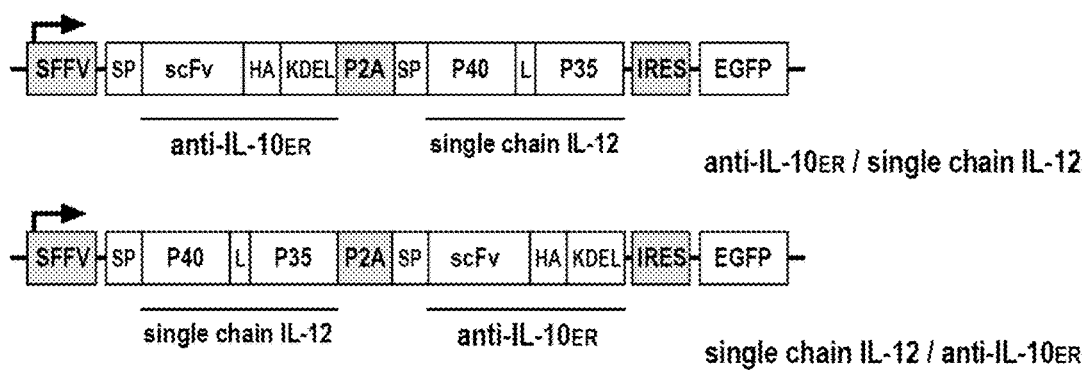
Figure 12:
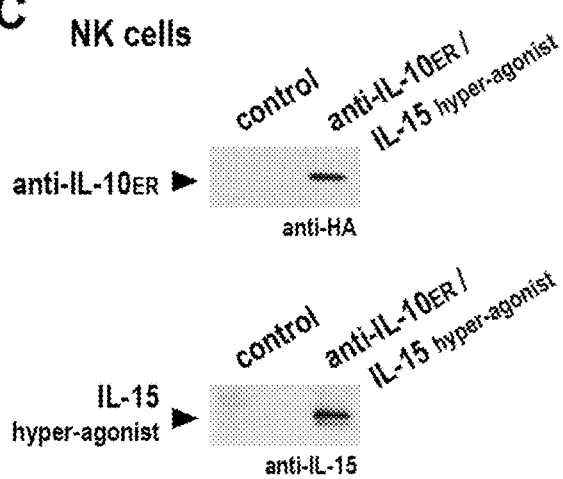
Figure 12:
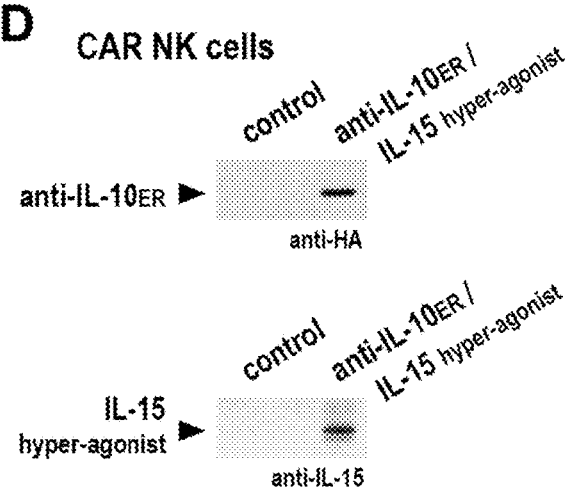

FIG. 12: Intracellular expression of anti-IL-10 antibodies together with IL-15 hyper-agonist or single chain IL-12. Shown are constructs for co-expression of ER-retained (anti-IL-10ER) anti-IL-10 single chain antibody together with IL-15 hyper-agonist (A) or single chain IL-12 (B) in lentivirally transduced immune effector cells. SFFV: spleen focus forming virus promoter; SP: signal peptide; scFv: single chain antibody; HA: HA-tag for immunological detection; KDEL: KDEL ER retention sequence; P2A: self-cleaving 2A peptide from porcine teschovirus-1; IL15Ra: IL-15 receptor α sushi domain; L: linker sequence; IL15N72D: modified IL-15; P40: IL-12 No domain; P35: IL-12 P35 domain; IRES: internal ribosome entry site; EGFP: enhanced green fluorescent protein sequence (marker gene). Successful co-expression of ER-retained (anti-IL-10ER) anti-IL-10 antibody and IL-15 hyper-agonist in lentivirally transduced NK cells (C) and CAR-engineered NK cells expressing an ErbB2-specific chimeric antigen receptor (D) was demonstrated by immunoblot analysis of whole cell lysates with antibodies detecting an HA-tag (anti-HA) included in the anti-IL-10ER molecule or the IL-15 domain (anti-IL-15) included in IL-15 hyper-agonist using the construct displayed in (A), lower panel.

Figure 13:
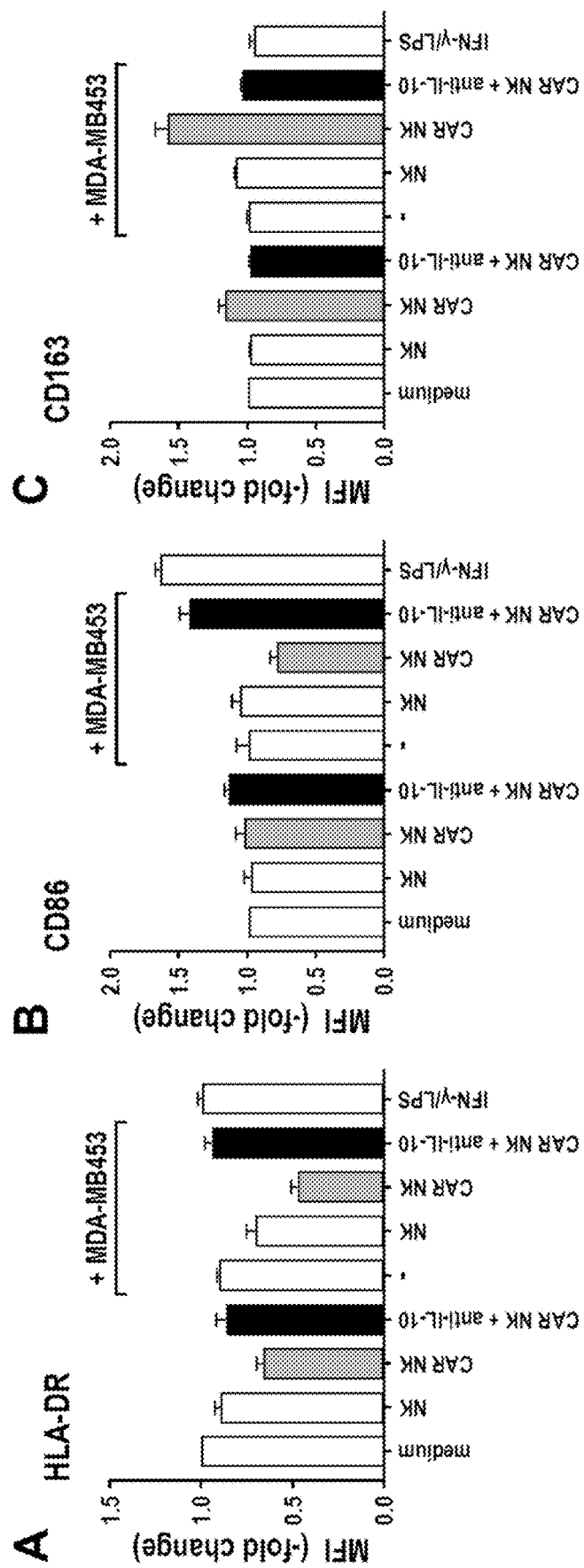

FIG. 13: Inhibition of the activity of IL-10 secreted by immune effector cells prevents polarization of bystander macrophages towards a tumour-promoting M2 phenotype. Transwell assays were performed with macrophages cultured in the bottom chamber, separated by a membrane from co-cultured ErbB2-specific CAR NK cells in the upper chamber in the presence of tetravalent anti-IL-10 mini-antibody. CAR NK cells in the presence of tetravalent anti-IL-10 mini-antibody were either kept alone, or co-cultured in the upper chamber with ErbB2-expressing MDA-MB453 breast carcinoma cells. Unmodified NK cells without CAR and CAR NK cells without addition of tetravalent anti-IL-10 mini-antibody were included as controls. For comparison, macrophages cultured in the absence of NK cells were treated with IFN-γ and LPS. After 24 hours, macrophages were harvested and polarization was investigated by measuring the surface markers HLA-DR (A), CD86 (B) and CD163 (C) by flow cytometry with specific antibodies. MFI: mean fluorescence intensity (geometric mean).

Figure 14:
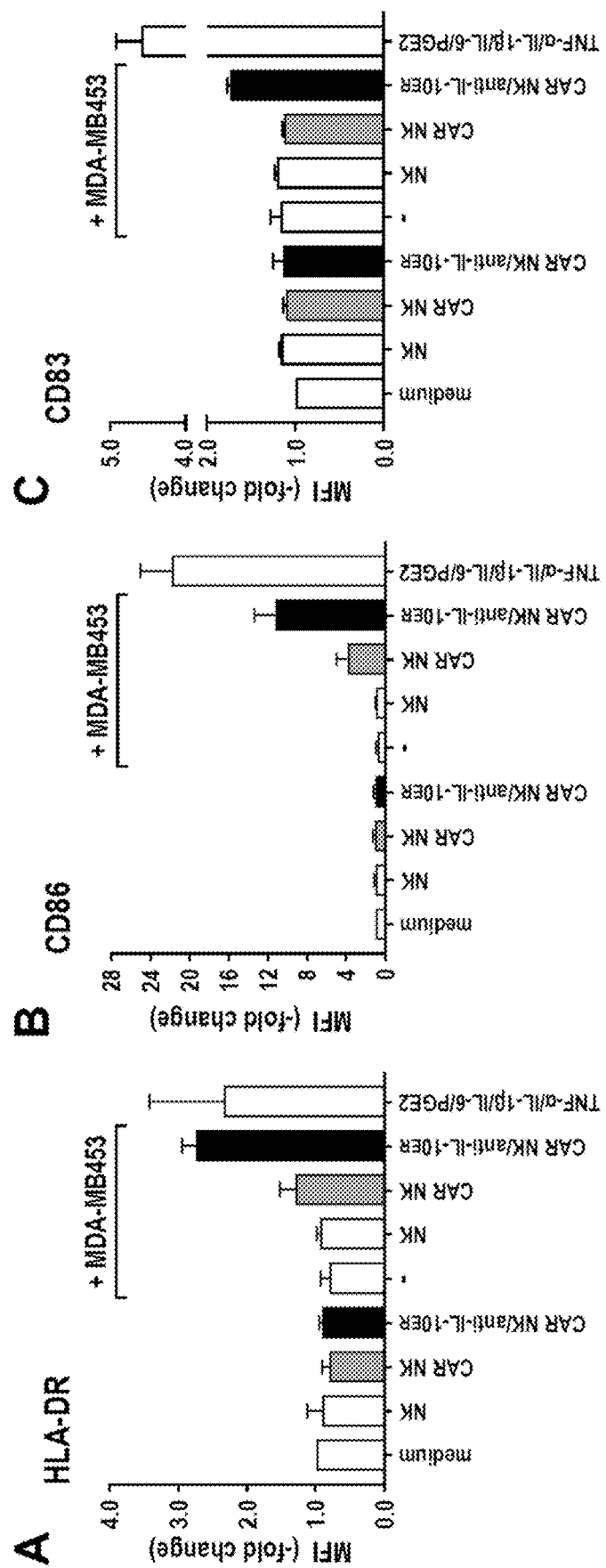

FIG. 14: Downregulation of IL-10 production in immune effector cells enhances maturation of bystander dendritic cells. Transwell assays were performed with immature human monocyte-derived dendritic cells cultured in the bottom chamber, separated by a membrane from co-cultured ErbB2-specific CAR NK cells in the upper chamber. CAR NK cells co-expressing anti-IL-10ER were either kept alone, or co-cultured in the upper chamber with ErbB2-positive MDA-MB453 mammary carcinoma cells. MDA-MB453 cells alone, NK-92 cells without CAR and anti-IL-10ER expression (NK) and CAR NK cells without anti-IL-10ER expression were included as controls. For comparison, DC maturation was induced in the absence of NK cells with TNF-α, IL-1β, IL-6 and prostaglandin E2 (PGE2). After 24 hours, DCs were harvested and their maturation state was investigated by flow cytometric analysis of the surface markers HLA-DR (A), CD86 (B) and CD83 (C) with specific antibodies. MFI: mean fluorescence intensity (geometric mean).

Figure 15:
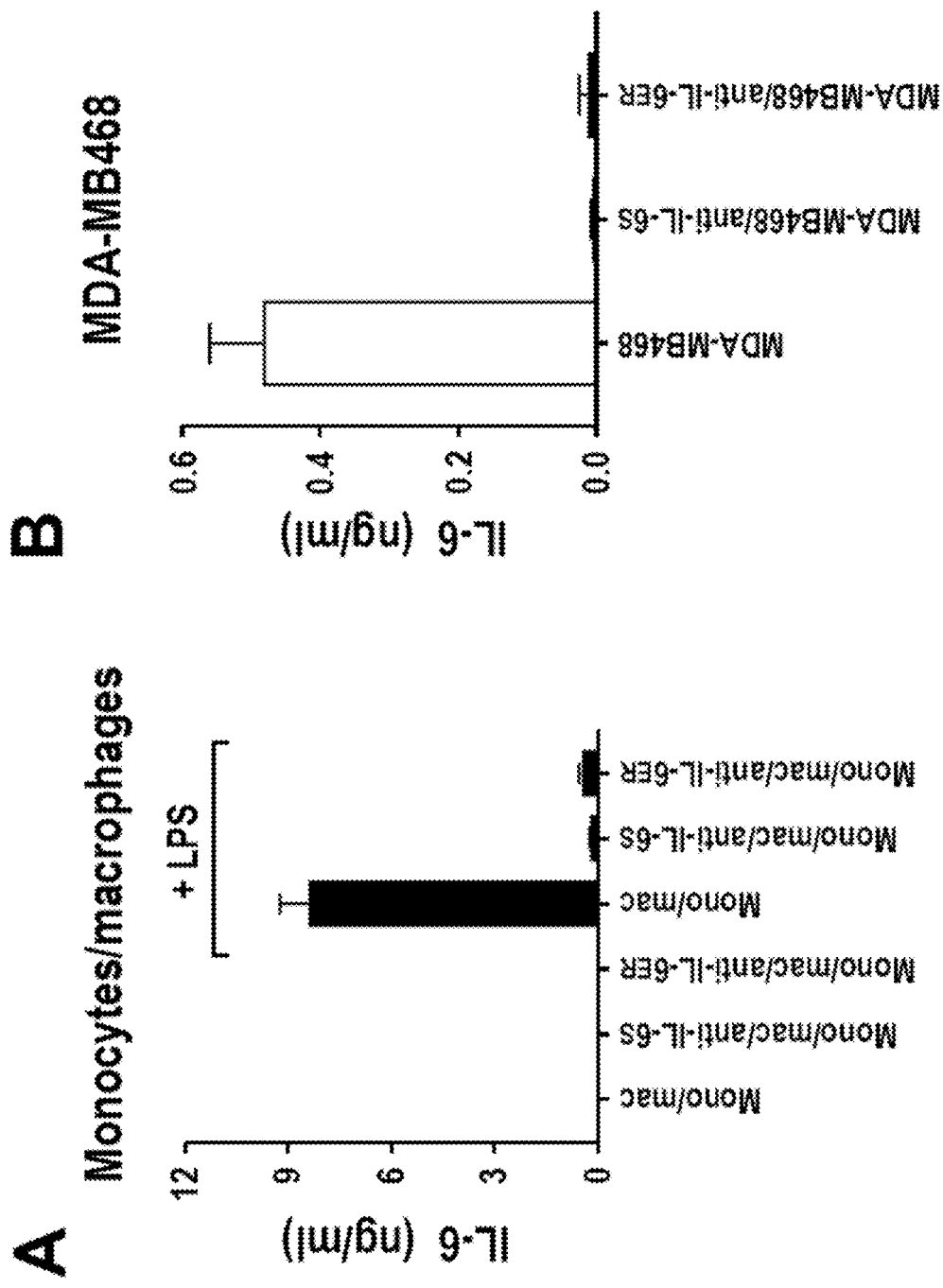

FIG. 15: Inhibition of IL-6 production by intracellular expression of IL-6-neutralizing antibodies. The effect of intracellular expression of anti-IL-6S and anti-IL6ER antibodies on activation-induced production of IL-6 by macrophages/monocytes (mono/mac) was investigated by measuring IL-6 concentrations in culture supernatants upon activation of macrophages/monocytes with 100 ng/mL LPS for 16 hours (A). Macrophages/monocytes kept without LPS were included for comparison. Similarly, anti-IL-6S and anti-IL-6ER antibodies were expressed in lentivirally transduced MDA-MB468 breast carcinoma cells which constitutively produce IL-6, and the effect of the intracellularly expressed anti-IL-6 antibodies on the production of IL-6 was investigated by measuring IL-6 concentrations in culture supernatants after 6 hours of culture (B).

And in the sequences:

TABLE 1

Sequence description with reference to the attached sequence protocol

| NO: | Description: | Domains and regions: |
|---|---|---|
| 1 | anti-IL-10 mini-antibody DNA | complete sequence 2235 bp; 1 . . . 57 signal peptide; 58 . . . 408 variable domain heavy chain; 409 . . . 453 linker; 454 . . . 789 variable domain light chain; 790 . . . 1500 IgG4 Fc region; 1501 . . . 1851 variable domain heavy chain; 1852 . . . 1896 linker; 1897 . . . 2232 variable domain light chain; 2233 . . . 2235 stop codon |
| 2 | anti-IL-10 mini-antibody protein | complete sequence 744 aa; 1 . . . 19 signal peptide; 20 . . . 136 variable domain heavy chain; 137 . . . 151 linker; 152 . . . 263 variable domain light chain; 264 . . . 500 IgG4 Fc region; 501 . . . 617 variable domain heavy chain; 618 . . . 632 linker; 633 . . . 744 variable domain light chain |
| 3 | anti-IL-10ER DNA | complete sequence 831 bp; 1 . . . 57 signal peptide; 58 . . . 408 variable domain heavy chain; 409 . . . 453 linker; 454 . . . 789 variable domain light chain; 790 . . . 816 HA tag; 817 . . . 828 ER retention signal; 829 . . . 831 stop codon |
| 4 | anti-IL-10ER protein | complete sequence 276 aa; 1 . . . 19 signal peptide; 20 . . . 136 variable domain heavy chain; 137 . . . 151 linker; 152 . . . 263 variable domain light chain; 264 . . . 272 HA tag; 273 . . . 276 ER retention signal |
| 5 | anti-IL-10S DNA | complete sequence 819 bp; 1 . . . 57 signal peptide; 58 . . . 408 variable domain heavy chain; 409 . . . 453 linker; 454 . . . 789 variable domain light chain; 790 . . . 816 HA tag; 817 . . . 819 stop codon |
| 6 | anti-IL-10S protein | complete sequence 272 aa; 1 . . . 19 signal peptide; 20 . . . 136 variable domain heavy chain; 137 . . . 151 linker; 152 . . . 263 variable domain light chain; 264 . . . 272 HA tag |
| 7 | anti-IL-10TM DNA | complete sequence 1113 bp; 1 . . . 57 signal peptide; 58 . . . 408 variable domain heavy chain; 409 . . . 453 linker; 454 . . . 789 variable domain light chain; 790 . . . 816 HA tag; 817 . . . 1002 CD8alpha hinge region; 1003 . . . 1110 CD28 transmembrane domain; 1111 . . . 1113 stop codon |
| 8 | anti-IL-10TM protein | complete sequence 370 aa; 1 . . . 19 signal peptide; 20 . . . 136 variable domain heavy chain; 137 . . . 151 linker; 152 . . . 263 variable domain light chain; 264 . . . 272 HA tag; 273 . . . 334 CD8alpha hinge region; 335 . . . 370 CD28 transmembrane domain |
| 9 | anti-IL-10ER-P2A-single chain IL-12 DNA | complete sequence 2484 bp; 1 . . . 57 signal peptide; 58 . . . 408 variable domain heavy chain; 409 . . . 453 linker; 454 . . . 789 variable domain light chain; 790 . . . 816 HA tag; 817 . . . 828 ER retention signal; 829 . . . 885 P2A sequence; 886 . . . 2481 single chain IL-12; 2482 . . . 2484 stop codon |
| 10 | anti-IL-10ER-P2A-single chain IL-12 protein | complete sequence 827 aa; 1 . . . 19 signal peptide; 20 . . . 136 variable domain heavy chain; 137 . . . 151 linker; 152 . . . 263 variable domain light chain; 264 . . . 272 HA tag; 273 . . . 276 ER retention signal; 277 . . . 295 P2A sequence; 296 . . . 827 single chain IL-12 |
| 11 | anti-IL-10ER-P2A-IL-15 hyper-agonist DNA | complete sequence 1578 bp; 1 . . . 57 signal peptide; 58 . . . 408 variable domain heavy chain; 409 . . . 453 linker; 454 . . . 789 variable domain light chain; 790 . . . 816 HA tag; 817 . . . 828 ER retention signal; 829 . . . 885 P2A sequence; 886 . . . 1575 IL-15 hyper-agonist; 1576 . . . 1579 stop codon |

TABLE 1-continued

Sequence description with reference to the attached sequence protocol

| NO: | Description: | Domains and regions: |
|---|---|---|
| 12 | anti-IL-10ER-P2A-IL-15 hyper-agonist protein | complete sequence 525 aa; 1 . . . 19 signal peptide; 20 . . . 136 variable domain heavy chain; 137 . . . 151 linker; 152 . . . 263 variable domain light chain; 264 . . . 272 HA tag; 273 . . . 276 ER retention signal; 277 . . . 295 P2A sequence; 296 . . . 525 IL-15 hyper-agonist |
| 13 | anti-IL-6ER DNA | complete sequence 828 bp; 1 . . . 57 signal peptide; 58 . . . 417 variable domain heavy chain; 418 . . . 462 linker; 463 . . . 786 variable domain light chain; 787 . . . 813 HA tag; 814 . . . 825 ER retention signal; 826 . . . 828 stop codon |
| 14 | anti-IL-6ER protein | complete sequence 275 aa; 1 . . . 19 signal peptide; 20 . . . 139 variable domain heavy chain; 140 . . . 154 linker; 155 . . . 262 variable domain light chain; 263 . . . 271 HA tag; 272 . . . 275 ER retention signal |
| 15 | anti-IL-6S DNA | complete sequence 816 bp; 1 . . . 57 signal peptide; 58 . . . 417 variable domain heavy chain; 418 . . . 462 linker; 463 . . . 786 variable domain light chain; 787 . . . 813 HA tag; 814 . . . 816 stop codon |
| 16 | anti-IL-6S protein | complete sequence 271 aa; 1 . . . 19 signal peptide; 20 . . . 139 variable domain heavy chain; 140 . . . 154 linker; 155 . . . 262 variable domain light chain; 263 . . . 271 HA tag |
| 17 | anti-IL-6TM DNA | complete sequence 1110 bp; 1 . . . 57 signal peptide; 58 . . . 417 variable domain heavy chain; 418 . . . 462 linker; 463 . . . 786 variable domain light chain; 787 . . . 813 HA tag; 814 . . . 999 CD8alpha hinge region; 1000 . . . 1107 CD28 transmembrane domain; 1108 . . . 1110 stop codon |
| 18 | anti-IL-6TM protein | complete sequence 369 aa; 1 . . . 19 signal peptide; 20 . . . 139 variable domain heavy chain; 140 . . . 154 linker; 155 . . . 262 variable domain light chain; 263 . . . 271 HA tag; 272 . . . 333 CD8alpha hinge region; 334 . . . 369 CD28 transmembrane domain |
| 19 | IL10 gRNA 1f | RNA sequence provided as DNA code (T instead of U) |
| 20 | IL10 gRNA 1r | RNA sequence provided as DNA code (T instead of U) |
| 21 | IL10 gRNA 2f | RNA sequence provided as DNA code (T instead of U) |
| 22 | IL10 gRNA 2r | RNA sequence provided as DNA code (T instead of U) |
| 23 | IL10 gRNA 3f | RNA sequence provided as DNA code (T instead of U) |
| 24 | IL10 gRNA 3r | RNA sequence provided as DNA code (T instead of U) |
| 25 | IL10 gRNA 4f | RNA sequence provided as DNA code (T instead of U) |
| 26 | IL10 gRNA 4r | RNA sequence provided as DNA code (T instead of U) |
| 27 | IL-10 shRNA | RNA sequence provided as DNA code (T instead of U) |
| 28 | IL-10 full length protein | Immature protein sequence |
| 29 | IL-6 full length protein | Immature protein sequence |

EXAMPLES

Example 1: Inhibition of IL-10 Activity by a Recombinant Tetravalent Anti-IL-10 Antibody Monoclonal anti-IL-10 antibodies able to interfere with IL-10 activity have been described by different groups, with one of them having already been tested in a phase I clinical trial for systemic lupus erythematosus. Nevertheless, such IgG antibodies only possess two antigen binding sites which may limit their therapeutic potential. To enhance IL-10-neutralizing activity, the inventors designed a novel recombinant anti-IL-10 mini-antibody with four IL-10 binding domains. This tetravalent mini-antibody is a disulfide-linked homodimer of a molecule consisting of a single chain variable fragment (scFv) of anti-IL-10 antibody BT-063 (PCT/EP2010/068569) fused to hinge, CH2 and CH3 domains of human IgG4 and a second scFv fragment of BT-063 (FIG. 1A).

Secretion of the recombinant antibody was achieved via an immunoglobulin heavy chain signal peptide at the very N-terminus. The anti-IL-10 mini-antibody was expressed in human HEK 293 cells and purified from culture supernatant by Protein G affinity chromatography. Specific binding of purified anti-IL-10 mini-antibody to recombinant human IL-10 (rhIL-10) was demonstrated by ELISA (FIG. 1B). To confirm IL-10-neutralizing activity of the anti-IL-10 mini-antibody, inhibition of IL-10-mediated activation of signal transducer and activator of transcription 3 (STAT3) in IL-10 receptor positive NK cells was investigated. IL-2-starved human NK cells were co-incubated with 40 ng/mL of IL-10 in the absence or presence of increasing concentrations of anti-IL-10 mini-antibody (FIG. 1C). Phosphorylation of STAT3 as a measure of IL-10-induced STAT3 activation was then investigated by immunoblot analysis of whole cell lysates with phospho-STAT3-specific antibody. While IL-10 induced marked STAT3 activation in NK cells in the absence of anti-IL-10 antibody, this was completely prevented by the recombinant molecule demonstrating its IL-10-neutralizing activity (FIG. 1C). Importantly, anti-IL-10 mini-antibody did neither inhibit natural cytotoxicity of human NK cells (FIG. 1D) nor specific CAR-mediated cytotoxicity of genetically engineered NK cells expressing an ErbB2-specific CAR (FIG. 1E).

The data of Example 1 demonstrate that an anti-IL-10 antibody such as the tetravalent anti-IL-10 mini-antibody described herein can be used to block undesired IL-10-induced activities during adoptive cell therapy without limiting the direct antitumour activity of unmodified or CAR-engineered immune effector cells.

Example 2: Intracellular Expression of IL-10-Neutralizing Antibodies

In a second approach the inventors designed recombinant anti-IL-10 antibodies for direct expression in immune effector cells to block IL-10 activity in the extracellular space (secreted anti-IL-10; anti-IL-10S), prevent secretion of endogenously synthesized IL-10 by inhibiting its transport to the cell surface (endoplasmic reticulum-retained anti-IL-10; anti-IL-10ER), or trap IL-10 on the cell surface (transmembrane anti-IL-10; anti-IL-10TM). Anti-IL-10S consists of an N-terminal immunoglobulin heavy chain signal peptide for direction into the secretory pathway, an scFv fragment of anti-IL-10 antibody BT-063, and a peptide derived from human influenza virus hemagglutinin (HA-tag) for immunological detection (FIG. 2A). Anti-IL-10ER in addition contains a C-terminal KDEL peptide sequence for binding to the KDEL receptor in the endoplasmic reticulum (ER) which retains KDEL-containing proteins in the ER lumen. To anchor anti-IL-10 in the cell membrane, sequences encoding a fragment of the hinge region of CD8a (hinge) and the transmembrane domain of CD28 (TM) were fused to the C-terminus of anti-IL-10S, resulting in anti-IL-10TM. Coding sequences were inserted under the control of the spleen focus forming virus (SFFV) promoter into pSIEW lentiviral transfer plasmid which also provides an enhanced green fluorescent protein (EGFP) encoding sequence as a marker gene, linked to the respective antibody sequence via an internal ribosome entry site (IRES). VSV-G pseudotyped lentiviral particles were generated and used for transduction of different types of immune effector cells including NK cells, T cells, B cells and cells of the monocyte/macrophage lineage, as well as CAR-engineered effector cells such as CAR NK cells. Successfully transduced cells were enriched by flow cytometric cell sorting of EGFP-positive cells and analyzed for expression of recombinant anti-IL-10S, anti-IL-10ER and anti-IL-10TM by immunoblot analysis of whole cell lysates or culture supernatants. Thereby intracellular expression of anti-IL-10 antibodies could be confirmed in NK cells (FIG. 2B), CAR-engineered NK cells (FIG. 2C), T cells (FIG. 3A), B cells (FIG. 3B) as well as in monocytes/macrophages (FIG. 3C) transduced with respective anti-IL-10 antibody encoding lentiviral vectors.

The data summarized in Example 2 demonstrate that anti-IL-10 antibodies can be directly expressed in various types of immune effector cells highly relevant for adoptive immunotherapy, including CAR-engineered variants thereof.

Example 3: Inhibition of IL-10 Production by Intracellular Expression of IL-10 Neutralizing Antibodies Next, the consequences of intracellular expression of recombinant anti-IL-10 antibodies on activation-induced IL-10 production by NK cells and CAR-engineered NK cells, and on constitutive IL-10 production by B cells were investigated. NK cells transduced with lentiviral vectors encoding anti-IL-10S, anti-IL-10ER or anti-IL-10TM were cultured for 6 hours either in the absence of target cells, or in the presence of NK-sensitive $K_562$ erythroleukemia cells at an E:T ratio of 1:1. Unmodified NK cells and $K_562$ cells kept in the absence of NK cells were included as controls. Culture supernatants were collected and secretion of IL-10 was measured using a cytometric bead array (CBA). While unmodified NK cells did not secrete large amounts of IL-10 in the absence of target cells, activation by contact with target cells strongly induced IL-10 production (FIG. 4A). Thereby the amount of IL-10 secreted into the culture supernatant was markedly reduced upon intracellular expression of anti-IL-10S, anti-IL-10ER or anti-IL-10TM, with anti-IL-10ER being most effective. Likewise, NK cells genetically engineered to express an ErbB2-specific CAR showed only marginal IL-10 secretion in the absence of target cells, while strong IL-10 production was induced by contact with ErbB2-expressing MDA-MB453 breast carcinoma cells. As observed with unmodified NK cells, expression of anti-IL-10S, anti-IL-10ER or anti-IL-10TM markedly reduced IL-10 secretion in the presence of target cells, with anti-IL-10ER again being most effective (FIG. 4B). To assess the effect of intracellular expression of recombinant anti-IL-m antibodies on constitutive IL-10 expression, Raji B-lymphoblastic cells were used as an example of IL-10-producing cells derived from the B-cell lineage. These cells continuously secrete high amounts of IL-10 into the culture medium, which was strongly inhibited by intracellular expression of anti-IL-10ER antibody (FIG. 4C).

The data summarized in Example 3 demonstrate that intracellular expression of anti-IL-m antibodies in various types of immune effector cells strongly inhibits activation-induced and constitutive IL-10 secretion.

Example 4: Silencing of IL-10 Expression by IL-10-Specific shRNA

Genetic modification of immune effector cells resulting in the expression of an IL-10-specific short hairpin (sh) RNA was investigated as an alternative means to reduce production of IL-10. shRNAs are artificial RNA molecules able to silence expression or inhibit translation of their target mRNA by RNA interference, resulting in the knockdown of target protein expression. To inhibit IL-10 expression, a commercially available lentiviral pGIPZ vector was used that encodes IL-10-specific shRNA (IL-10-specific region of the shRNA: 5'-UUCGUAUCUUCAUUGUCAU-3') together with green fluorescent protein (GFP) as a marker. A vector encoding an irrelevant shRNA was used as a control. VSV-G pseudotyped lentiviral particles were generated and used for transduction of NK cells and CAR-engineered NK cells as representative examples for immune effector cells relevant for adoptive cell therapy. Successfully transduced cells were enriched by flow cytometric cell sorting of GFP-positive cells. Untransduced NK cells, or NK cells transduced with lentiviral vectors encoding IL-10-specific shRNA (shRNA IL-10) or control shRNA (shRNA control) were stimulated with phorbol 12-myristate 13-acetate (PMA) and ionomycin (each at a concentration of 1 µg/mL) for 5 hours in the presence of GolgiPlug. Then whole cell lysates were prepared and analyzed for IL-10 by immunoblot analysis with IL-10-specific antibody. As expected, treatment with PMA/ionomycin resulted in strong activation-induced expression of IL-10 which was not affected by transduction of the NK cells with a control shRNA construct. In contrast, transduction of NK cells with the IL-10-specific shRNA vector resulted in marked reduction of IL-10 protein expression (FIG. 5A, upper panel). In a separate experiment, NK cells transduced with lentiviral vectors encoding IL-10-specific shRNA (shRNA IL-10) or control shRNA (shRNA control) were cultured for 6 hours either in the absence of target cells, or in the presence of NK-sensitive K562 erythroleukemia cells at an E:T ratio of 1:1. Unmodified NK cells and $K_{562}$ cells kept in the absence of NK cells were included as controls. Culture supernatants were collected and secretion of IL-10 was measured using a cytometric bead array (CBA). Unmodified NK cells did not secrete large amounts of IL-10 in the absence of target cells, whereas activation by contact with target cells strongly induced IL-10 production. While the amount of IL-10 secreted into the culture supernatant was not affected in cells transduced with the control shRNA construct, a marked reduction of IL-10 secretion was observed in activated NK cells expressing IL-10-specific shRNA (FIG. 5A, lower panel). Similar to unmodified NK cells, IL-10 production was specifically and strongly reduced in PMA/ionomycin-stimulated NK cells that were genetically engineered to express an ErbB2-specific CAR and IL-10-specific shRNA, while control shRNA did not affect expression of the cytokine in CAR NK cells (FIG. 5B, upper panel). Likewise, stimulation of ErbB2-specific CAR NK cells and CAR NK cells carrying a control shRNA construct by exposure to ErbB2-expressing MDA-MB453 breast carcinoma cells resulted in activation-induced secretion of high levels of IL-10, which was markedly reduced if CAR NK cells expressed IL-10-specific shRNA (FIG. 5B, lower panel).

The data summarized in Example 4 demonstrate that silencing of IL-10 expression by RNA interference strongly reduces IL-10 production in immune effector cells relevant for adoptive cell therapy.

Example 5: Downregulation of IL-10 Expression by CRISPR/Cas9-Mediated Gene Editing The clustered regularly interspaced short palindromic repeats-associated RNA-guided (CRISPR)/CRISPR associated protein (Cas) 9 system allows specific RNA-guided gene editing including the silencing of a gene of interest in mammalian cells. To downregulate IL-10 expression using the CRISPR/Cas9 system, IL-10-specific guide RNAs (gRNAs) were designed and incorporated into a lentiviral transfer vector also encoding Cas9 nuclease, a puromycin resistance gene and EGFP as a marker. A similar construct lacking a guide RNA served as a control. VSV-G pseudotyped lentiviral particles were generated and used for transduction of NK cells and CAR-engineered NK cells as representative examples for immune effector cells relevant for adoptive cell therapy. Successfully transduced cells were enriched by selection with puromycin, followed by flow cytometric cell sorting of EGFP-positive cells. Untransduced NK cells, or NK cells transduced with lentiviral vectors encoding Cas9 (Cas9), or Cas 9 together with IL-10-specific gRNA (IL-10 CRISPR/Cas9) were stimulated with PMA/ionomycin (each at a concentration of 1 µg/mL) for 5 hours in the presence of GolgiPlug. Then whole cell lysates were prepared and analyzed for IL-10 by immunoblot analysis with IL-10-specific antibody. As expected, treatment with PMA/ionomycin resulted in strong activation-induced expression of IL-10 which was not affected by transduction of the NK cells with a Cas9-encoding vector. In contrast, transduction of NK cells with a vector encoding Cas9 and IL-10-specific gRNA resulted in a loss of IL-10 protein expression (FIG. 6A, upper panel). In a separate experiment, NK cells transduced with lentiviral vectors encoding Cas9, or Cas9 together with IL-10-specific gRNA were cultured for 6 hours either in the absence of target cells, or in the presence of NK-sensitive K562 erythroleukemia cells at an E:T ratio of 1:1. Unmodified NK cells and K562 cells kept in the absence of NK cells were included as controls. Culture supernatants were collected and secretion of IL-10 was measured using a cytometric bead array (CBA). Unmodified NK cells did not secrete large amounts of IL-10 in the absence of target cells, whereas activation by contact with target cells strongly induced IL-10 production. While the amount of IL-10 secreted into the culture supernatant was not affected in cells expressing Cas9, no IL-10 secretion was observed in activated NK cells harboring a Cas9 construct together with IL-10-specific gRNA (FIG. 6A, lower panel). Similar to unmodified NK cells, IL-10 production was abolished in PMA/ionomycin-stimulated NK cells that were genetically engineered to express an ErbB2-specific CAR, Cas9 and IL-10-specific gRNA, while Cas9 expression alone did not affect IL-10 production in CAR NK cells (FIG. 6B, upper panel). Likewise, stimulation of ErbB2-specific CAR NK cells and CAR NK cells expressing Cas9 alone by exposure to ErbB2-expressing MDA-MB453 breast carcinoma cells resulted in activation-induced secretion of high levels of IL-10, which was abolished if CAR NK cells expressed Cas9 together with IL-10-specific gRNA (FIG. 6B, lower panel).

The data summarized in Example 5 demonstrate that targeted knockout of IL-10 expression by specific gene editing with the CRISPR/Cas9 nuclease system eliminates IL-10 production in immune effector cells relevant for adoptive cell therapy.

Example 6: Viability and Proliferation of Immune Effector Cells after Downregulation of IL-10 Production As demonstrated in the previous examples, different strategies including intracellular expression of anti-IL-10 antibodies (Examples 2, 3), shRNA-mediated gene silencing (Example 4) and CRISPR/Cas9-mediated gene knockout (Example 5) can be employed for genetic modification of immune effector cells to markedly reduce or eliminate IL-10 expression. To assess possible consequences of downregulation of IL-10 expression on the growth of such cells, cell proliferation was measured over a period of 7 days. NK cells genetically engineered to express an ErbB2-specific CAR together with an ER-retained anti-IL-10 antibody, IL-10-specific shRNA, or Cas9 nuclease and IL-10-specific guide RNA were used as representative examples of immune effector cells relevant for adoptive therapy. The cells were seeded in 24-well cell culture plates on day 0 at a cell density of $1.5 \times 10^5$ cells/mL, and cell growth was monitored by counting viable cells using trypan blue exclusion once per day for a period of 7 days. CAR NK cells with undisturbed IL-10 expression were included as controls. CAR NK cells modified by intracellular expression of anti-IL-10 antibody (anti-IL-10ER; FIG. 7A), expression of IL-10-specific shRNA (shRNA IL-10; FIG. 7B), or expression of Cas9 nuclease together with IL-10-specific guide RNA (IL-10 CRISPR/Cas9; FIG. 7C) displayed growth properties indistinguishable from CAR NK cells that were not modified by interference with IL-10 expression. Similar results were obtained with NK cells lacking CAR expression, but genetically engineered with intracellular anti-IL-10, shRNA IL-10, or IL-10 CRISPR/Cas9 (data not shown).

The data summarized in Example 6 demonstrate that inhibition of IL-10 production and activity by various means, including intracellular expression of an anti-IL-10 antibody, silencing of IL-10 expression by RNA interference and targeted knockout of IL-10 expression with the CRISPR/Cas9 system, has no negative effect on viability and proliferation of immune effector cells relevant for adoptive cell therapy.

Example 7: Antitumour Activity of Immune Effector Cells after Downregulation of IL-10 Production Downregulation of IL-10 production in adoptively transferred immune effector cells is intended to limit the inhibitory effects of this immunoregulatory cytokine on bystander immune cells without interfering with direct antitumour activity of the adoptively transferred cells. To assess possible consequences of downregulation of IL-10 expression on specific cytotoxicity and direct antitumour activity, CAR-mediated cytotoxicity of CAR engineered ErbB2-specific NK cells also expressing an ER-retained anti-IL-10 antibody, IL-10-specific shRNA, or Cas9 nuclease and IL-10-specific guide RNA against ErbB2-positive MDA-MB453 human breast carcinoma cells was tested in 2 hour co-culture assays at different E:T ratios. CAR NK cells with undisturbed IL-10 expression were included as controls. Thereby CAR NK cells modified by intracellular expression of anti-IL-10 antibody (anti-IL-10ER; FIG. 8A), expression of IL-10-specific shRNA (shRNA IL-10; FIG. 8B), or expression of Cas9 nuclease together with IL-10-specific guide RNA (IL-10 CRISPR/Cas9; FIG. 8C) retained high and specific CAR-mediated cytotoxicity indistinguishable from that of CAR NK cells that were not modified by interference with IL-10 expression. Similar results were obtained in co-culture cytotoxicity assays of NK-sensitive K562 erythroleukemia cells with NK cells lacking CAR expression, but genetically engineered with intracellular anti-IL-10, shRNA IL-10, or IL-10 CRISPR/Cas9 (data not shown).

The data summarized in Example 7 demonstrate that inhibition of IL-10 production and activity by various means, including intracellular expression of an anti-IL-10 antibody, silencing of IL-10 expression by RNA interference and targeted knockout of IL-10 expression with the CRISPR/Cas9 system, has no negative effect on direct antitumour activity of immune effector cells relevant for adoptive cell therapy.

Example 8: Downregulation of IL-10 Production in Immune Effector Cells Enhances Production of the Pro-Inflammatory Cytokine TNF-α

IL-10 inhibits the production of pro-inflammatory cytokines like IL-1β, IL-6, IL-12, G-CSF, GM-CSF and TNF-α in bystander immune cells. Also the bidirectional NK-DC crosstalk through IFN-γ, IL-12 and TNF-α to enhance T-cell priming can be significantly diminished by IL-10. To assess whether downregulation of IL-10 production in immune effector cells can modulate these cells' endogenous expression of pro-inflammatory cytokines such as TNF-α, NK cells genetically engineered to express an ErbB2-specific CAR together with anti-IL-10 antibodies or IL-10-specific shRNA were used as representative examples of immune effector cells relevant for adoptive therapy. CAR NK cells transduced with lentiviral vectors encoding anti-IL-10S, anti-IL-10ER, anti-IL-10TM or IL-10-specific shRNA were cultured for 6 hours either in the absence of target cells, or in the presence of ErbB2-expressing MDA-MB453 breast carcinoma cells at an E:T ratio of 1:1. CAR NK cells with undisturbed IL-10 expression including CAR NK cells carrying an irrelevant shRNA construct were included as controls. Culture supernatants were collected, and TNF-α levels were determined using a cytometric bead array. CAR-mediated activation of NK cells by ErbB2-positive target cells induced TNF-α secretion, which was further enhanced in CAR NK cells expressing ER-retained (anti-IL-10ER) or membrane-anchored anti-IL-10 antibody (anti-IL-10TM) (FIG. 9A). After activation with ErbB2-positive target cells also CAR NK cells expressing IL-10-specific shRNA displayed enhanced TNF-α production when compared to CAR NK cells with undisturbed IL-10 expression (FIG. 9B).

The data summarized in Example 8 demonstrate that inhibition of IL-10 production and activity by various means, including intracellular expression of anti-IL-10 antibodies and silencing of IL-10 expression by RNA interference can enhance the cells' endogenous production of the pro-inflammatory cytokine TNF-α, which is important for antitumour activity of bystander immune cells including the maturation of professional antigen presenting cells and other mechanisms that support the induction of an adaptive antitumour immune response.

Example 9: Downregulation of IL-10 Production in Immune Effector Cells Prevents Polarization of Bystander Macrophages Towards a Tumour-Promoting M2 Phenotype Tumour-associated macrophages (TAMs) are one of the most abundant and crucial non-neoplastic cells in the tumour microenvironment. TAMs are primarily polarized towards tumour-promoting M2 subsets with polarization into tumour-suppressive M1 macrophages being only rarely observed. This imbalance in macrophage polarization is a major contributor to maintaining a tumour-promoting environment. To assess whether downregulation of IL-10 production modulates polarization of bystander macrophages, NK cells genetically engineered to express an ErbB2-specific CAR together with an intracellular anti-IL-10 antibody (anti-IL-10ER) were used as a representative example of immune effector cells relevant for adoptive therapy. Human monocyte-derived macrophages from healthy donors were used in a transwell assay, with macrophages cultured in the bottom chamber, separated by a membrane with a pore size of 0.4 μm from co-cultured CAR NK cells kept in the upper chamber. CAR NK cells co-expressing anti-IL-10ER were either kept alone, or co-cultured in the upper chamber with ErbB2-expressing MDA-MB453 breast carcinoma cells at an E:T ratio of 1:1 to induce CAR-mediated activation of the NK cells. Unmodified NK cells without CAR and anti-IL-10ER expression and CAR NK cells without anti-IL10ER expression were included as controls. For comparison, macrophages cultured in the absence of NK cells were treated with IFN-γ and lipopolysaccharide (LPS), known to induce polarization towards an M1-like phenotype. After 24 hours, macrophages were harvested and polarization was investigated by assessing the levels of surface markers distinguishing M1-like and M2-like subpopulations (HLA-DR and CD86: high in M1, low in M2; CD163: low in M1, high in M2). In the presence of target tumour cells, CAR-mediated activation of CAR NK cells resulted in a downregulation of the M1 markers HLA-DR and CD86 in co-cultured macrophages (FIG. 10A, B), and upregulation of the M2 marker CD163 (FIG. 10C), indicating that activated CAR NK cells shift the balance towards a tumour-promoting M2-like phenotype of bystander macrophages. If activation-induced production of IL-10 in CAR NK cells was prevented by intracellular expression of ER-retained anti-IL-10 antibody, the M1 markers HLA-DR and CD86 were upregulated, while the M2 marker CD163 was downregulated in comparison to CAR NK cells without anti-IL-10ER expression. Levels of the M1 markers HLA-DR and CD86 reached those of IFN-γ/LPS-treated macrophages, demonstrating that downregulation of IL-10 secretion in activated CAR NK cells neutralized their M2-promoting effect, instead inducing polarization of co-cultured macrophages towards a tumour-suppressive M1-like phenotype.

The data summarized in Example 9 demonstrate that the therapeutic efficacy of immune effector cells for adoptive cell therapy can be limited by promoting polarization of bystander macrophages towards a tumour-promoting M2 phenotype. If IL-10 production or secretion in the immune effector cells is downregulated, this effect is reversed and polarization of macrophages is shifted towards a tumour-suppressive M1-like phenotype, expected to enhance therapeutic efficacy of adoptive cell therapy.

Example 10: Intracellular Expression of IL-6-Neutralizing Antibodies

Similar to IL-10, interleukin-6 (IL-6) is an important endogenous regulator of immunity in immune effector cells, also influencing the activity of bystander immune cells (Fisher et al., Semin Immunol 26: 38-47, 2014). Following an approach similar to the one described for anti-IL-10 antibodies in Example 2, the inventors designed recombinant anti-IL-6 antibodies for direct expression in immune effector cells to block IL-6 activity in the extracellular space (secreted anti-IL-6; anti-IL-6S), prevent secretion of endogenously synthesized IL-6 by inhibiting its transport to the cell surface (endoplasmic reticulum-retained anti-IL-6; anti-IL-6ER), or trap IL-6 on the cell surface (transmembrane anti-IL-6; anti-IL-6TM) (Figure ii). Anti-IL-6S consists of an N-terminal immunoglobulin heavy chain signal peptide for direction into the secretory pathway, a codon-optimized scFv fragment of humanized anti-IL-6 antibody olokizumab (Shaw et al. mAbs 6: 774-782, 2014), and a peptide derived from human influenza virus hemagglutinin (HA-tag) for immunological detection (FIG. 11A). Anti-IL-6ER in addition contains a C-terminal KDEL peptide sequence for binding to the KDEL receptor in the endoplasmic reticulum (ER) which retains KDEL-containing proteins in the ER lumen. To anchor anti-IL-6 in the cell membrane, sequences encoding a fragment of the hinge region of CD8a (hinge) and the transmembrane domain of CD28 (TM) were fused to the C-terminus of anti-IL-6S, resulting in anti-IL-6TM. Coding sequences were inserted under the control of the spleen focus forming virus (SFFV) promoter into pSIEW lentiviral transfer plasmid which also provides an enhanced green fluorescent protein (EGFP) encoding sequence as a marker gene, linked to the respective antibody sequence via an internal ribosome entry site (IRES). VSV-G pseudotyped lentiviral particles were generated and used for transduction of different types of immune effector cells including NK cells and cells of the monocyte/macrophage lineage, as well as CAR-engineered effector cells such as CAR NK cells. Successfully transduced cells were enriched by flow cytometric cell sorting of EGFP-positive cells and analyzed for expression of recombinant anti-IL-6S and anti-IL-6ER by immunoblot analysis of whole cell lysates. Thereby intracellular expression of anti-IL-6 antibodies could be confirmed in NK cells (FIG. 11B), CAR-engineered NK cells (FIG. 11C) as well as in monocytes/macrophages (FIG. 11D) transduced with respective anti-IL-6 antibody encoding lentiviral vectors.

The data summarized in Example 10 demonstrate that anti-IL-6 antibodies can be engineered like anti-IL-10 antibodies in different formats and directly be expressed in various types of immune effector cells highly relevant for adoptive immunotherapy, including CAR-engineered variants thereof.

Example 11: Co-Expression of IL-10-Neutralizing Antibodies and Pro-inflammatory Cytokines IL-12 and IL-15 are important pro-inflammatory cytokines with therapeutic potential for the treatment of cancer (see Floros & Tarhini, Semin Oncol 42: 539-548, 2015). To demonstrate the feasibility of co-expression of an inhibitor of an endogenous regulator of immunity in immune effector cells such as ER-retained anti-IL-10 antibody (anti-IL-10ER) with pro-inflammatory cytokines such as IL-12 or IL-15, the inventors designed lentiviral constructs for simultaneous expression of anti-IL-10ER and either IL-15 hyper-agonist (FIG. 12A) or single chain IL-12 (FIG. 12B), following an approach similar to the one outlined for anti-IL-10 antibodies in Example 2. IL-15 hyper-agonist is a fusion of the sushi domain of IL-15 receptor α-chain (IL-15Rα) to an IL-15 mutein in which the asparagine residue at position 72 of IL-15 is exchanged with an aspartic acid residue. Single chain IL-12 is a fusion protein combining the P40 and P35 subunits of IL-12 into a single protein with IL-12 activity. The coding sequences of anti-IL-10ER, the P2A self-cleaving 2A peptide from porcine teschovirus-1, and either IL-15 hyper-agonist or single chain IL-12 were fused into a single open reading frame either in the orientation anti-IL-10ER-P2A-cytokine (FIG. 12A, B, upper panels) or cytokine-P2A-anti-IL-10ER (FIG. 12A, B, lower panels) and inserted under the control of the spleen focus forming virus (SFFV) promoter into pSIEW lentiviral transfer plasmid. VSV-G pseudotyped lentiviral particles were generated and used for transduction of different types of immune effector cells including NK cells (FIG. 12C) and CAR-engineered effector cells such as CAR NK cells (FIG. 12D).

The data summarized in Example 11 demonstrate that an anti-IL-10 antibody can be combined with the pro-inflammatory cytokines IL-15 hyper-agonist or single chain IL-12 for co-expression in various types of immune effector cells highly relevant for adoptive immunotherapy, including CAR-engineered variants thereof. Thereby simultaneously inhibiting in a target immune effector cell the expression, function, stability or secretion of an endogenously expressed regulator of immunity as achieved here by expressing an anti-IL-10 antibody, and providing the same immune effector cell with an activator and/or agonist not naturally expressed by said immune effector cell such as a pro-inflammatory cytokine like IL-15 hyper-agonist or single chain IL-12, can enhance the immunological activity of the target immune effector cell even more strongly than only inhibiting an endogenously expressed regulator of immunity.

Example 12: Inhibition of the Activity of NK-Cell-Derived IL-10 by a Recombinant Tetravalent Anti-IL-10 Antibody Prevents Polarization of Macrophages Towards a Tumour-Promoting M2 Phenotype The imbalance in macrophage polarization is a major contributor to maintaining a tumour-promoting environment, with tumour-associated macrophages primarily being polarized towards tumour-promoting M2 subsets. To assess whether inhibition of the activity of secreted IL-10 modulates polarization of bystander macrophages, NK cells genetically engineered to express an ErbB2-specific CAR as a representative example of immune effector cells relevant for adoptive therapy were exposed to the tetravalent anti-IL-10 antibody from Example 1. Human monocyte-derived macrophages from healthy donors were used in a transwell assay, with macrophages cultured in the bottom chamber, separated by a membrane with a pore size of 0.4 μm from co-cultured CAR NK cells kept in the upper chamber. CAR NK cells were either kept alone in the absence or presence of 2 μg/mL of tetravalent anti-IL-10 antibody or an isotype-matched IgG4-Fc control protein, or co-cultured in the upper chamber in the absence or presence of tetravalent anti-IL-10 antibody or the IgG4-Fc control protein with ErbB2-expressing MDA-MB453 breast carcinoma cells at an E:T ratio of 1:1 to induce CAR-mediated activation of the NK cells. Unmodified NK cells without CAR expression were included as control. For comparison, macrophages cultured in the absence of NK cells were treated with IFN-γ and lipopolysaccharide (LPS), known to induce polarization towards an M1-like phenotype. After 24 hours, macrophages were harvested and polarization was investigated by assessing the levels of surface markers distinguishing M1-like and M2-like subpopulations (HLA-DR and CD86: high in M1, low in M2; CD163: low in M1, high in M2). In the presence of target tumour cells, CAR-mediated activation of CAR NK cells resulted in a downregulation of the M1 markers HLA-DR and CD86 in co-cultured macrophages (FIG. 13A, B), and upregulation of the M2 marker CD163 (FIG. 13C), indicating that activated CAR NK cells shift the balance towards a tumour-promoting M2-like phenotype of bystander macrophages. If the activity of IL-10 secreted by activated CAR NK cells was inhibited by tetravalent anti-IL-10 antibody, the M1 markers HLA-DR and CD86 were upregulated, while the M2 marker CD163 was downregulated in comparison to CAR NK cells kept without antibody or in the presence of isotype-matched IgG4-Fc control protein. Levels of the M1 markers HLA-DR and CD86 were similar to those of IFN-γ/LPS-treated macrophages, demonstrating that inhibition of CAR NK cell-derived IL-10 neutralized their M2-promoting effect, instead inducing polarization of co-cultured macrophages towards a tumour-suppressive M1-like phenotype.

The data summarized in Example 12 confirm that the therapeutic efficacy of immune effector cells for adoptive cell therapy can be limited by promoting polarization of bystander macrophages towards a tumour-promoting M2 phenotype. If the activity of IL-10 secreted by the immune effector cells is inhibited, this effect is reversed and polarization of macrophages is shifted towards a tumour-suppressive M1-like phenotype, expected to enhance therapeutic efficacy of adoptive cell therapy.

Example 13: Downregulation of IL-10 Production in Immune Effector Cells Enhances Maturation of Bystander Dendritic Cells Dendritic cells (DCs) are crucial for uptake and presentation of tumour antigens to T cells, thereby facilitating T-cell activation and subsequent T-cell-mediated antitumour activity. A prerequisite for effective antigen presentation to T cells is maturation of DCs from an immature state to mature DCs, which are characterized by enhanced expression of costimulatory and major histocompatibility complex molecules. To assess whether downregulation of IL-10 production modulates maturation of bystander DCs, NK cells genetically engineered to express an ErbB2-specific CAR together with an intracellular anti-IL-10 antibody (anti-IL-10ER) were used as a representative example of immune effector cells relevant for adoptive therapy. Immature human monocyte-derived dendritic cells (iDCs) from healthy donors were used in a transwell assay, with iDCs cultured in the bottom chamber, separated by a membrane with a pore size of 0.4 μm from co-cultured CAR NK cells kept in the upper chamber. CAR NK cells co-expressing anti-IL-10ER were either kept alone, or co-cultured in the upper chamber with ErbB2-expressing MDA-MB453 breast carcinoma cells at an E:T ratio of 1:1 to induce CAR-mediated activation of the NK cells. Unmodified NK cells without CAR and anti-IL-10ER expression and CAR NK cells without anti-IL-10ER expression were included as controls. For comparison, iDCs were cultured in the absence of NK cells with TNF-α, IL-1β, IL-6 and prostaglandin E2, known to induce DC maturation. After 24 hours, DCs were harvested and DC maturation was investigated by assessing the levels of surface markers distinguishing immature and mature DC subpopulations (HLA-DR, CD86 and CD83: high in mature DCs, low in immature DCs). In the presence of target tumour cells, CAR-mediated activation of CAR NK cells resulted in a slight upregulation of the DC maturation markers HLA-DR and CD86 (FIG. 14A, B) but not CD83 (FIG. 14C) in co-cultured DCs, indicating that activated CAR NK cells can induce DC maturation to a limited extent. If activation-induced production of IL-10 in CAR NK cells was prevented by intracellular expression of ER-retained anti-IL-10 antibody, upregulation of HLA-DR and CD86 was further enhanced and also the maturation marker CD83 was upregulated. The level of HLA-DR even reached that of DCs treated with TNF-α, IL-1β, IL-6 and prostaglandin E2, demonstrating that downregulation of IL-10 secretion in activated CAR NK cells strongly enhanced their ability to induce maturation of co-cultured dendritic cells.

The data summarized in Example 13 demonstrate that immune effector cells for adoptive cell therapy can induce maturation of bystander dendritic cells towards a more mature phenotype. If IL-10 secretion in the immune effector cells is downregulated, this effect is strongly enhanced and maturation of dendritic cells is markedly increased, expected to enhance therapeutic efficacy of adoptive cell therapy.

Example 14: Inhibition of IL-6 Production by Intracellular Expression of IL-6-Neutralizing Antibodies The consequences of intracellular expression of the recombinant anti-IL-6 antibodies described in Example m on activation-induced IL-6 production by macrophages/monocytes, and on constitutive IL-6 production by breast carcinoma cells were investigated. Macrophages/monocytes transduced with lentiviral vectors encoding anti-IL-6S or anti-IL-6ER were cultured for 16 hours in medium containing 100 ng/mL LPS to induce IL-6 expression. Macrophages/monocytes kept in the absence of LPS were included as controls. Likewise, MDA-MB468 breast carcinoma cells which constitutively secrete IL-6 were transduced with lentiviral vectors encoding anti-IL-6S or anti-IL-6ER. Successfully transduced cells were enriched as described in Example 10 for macrophages/monocytes, and cultured in fresh medium for 6 hours. Untransduced MDA-MB468 cells served as control. Culture supernatants from macrophages/monocytes and breast carcinoma cells were collected and secretion of IL-6 was measured using a cytometric bead array (CBA). While resting macrophages/monocytes did not secrete measurable amounts of IL-6, activation with LPS strongly induced IL-6 production (FIG. 15A). The amount of IL-6 secreted into the culture supernatant was markedly reduced upon intracellular expression of anti-IL-6S or anti-IL-6ER.

Likewise, constitutive secretion of IL-6 by MDA-MB468 cells was markedly reduced by expression of anti-IL-10S or anti-IL-10ER (FIG. 15B).

The data summarized in Example 14 demonstrate that intracellular expression of anti-IL-6 antibodies in immune effector cells and tumor cells strongly inhibits activation-induced and constitutive IL-6 secretion.

The invention claimed is:

1. A method for enhancing the immunological activity of a target immune effector cell, the method comprising the steps of:
   (a) Providing the target immune effector cell,
   (b) Inhibiting in said target immune effector cell the expression, function, stability, or secretion of one or more endogenously expressed regulators of immunity of said target immune effector cell,
      wherein said one or more endogenously expressed regulators of immunity of said target immune effector cell is at least one of IL-6 or IL-10, and
      step (b) comprises:
         the use of an inhibitory antibody specific to said one or more endogenously expressed regulators of immunity, wherein the inhibitory antibody is an antibody according to or encoded by any one of SEQ ID Nos. 1 to 8 or 13 to 18.

2. The method according to claim 1, wherein the target immune effector cell is selected from a monocytic cell, macrophage, dendritic cell, B cell, T cell, NK cell, or NKT cell.

3. The method according to claim 1, wherein step (b) comprises bringing into contact the target immune effector cell with the inhibitory antibody specific to of said one or more endogenously expressed regulators of immunity.

4. The method according to claim 1, wherein in step (b) the inhibiting comprises expression of the inhibitory antibody specific to said one or more endogenously expressed regulators of immunity within the target immune effector cell, and wherein said inhibitory antibody when expressed impairs within the cell it is expressed, the expression, function, stability, or secretion of said one or more endogenously expressed regulators of immunity of said target immune effector cell.

5. The method according to claim 1, further comprising a step of bringing into contact the target immune effector cell with an activator and/or agonist of immune function of the target immune effector cell, wherein the activator and/or agonist of immune function is an agonist of IL-15.

6. The method according to claim 5, wherein the agonist of IL-15 is IL-15 hyper-agonist.

7. The method according to claim 6, wherein the method comprises a co-expression in said target immune effector cell of an anti-IL-10 antibody and the agonist of IL-15.

8. The method according to claim 1, wherein the target immune effector cell is a genetically engineered target immune effector cell.

9. The method according to claim 8, wherein the genetically engineered target immune effector cell comprises an effector genetic construct for the expression of a tumor targeting molecule.

10. The method according to claim 1, wherein the target immune effector cell is a chimeric antigen receptor natural killer (CAR NK) cell.

* * * * *

SEQUENCE LISTING

<160> NUMBER OF SEQ ID NOS: 29

<210> SEQ ID NO 1
<211> LENGTH: 2235
<212> TYPE: DNA
<213> ORGANISM: artificial
<220> FEATURE:
<223> OTHER INFORMATION: anti-IL-10 mini-antibody DNA

<400> SEQUENCE: 1

| | | | | | |
|---|---|---|---|---|---|
| atggactgga | tctggcgcat | cctgtttctc | gtgggagccg | ccacaggcgc | ccactctgaa | 60 |
| gtgcagctgg | tggaatctgg | cggcggactg | gtgcagcctg | gcggatctct | gagactgagc | 120 |
| tgtgccgcca | gcggcttcag | ctttgccaca | tacggcgtgc | actgggtgcg | ccagagccct | 180 |
| ggaaaaggcc | tggaatggct | gggagtgatc | tggcggggag | cagcacaga | ttacagcgcc | 240 |
| gccttcatga | ccggctgac | catcagcaag | acaacagca | gaacaccgt | gtacctgcag | 300 |
| atgaacagcc | tgcgggccga | ggataccgcc | gtgtacttct | gtgccaagca | ggcctacggc | 360 |
| cactacatgg | actattgggg | ccagggcacc | agcgtgaccg | tgtctagcgg | aggcggagga | 420 |
| tcaggcggcg | gaggaagtgg | cggagggga | tctgatgtcg | tgatgaccca | gagcccctg | 480 |
| agcctgcctg | tgacactggg | acagcctgcc | agcatcagct | gccggtccag | ccagaacatc | 540 |
| gtgcacagca | acggcaacac | ctatctggaa | tggtatctgc | agcggcctgg | ccagtccccc | 600 |
| agactgctga | tctacaaggt | gtccaaccgg | ttcagcggcg | tgcccgacag | attttctggc | 660 |
| tctggcagcg | gcaccgactt | caccctgaag | atctcccggg | tggaagccga | ggacgtgggc | 720 |
| gtgtactact | gttttcaagg | cagccacgtg | ccctggacct | tcggccaggg | aacaaaggtg | 780 |
| gaaatcaagg | ctagcgttag | atctcccca | tgcccatcat | gcccagcacc | tgagttcctg | 840 |
| ggggaccat | cagtcttcct | gttcccccca | aaacccaagg | acactctcat | gatctcccgg | 900 |
| acccctgagg | tcacgtgcgt | ggtggtggac | gtgagccagg | aagacccga | ggtccagttc | 960 |
| aactggtacg | tggatggcgt | ggaggtgcat | aatgccaaga | caaagccgcg | ggaggagcag | 1020 |
| ttcaacagca | cgtaccgtgt | ggtcagcgtc | ctcaccgtcc | tgcaccagga | ctggctgaac | 1080 |
| ggcaaggagt | acaagtgcaa | ggtctccaac | aaaggcctcc | cgtcctccat | cgagaaaacc | 1140 |
| atctccaaag | ccaaagggca | gccccgagag | ccacaggtgt | acaccctgcc | cccatcccag | 1200 |
| gaggagatga | ccaagaacca | ggtcagcctg | acctgcctgg | tcaaaggctt | ctaccccagc | 1260 |
| gacatcgccg | tggagtggga | gagcaatggg | cagccggaga | caactacaa | gaccacgcct | 1320 |
| cccgtgctgg | actccgacgg | ctccttcttc | ctctacagca | ggctaaccgt | ggacaagagc | 1380 |
| aggtggcagg | aggggaatgt | cttctcatgc | tccgtgatgc | atgaggctct | gcacaaccac | 1440 |
| tacacacaga | agagcctctc | cctgtctctg | ggtaaaggat | ccggcggagg | aacaagcgga | 1500 |
| gaagtgcagc | tggtggaatc | tggcggcgga | ctggtgcagc | ctggcggatc | tctgagactg | 1560 |
| agctgtgccg | ccagcggctt | cagctttgcc | acatacggcg | tgcactgggt | gcgccagagc | 1620 |
| cctggaaaag | gcctggaatg | gctgggagtg | atctggcggg | gaggcagcac | agattacagc | 1680 |
| gccgccttca | tgaccggct | gaccatcagc | aaggacaaca | gcaagaacac | cgtgtacctg | 1740 |
| cagatgaaca | gcctgcgggc | cgaggatacc | gccgtgtact | ctgtgccaa | gcaggcctac | 1800 |
| ggccactaca | tggactattg | gggccagggc | accagcgtga | ccgtgtctag | cggaggcgga | 1860 |
| ggatcaggcg | gcgaggaag | tggcggaggg | ggatctgatg | tcgtgatgac | ccagagcccc | 1920 |
| ctgagcctgc | ctgtgacact | gggacagcct | gccagcatca | gctgccggtc | agccagaac | 1980 |
| atcgtgcaca | gcaacggcaa | cacctatctg | gaatggtatc | tgcagcggcc | tggccagtcc | 2040 |

```
cccagactgc tgatctacaa ggtgtccaac cggttcagcg gcgtgcccga cagattttct   2100
ggctctggca gcggcaccga cttcaccctg aagatctccc gggtggaagc cgaggacgtg   2160
ggcgtgtact actgttttca aggcagccac gtgccctgga ccttcggcca gggaacaaag   2220
gtggaaatca agtag                                                    2235
```

```
<210> SEQ ID NO 2
<211> LENGTH: 744
<212> TYPE: PRT
<213> ORGANISM: artificial
<220> FEATURE:
<223> OTHER INFORMATION: anti-IL-10 mini-antibody protein

<400> SEQUENCE: 2
```

```
Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ala Thr Tyr Gly Val His Trp Val Arg Gln Ser Pro Gly Lys Gly Leu
    50                  55                  60

Glu Trp Leu Gly Val Ile Trp Arg Gly Gly Ser Thr Asp Tyr Ser Ala
65                  70                  75                  80

Ala Phe Met Ser Arg Leu Thr Ile Ser Lys Asp Asn Ser Lys Asn Thr
                85                  90                  95

Val Tyr Leu Gln Met Asn Ser Leu Arg Ala Glu Asp Thr Ala Val Tyr
            100                 105                 110

Phe Cys Ala Lys Gln Ala Tyr Gly His Tyr Met Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Asp Val Val Met Thr Gln Ser Pro Leu
145                 150                 155                 160

Ser Leu Pro Val Thr Leu Gly Gln Pro Ala Ser Ile Ser Cys Arg Ser
                165                 170                 175

Ser Gln Asn Ile Val His Ser Asn Gly Asn Thr Tyr Leu Glu Trp Tyr
            180                 185                 190

Leu Gln Arg Pro Gly Gln Ser Pro Arg Leu Leu Ile Tyr Lys Val Ser
        195                 200                 205

Asn Arg Phe Ser Gly Val Pro Asp Arg Phe Ser Gly Ser Gly Ser Gly
    210                 215                 220

Thr Asp Phe Thr Leu Lys Ile Ser Arg Val Glu Ala Glu Asp Val Gly
225                 230                 235                 240

Val Tyr Tyr Cys Phe Gln Gly Ser His Val Pro Trp Thr Phe Gly Gln
                245                 250                 255

Gly Thr Lys Val Glu Ile Lys Ala Ser Val Arg Ser Pro Pro Cys Pro
            260                 265                 270

Ser Cys Pro Ala Pro Glu Phe Leu Gly Gly Pro Ser Val Phe Leu Phe
        275                 280                 285

Pro Pro Lys Pro Lys Asp Thr Leu Met Ile Ser Arg Thr Pro Glu Val
    290                 295                 300

Thr Cys Val Val Val Asp Val Ser Gln Glu Asp Pro Glu Val Gln Phe
305                 310                 315                 320
```

```
Asn Trp Tyr Val Asp Gly Val Glu Val His Asn Ala Lys Thr Lys Pro
                    325                 330                 335

Arg Glu Glu Gln Phe Asn Ser Thr Tyr Arg Val Val Ser Val Leu Thr
            340                 345                 350

Val Leu His Gln Asp Trp Leu Asn Gly Lys Glu Tyr Lys Cys Lys Val
        355                 360                 365

Ser Asn Lys Gly Leu Pro Ser Ser Ile Glu Lys Thr Ile Ser Lys Ala
370                 375                 380

Lys Gly Gln Pro Arg Glu Pro Gln Val Tyr Thr Leu Pro Pro Ser Gln
385                 390                 395                 400

Glu Glu Met Thr Lys Asn Gln Val Ser Leu Thr Cys Leu Val Lys Gly
            405                 410                 415

Phe Tyr Pro Ser Asp Ile Ala Val Glu Trp Glu Ser Asn Gly Gln Pro
        420                 425                 430

Glu Asn Asn Tyr Lys Thr Thr Pro Pro Val Leu Asp Ser Asp Gly Ser
435                 440                 445

Phe Phe Leu Tyr Ser Arg Leu Thr Val Asp Lys Ser Arg Trp Gln Glu
    450                 455                 460

Gly Asn Val Phe Ser Cys Ser Val Met His Glu Ala Leu His Asn His
465                 470                 475                 480

Tyr Thr Gln Lys Ser Leu Ser Leu Ser Leu Gly Lys Gly Ser Gly Gly
            485                 490                 495

Gly Thr Ser Gly Glu Val Gln Leu Val Glu Ser Gly Gly Gly Leu Val
        500                 505                 510

Gln Pro Gly Gly Ser Leu Arg Leu Ser Cys Ala Ala Ser Gly Phe Ser
    515                 520                 525

Phe Ala Thr Tyr Gly Val His Trp Val Arg Gln Ser Pro Gly Lys Gly
530                 535                 540

Leu Glu Trp Leu Gly Val Ile Trp Arg Gly Gly Ser Thr Asp Tyr Ser
545                 550                 555                 560

Ala Ala Phe Met Ser Arg Leu Thr Ile Ser Lys Asp Asn Ser Lys Asn
            565                 570                 575

Thr Val Tyr Leu Gln Met Asn Ser Leu Arg Ala Glu Asp Thr Ala Val
        580                 585                 590

Tyr Phe Cys Ala Lys Gln Ala Tyr Gly His Tyr Met Asp Tyr Trp Gly
    595                 600                 605

Gln Gly Thr Ser Val Thr Val Ser Ser Gly Gly Gly Gly Ser Gly Gly
            610                 615                 620

Gly Gly Ser Gly Gly Gly Gly Ser Asp Val Val Met Thr Gln Ser Pro
625                 630                 635                 640

Leu Ser Leu Pro Val Thr Leu Gly Gln Pro Ala Ser Ile Ser Cys Arg
            645                 650                 655

Ser Ser Gln Asn Ile Val His Ser Asn Gly Asn Thr Tyr Leu Glu Trp
        660                 665                 670

Tyr Leu Gln Arg Pro Gly Gln Ser Pro Arg Leu Leu Ile Tyr Lys Val
    675                 680                 685

Ser Asn Arg Phe Ser Gly Val Pro Asp Arg Phe Ser Gly Ser Gly Ser
690                 695                 700

Gly Thr Asp Phe Thr Leu Lys Ile Ser Arg Val Glu Ala Glu Asp Val
705                 710                 715                 720

Gly Val Tyr Tyr Cys Phe Gln Gly Ser His Val Pro Trp Thr Phe Gly
            725                 730                 735

Gln Gly Thr Lys Val Glu Ile Lys
```

<210> SEQ ID NO 3
<211> LENGTH: 831
<212> TYPE: DNA
<213> ORGANISM: artificial
<220> FEATURE:
<223> OTHER INFORMATION: anti-IL-10ER DNA

<400> SEQUENCE: 3

| | | | | | |
|---|---|---|---|---|---|
| atggactgga | tttggcggat | cctgttcctc | gtgggagccg | ccacaggcgc | ccattctgaa | 60 |
| gtgcagctgg | tggaatctgg | cggcggactg | gtgcagcctg | gcggatctct | gagactgagc | 120 |
| tgtgccgcca | gcggcttcag | ctttgccaca | tacggcgtgc | actgggtgcg | gcagagccct | 180 |
| gggaaaggcc | tggaatggct | gggagtgatc | tggcggggag | gcagcacaga | ttacagcgcc | 240 |
| gccttcatga | gccggctgac | catcagcaag | gacaacagca | agaacaccgt | gtacctgcag | 300 |
| atgaacagcc | tgcgggccga | ggataccgcc | gtgtacttct | gtgccaagca | ggcctacggc | 360 |
| cactacatgg | actattgggg | ccagggcacc | agcgtgaccg | tgtctagcgg | aggcggagga | 420 |
| tcaggcggcg | gaggaagtgg | cggagggggga | tctgatgtcg | tgatgaccca | gagccccctg | 480 |
| agcctgcctg | tgacactggg | acagcctgcc | agcatcagct | gccggtccag | ccagaacatc | 540 |
| gtgcacagca | acggcaacac | ctatctggaa | tggtatctgc | agcggcctgg | ccagtccccc | 600 |
| agactgctga | tctacaaggt | gtccaaccgg | ttcagcggcg | tgcccgacag | attttctggc | 660 |
| tctggcagcg | gcaccgactt | caccctgaag | atctcccggg | tggaagccga | ggacgtgggc | 720 |
| gtgtactact | gttttcaagg | cagccacgtg | ccctggacct | tcggccaggg | aacaaaggtg | 780 |
| gaaatcaagt | accccctacga | cgtgcccgat | tacgccaagg | acgagctgtg | a | 831 |

<210> SEQ ID NO 4
<211> LENGTH: 276
<212> TYPE: PRT
<213> ORGANISM: artificial
<220> FEATURE:
<223> OTHER INFORMATION: anti-IL-10ER protein

<400> SEQUENCE: 4

Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ala Thr Tyr Gly Val His Trp Val Arg Gln Ser Pro Gly Lys Gly Leu
    50                  55                  60

Glu Trp Leu Gly Val Ile Trp Arg Gly Gly Ser Thr Asp Tyr Ser Ala
65                  70                  75                  80

Ala Phe Met Ser Arg Leu Thr Ile Ser Lys Asp Asn Ser Lys Asn Thr
                85                  90                  95

Val Tyr Leu Gln Met Asn Ser Leu Arg Ala Glu Asp Thr Ala Val Tyr
            100                 105                 110

Phe Cys Ala Lys Gln Ala Tyr Gly His Tyr Met Asp Tyr Trp Gly Gln
        115                 120                 125

Gly Thr Ser Val Thr Val Ser Ser Gly Gly Gly Gly Ser Gly Gly Gly
    130                 135                 140

Gly Ser Gly Gly Gly Gly Ser Asp Val Val Met Thr Gln Ser Pro Leu
145                 150                 155                 160

```
Ser Leu Pro Val Thr Leu Gly Gln Pro Ala Ser Ile Ser Cys Arg Ser
            165                 170                 175

Ser Gln Asn Ile Val His Ser Asn Gly Asn Thr Tyr Leu Glu Trp Tyr
        180                 185                 190

Leu Gln Arg Pro Gly Gln Ser Pro Arg Leu Leu Ile Tyr Lys Val Ser
    195                 200                 205

Asn Arg Phe Ser Gly Val Pro Asp Arg Phe Ser Gly Ser Gly Ser Gly
210                 215                 220

Thr Asp Phe Thr Leu Lys Ile Ser Arg Val Glu Ala Glu Asp Val Gly
225                 230                 235                 240

Val Tyr Tyr Cys Phe Gln Gly Ser His Val Pro Trp Thr Phe Gly Gln
                245                 250                 255

Gly Thr Lys Val Glu Ile Lys Tyr Pro Tyr Asp Val Pro Asp Tyr Ala
            260                 265                 270

Lys Asp Glu Leu
        275

<210> SEQ ID NO 5
<211> LENGTH: 819
<212> TYPE: DNA
<213> ORGANISM: artificial
<220> FEATURE:
<223> OTHER INFORMATION: anti-IL-10S DNA

<400> SEQUENCE: 5
atggactgga tttggcggat cctgttcctc gtgggagccg ccacaggcgc ccattctgaa      60
gtgcagctgg tggaatctgg cggcggactg gtgcagcctg gcggatctct gagactgagc     120
tgtgccgcca gcggcttcag cttttgccaca tacggcgtgc actgggtgcg gcagagccct    180
gggaaaggcc tggaatggct gggagtgatc tggcggggag gcagcacaga ttacagcgcc    240
gccttcatga ccggctgac catcagcaag gacaacagca gaacaccgt gtacctgcag      300 atgaacagcc tgcgggccga ggataccgcc gtgtacttct gtgccaagca ggcctacggc    360
cactacatgg actattgggg ccagggcacc agcgtgaccg tgtctagcgg aggcggagga    420
tcaggcggcg gaggaagtgg cggagggga tctgatgtcg tgatgaccca gagccccctg     480
agcctgcctg tgacactggg acagcctgcc agcatcagct gccggtccag ccagaacatc    540
gtgcacagca acggcaacac ctatctggaa tggtatctgc agcggcctgg ccagtccccc    600
agactgctga tctacaaggt gtccaaccgg ttcagcggcg tgcccgacag attttctggc    660
tctggcagcg gcaccgactt caccctgaag atctcccggg tggaagccga ggacgtgggc    720
gtgtactact gttttcaagg cagccacgtg ccctggacct tcggccaggg aacaaaggtg    780
gaaatcaagt accctacga cgtgcccgat tacgcctga                             819

<210> SEQ ID NO 6
<211> LENGTH: 272
<212> TYPE: PRT
<213> ORGANISM: artificial
<220> FEATURE:
<223> OTHER INFORMATION: anti-IL-10S protein

<400> SEQUENCE: 6

Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30
```

Pro Gly Gly Ser Leu Arg Leu Ser Cys Ala Ala Ser Gly Phe Ser Phe
        35                  40                  45

Ala Thr Tyr Gly Val His Trp Val Arg Gln Ser Pro Gly Lys Gly Leu
 50                  55                  60

Glu Trp Leu Gly Val Ile Trp Arg Gly Gly Ser Thr Asp Tyr Ser Ala
 65                  70                  75                  80

Ala Phe Met Ser Arg Leu Thr Ile Ser Lys Asp Asn Ser Lys Asn Thr
                 85                  90                  95

Val Tyr Leu Gln Met Asn Ser Leu Arg Ala Glu Asp Thr Ala Val Tyr
                100                 105                 110

Phe Cys Ala Lys Gln Ala Tyr Gly His Tyr Met Asp Tyr Trp Gly Gln
            115                 120                 125

Gly Thr Ser Val Thr Val Ser Ser Gly Gly Gly Gly Ser Gly Gly Gly
        130                 135                 140

Gly Ser Gly Gly Gly Gly Ser Asp Val Val Met Thr Gln Ser Pro Leu
145                 150                 155                 160

Ser Leu Pro Val Thr Leu Gly Gln Pro Ala Ser Ile Ser Cys Arg Ser
                165                 170                 175

Ser Gln Asn Ile Val His Ser Asn Gly Asn Thr Tyr Leu Glu Trp Tyr
            180                 185                 190

Leu Gln Arg Pro Gly Gln Ser Pro Arg Leu Leu Ile Tyr Lys Val Ser
        195                 200                 205

Asn Arg Phe Ser Gly Val Pro Asp Arg Phe Ser Gly Ser Gly Ser Gly
210                 215                 220

Thr Asp Phe Thr Leu Lys Ile Ser Arg Val Glu Ala Glu Asp Val Gly
225                 230                 235                 240

Val Tyr Tyr Cys Phe Gln Gly Ser His Val Pro Trp Thr Phe Gly Gln
                245                 250                 255

Gly Thr Lys Val Glu Ile Lys Tyr Pro Tyr Asp Val Pro Asp Tyr Ala
            260                 265                 270

<210> SEQ ID NO 7
<211> LENGTH: 1113
<212> TYPE: DNA
<213> ORGANISM: artificial
<220> FEATURE:
<223> OTHER INFORMATION: anti-IL-10TM DNA

<400> SEQUENCE: 7
atggactgga tttggcggat cctgttcctc gtgggagccg ccacaggcgc ccattctgaa    60
gtgcagctgg tggaatctgg cggcggactg gtgcagcctg gcggatctct gagactgagc   120
tgtgccgcca gcggcttcag cttt gccaca tacggcgtgc actgggtgcg cagagccct   180
gggaaaggcc tggaatggct gggagtgatc tggcggggag cagcacaga ttacagcgcc   240
gccttcatga gccggctgac catcagcaag acaacagca agaacaccgt gtacctgcag   300
atgaacagct gcgggccga ggataccgcc gtgtacttct gtgccaagca ggcctacggc   360
cactacatgg actattgggg ccagggcacc agcgtgaccg tgtctagcgg aggcggagga   420
tcaggcggcg gaggaagtgg cggaggggga tctgatgtcg tgatgaccca gagccccctg   480
agcctgcctg tgacactggg acagcctgcc agcatcagct gccggtccag ccagaacatc   540
gtgcacagca acggcaacac ctatctggaa tggtatctgc agcggcctgg ccagtccccc   600
agactgctga tctacaaggt gtccaaccgg ttcagcggcg tgcccgacag attttctggc   660
tctggcagcg gcaccgactt caccctgaag atctcccggg tggaagccga ggacgtgggc   720

-continued

```
gtgtactact gttttcaagg cagccacgtg ccctggacct tcggccaggg aacaaaggtg    780
gaaatcaagt accccctacga cgtgcccgat tacgccgccc tgagcaacag catcatgtac    840
ttcagccact tcgtgcccgt gtttctgccc gccaagccta ccacaacccc tgcccctaga    900
cctcctaccc cagcccctac aatcgccagc cagcctctgt ctctgaggcc cgaggcttct    960
agacctgctg ctggcggagc cgtgcacacc agaggactgg acaagcccttt ctgggtgctg  1020 gtggtcgtgg gcggagtgct ggcctgttac agcctgctcg tgacagtggc cttcatcatc  1080
ttttgggtgc gcagcaagcg gagccggccc taa                                1113
```

<210> SEQ ID NO 8
<211> LENGTH: 370
<212> TYPE: PRT
<213> ORGANISM: artificial
<220> FEATURE:
<223> OTHER INFORMATION: anti-IL-10TM protein

<400> SEQUENCE: 8

```
Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ala Thr Tyr Gly Val His Trp Val Arg Gln Ser Pro Gly Lys Gly Leu
    50                  55                  60

Glu Trp Leu Gly Val Ile Trp Arg Gly Gly Ser Thr Asp Tyr Ser Ala
65                  70                  75                  80

Ala Phe Met Ser Arg Leu Thr Ile Ser Lys Asp Asn Ser Lys Asn Thr
                85                  90                  95

Val Tyr Leu Gln Met Asn Ser Leu Arg Ala Glu Asp Thr Ala Val Tyr
            100                 105                 110

Phe Cys Ala Lys Gln Ala Tyr Gly His Tyr Met Asp Tyr Trp Gly Gln
        115                 120                 125

Gly Thr Ser Val Thr Val Ser Ser Gly Gly Gly Ser Gly Gly Gly
    130                 135                 140

Gly Ser Gly Gly Gly Ser Asp Val Val Met Thr Gln Ser Pro Leu
145                 150                 155                 160

Ser Leu Pro Val Thr Leu Gly Gln Pro Ala Ser Ile Ser Cys Arg Ser
                165                 170                 175

Ser Gln Asn Ile Val His Ser Asn Gly Asn Thr Tyr Leu Glu Trp Tyr
            180                 185                 190

Leu Gln Arg Pro Gly Gln Ser Pro Arg Leu Leu Ile Tyr Lys Val Ser
        195                 200                 205

Asn Arg Phe Ser Gly Val Pro Asp Arg Phe Ser Gly Ser Gly Ser Gly
    210                 215                 220

Thr Asp Phe Thr Leu Lys Ile Ser Arg Val Glu Ala Glu Asp Val Gly
225                 230                 235                 240

Val Tyr Tyr Cys Phe Gln Gly Ser His Val Pro Trp Thr Phe Gly Gln
                245                 250                 255

Gly Thr Lys Val Glu Ile Lys Tyr Pro Tyr Asp Val Pro Asp Tyr Ala
            260                 265                 270

Ala Leu Ser Asn Ser Ile Met Tyr Phe Ser His Phe Val Pro Val Phe
        275                 280                 285

Leu Pro Ala Lys Pro Thr Thr Thr Pro Ala Pro Arg Pro Pro Thr Pro
```

```
            290                 295                 300
Ala Pro Thr Ile Ala Ser Gln Pro Leu Ser Leu Arg Pro Glu Ala Ser
305                 310                 315                 320

Arg Pro Ala Ala Gly Gly Ala Val His Thr Arg Gly Leu Asp Lys Pro
            325                 330                 335

Phe Trp Val Leu Val Val Val Gly Gly Val Leu Ala Cys Tyr Ser Leu
                340                 345                 350

Leu Val Thr Val Ala Phe Ile Ile Phe Trp Val Arg Ser Lys Arg Ser
            355                 360                 365

Arg Pro
    370

<210> SEQ ID NO 9
<211> LENGTH: 2484
<212> TYPE: DNA
<213> ORGANISM: artificial
<220> FEATURE:
<223> OTHER INFORMATION: anti-IL-10ER-P2A-single chain IL-12 DNA

<400> SEQUENCE: 9
atggactgga tttggcgcat cctgttcctc gtgggagccg ccacaggcgc ccattctgaa      60
gtgcagctgg tggaatctgg cggcggactg gtgcagcctg gcggatctct gagactgagc     120
tgtgccgcca gcggcttcag cttttgccaca tacggcgtgc actgggtgcg gcagagccct     180
gggaaaggcc tggaatggct gggagtgatc tggcggggag gcagcacaga ttacagcgcc     240
gccttcatga ccggctgac catcagcaag gacaacagca gaacaccgt gtacctgcag      300 atgaacagcc tgcgggccga ggataccgcc gtgtacttct gtgccaagca ggcctacggc     360
cactacatgg actattgggg ccagggcacc agcgtgaccg tgtctagcgg aggcggagga     420
tcaggcggcg gaggaagtgg cggaggggga tctgatgtcg tgatgaccca gagcccctg      480 agcctgcctg tgacactggg acagcctgcc agcatcagct gccggtccag ccagaacatc     540
gtgcacagca acggcaacac ctatctggaa tggtatctgc agcggcctgg ccagtccccc     600
agactgctga tctacaaggt gtccaaccgg ttcagcggcg tgcccgacag atttctggc      660 tctggcagcg gcaccgactt caccctgaag atctcccggg tggaagccga ggacgtgggc     720
gtgtactact gttttcaagg cagccacgtg ccctggacct tcggccaggg aacaaaggtg     780
gaaatcaagt ccccctacga cgtgcccgat acgccaagg acgagctggc aacaaacttc     840
tctctgctga acaagccgg agatgtcgaa gagaatcctg gaccgatgtg tcaccagcag     900
ctggtcatca gctggttcag cctggtgttc tggcctctct ctctggtggc catctgggag     960
ctgaagaaag acgtgtacgt ggtggaactg gactggtatc ccgatgctcc tggcgagatg    1020
gtggtgctga cctgcgatac ccctgaagag acggcatca cctggacact ggatcagtct    1080
agcgaggtgc tcggcagcgg caagaccctg accatccaag tgaaagagtt ggcgacgcc    1140 ggccagtaca cctgtcacaa aggcggagaa gtgctgagcc acagcctgct gctgctccac    1200
aagaaagagg atggcatttg gagcaccgac atcctgaagg accagaaaga gcccaagaac    1260
aagaccttcc tgagatgcga ggccaagaac tacagcggcc ggttcacatg ttggtggctg    1320
accaccatca gcaccgacct gaccttcagc gtgaagtcca gcagaggcag cagtgatcct    1380
cagggcgtta catgtggcgc cgctacactg tctgccgaaa gagtgcgggg cgacaacaaa    1440
gaatacgagt acagcgtgga atgccaagag acagcgcct gtccagccgc cgaagagtct    1500
ctgcctatcg aagtgatggt ggacgccgtg cacaagctga agtacgagaa ctacacctcc    1560
```

-continued

```
agcttttca tccgggacat catcaagccc gatcctccaa agaacctgca gctgaagcct    1620
ctgaagaaca gcagacaggt ggaagtgtcc tgggagtacc ccgacacctg gtctacaccc    1680
cacagctact tcagcctgac cttttgcgtg caagtgcagg caagtccaa gcgcgagaaa    1740 aaggaccggg tgttcaccga caagaccagc gccaccgtga tctgcagaaa gaacgccagc    1800
atcagcgtca gagcccagga ccggtactac agcagctctt ggagcgaatg ggccagcgtg    1860
ccatgttctg gtggcggagg cggaggctct agaaatctgc ctgtggccac tcctgatcct    1920
ggcatgttcc cttgtctgca ccacagccag aacctgctga gagccgtgtc caacatgctg    1980
cagaaggcca gacagaccct ggaattctac ccctgcacca gcgaggaaat cgaccacgag    2040
gacatcacca aggataagac cagcaccgtg aagcctgcc tgcctctgga actgaccaag    2100
aacgagagct gcctgaacag ccgggaaacc agcttcatca ccaacggctc ttgcctggcc    2160
agcagaaaga cctccttcat gatggccctg tgcctgagca gcatctacga ggacctgaag    2220
atgtaccagg tggaattcaa gaccatgaac gccaagctgc tgatggaccc caagcggcag    2280
atcttcctgg accagaatat gctggccgtg atcgacgagc tgatgcaggc cctgaacttc    2340
aacagcgaga cagtgcccca gaagtctagc ctggaagaac ccgacttcta caagaccaag    2400
atcaagctgt gcatcctgct gcacgccttc cggatcagag ccgtgaccat cgacagagtg    2460
atgagctacc tgaacgcctc ctga                                            2484
```

<210> SEQ ID NO 10
<211> LENGTH: 827
<212> TYPE: PRT
<213> ORGANISM: artificial
<220> FEATURE:
<223> OTHER INFORMATION: anti-IL-10ER-P2A-single chain IL-12 protein

<400> SEQUENCE: 10

```
Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ala Thr Tyr Gly Val His Trp Val Arg Gln Ser Pro Gly Lys Gly Leu
    50                  55                  60

Glu Trp Leu Gly Val Ile Trp Arg Gly Gly Ser Thr Asp Tyr Ser Ala
65                  70                  75                  80

Ala Phe Met Ser Arg Leu Thr Ile Ser Lys Asp Asn Ser Lys Asn Thr
                85                  90                  95

Val Tyr Leu Gln Met Asn Ser Leu Arg Ala Glu Asp Thr Ala Val Tyr
            100                 105                 110

Phe Cys Ala Lys Gln Ala Tyr Gly His Tyr Met Asp Tyr Trp Gly Gln
        115                 120                 125

Gly Thr Ser Val Thr Val Ser Ser Gly Gly Gly Ser Gly Gly Gly
    130                 135                 140

Gly Ser Gly Gly Gly Gly Ser Asp Val Val Met Thr Gln Ser Pro Leu
145                 150                 155                 160

Ser Leu Pro Val Thr Leu Gly Gln Pro Ala Ser Ile Ser Cys Arg Ser
                165                 170                 175

Ser Gln Asn Ile Val His Ser Asn Gly Asn Thr Tyr Leu Glu Trp Tyr
            180                 185                 190

Leu Gln Arg Pro Gly Gln Ser Pro Arg Leu Leu Ile Tyr Lys Val Ser
```

```
                195                 200                 205
Asn Arg Phe Ser Gly Val Pro Asp Arg Phe Ser Gly Ser Gly Ser Gly
210                 215                 220

Thr Asp Phe Thr Leu Lys Ile Ser Arg Val Glu Ala Glu Asp Val Gly
225                 230                 235                 240

Val Tyr Tyr Cys Phe Gln Gly Ser His Val Pro Trp Thr Phe Gly Gln
                245                 250                 255

Gly Thr Lys Val Glu Ile Lys Tyr Pro Tyr Asp Val Pro Asp Tyr Ala
            260                 265                 270

Lys Asp Glu Leu Ala Thr Asn Phe Ser Leu Leu Lys Gln Ala Gly Asp
        275                 280                 285

Val Glu Glu Asn Pro Gly Pro Met Cys His Gln Gln Leu Val Ile Ser
290                 295                 300

Trp Phe Ser Leu Val Phe Leu Ala Ser Pro Leu Val Ala Ile Trp Glu
305                 310                 315                 320

Leu Lys Lys Asp Val Tyr Val Val Glu Leu Asp Trp Tyr Pro Asp Ala
                325                 330                 335

Pro Gly Glu Met Val Val Leu Thr Cys Asp Thr Pro Glu Glu Asp Gly
            340                 345                 350

Ile Thr Trp Thr Leu Asp Gln Ser Ser Glu Val Leu Gly Ser Gly Lys
        355                 360                 365

Thr Leu Thr Ile Gln Val Lys Glu Phe Gly Asp Ala Gly Gln Tyr Thr
370                 375                 380

Cys His Lys Gly Gly Glu Val Leu Ser His Ser Leu Leu Leu Leu His
385                 390                 395                 400

Lys Lys Glu Asp Gly Ile Trp Ser Thr Asp Ile Leu Lys Asp Gln Lys
                405                 410                 415

Glu Pro Lys Asn Lys Thr Phe Leu Arg Cys Glu Ala Lys Asn Tyr Ser
            420                 425                 430

Gly Arg Phe Thr Cys Trp Trp Leu Thr Thr Ile Ser Thr Asp Leu Thr
        435                 440                 445

Phe Ser Val Lys Ser Ser Arg Gly Ser Ser Asp Pro Gln Gly Val Thr
450                 455                 460

Cys Gly Ala Ala Thr Leu Ser Ala Glu Arg Val Arg Gly Asp Asn Lys
465                 470                 475                 480

Glu Tyr Glu Tyr Ser Val Glu Cys Gln Glu Asp Ser Ala Cys Pro Ala
                485                 490                 495

Ala Glu Glu Ser Leu Pro Ile Glu Val Met Val Asp Ala Val His Lys
            500                 505                 510

Leu Lys Tyr Glu Asn Tyr Thr Ser Ser Phe Phe Ile Arg Asp Ile Ile
        515                 520                 525

Lys Pro Asp Pro Pro Lys Asn Leu Gln Leu Lys Pro Leu Lys Asn Ser
530                 535                 540

Arg Gln Val Glu Val Ser Trp Glu Tyr Pro Asp Thr Trp Ser Thr Pro
545                 550                 555                 560

His Ser Tyr Phe Ser Leu Thr Phe Cys Val Gln Val Gln Gly Lys Ser
                565                 570                 575

Lys Arg Glu Lys Lys Asp Arg Val Phe Thr Asp Lys Thr Ser Ala Thr
            580                 585                 590

Val Ile Cys Arg Lys Asn Ala Ser Ile Ser Val Arg Ala Gln Asp Arg
        595                 600                 605

Tyr Tyr Ser Ser Ser Trp Ser Glu Trp Ala Ser Val Pro Cys Ser Gly
610                 615                 620
```

Gly Gly Gly Gly Gly Ser Arg Asn Leu Pro Val Ala Thr Pro Asp Pro
625                 630                 635                 640

Gly Met Phe Pro Cys Leu His His Ser Gln Asn Leu Leu Arg Ala Val
            645                 650                 655

Ser Asn Met Leu Gln Lys Ala Arg Gln Thr Leu Glu Phe Tyr Pro Cys
        660                 665                 670

Thr Ser Glu Glu Ile Asp His Glu Asp Ile Thr Lys Asp Lys Thr Ser
    675                 680                 685

Thr Val Glu Ala Cys Leu Pro Leu Glu Leu Thr Lys Asn Glu Ser Cys
690                 695                 700

Leu Asn Ser Arg Glu Thr Ser Phe Ile Thr Asn Gly Ser Cys Leu Ala
705                 710                 715                 720

Ser Arg Lys Thr Ser Phe Met Met Ala Leu Cys Leu Ser Ser Ile Tyr
            725                 730                 735

Glu Asp Leu Lys Met Tyr Gln Val Glu Phe Lys Thr Met Asn Ala Lys
        740                 745                 750

Leu Leu Met Asp Pro Lys Arg Gln Ile Phe Leu Asp Gln Asn Met Leu
    755                 760                 765

Ala Val Ile Asp Glu Leu Met Gln Ala Leu Asn Phe Asn Ser Glu Thr
770                 775                 780

Val Pro Gln Lys Ser Ser Leu Glu Glu Pro Asp Phe Tyr Lys Thr Lys
785                 790                 795                 800

Ile Lys Leu Cys Ile Leu Leu His Ala Phe Arg Ile Arg Ala Val Thr
            805                 810                 815

Ile Asp Arg Val Met Ser Tyr Leu Asn Ala Ser
        820                 825

<210> SEQ ID NO 11
<211> LENGTH: 1578
<212> TYPE: DNA
<213> ORGANISM: artificial
<220> FEATURE:
<223> OTHER INFORMATION: anti-IL-10ER-P2A-IL-15 hyper-agonist DNA

<400> SEQUENCE: 11
atggactgga tttggcgcat cctgttcctc gtgggagccg ccacaggcgc ccattctgaa      60
gtgcagctgg tggaatctgg cggcggactg gtgcagcctg gcggatctct gagactgagc     120
tgtgccgcca gcggcttcag cttttgccaca tacggcgtgc actgggtgcg gcagagccct    180
gggaaaggcc tggaatggct gggagtgatc tggcggggag gcagcacaga ttacagcgcc    240
gccttcatga ccggctgac catcagcaag acaacagca agaacaccgt gtacctgcag      300
atgaacagcc tgcgggccga ggataccgcc gtgtacttct gtgccaagca ggcctacggc    360
cactacatgg actattgggg ccagggcacc agcgtgaccg tgtctagcgg aggcggagga    420
tcaggcggcg gaggaagtgg cggaggggga tctgatgtcg tgatgaccca gagcccctg    480 agcctgcctg tgacactggg acagcctgcc agcatcagct gccggtccag ccagaacatc    540
gtgcacagca acggcaacac ctatctggaa tggtatctgc agcggcctgg ccagtcccc    600 agactgctga tctacaaggt gtccaaccgg ttcagcggcg tgcccgacag attttctggc    660
tctggcagcg gcaccgactt caccctgaag atctcccggg tggaagccga ggacgtgggc    720
gtgtactact gttttcaagg cagccacgtg ccctggacct tcggccaggg aacaaaggtg    780
gaaatcaagt acccctacga cgtgcccgat tacgccaagg acgagctggc aacaaacttc    840
tctctgctga acaagccgg agatgtcgaa gagaatcctg gaccgatgga ctggatttgg    900

```
cgcatcctgt tcctcgtggg agccgccacc ggtgcccatt ctatcacctg tcctccacct    960
atgagcgtgg aacacgccga catctgggtc aagagctaca gcctgtacag cagagagcgg   1020
tacatctgca acagcggctt caagagaaag gccggcacca gcagcctgac cgagtgtgtg   1080
ctgaacaagg ccaccaatgt ggcccactgg accacaccta gcctgaagtg catcagagat   1140
cccgctctgg tgcatcagcg acctgctcca cctggcggag gatctggtgg tggtggaagc   1200
ggaggcggat ctggcggcgg aggttctctg cagaattggg tcaacgtgat ctccgacctg   1260
aagaagatcg aggacctgat ccagagcatg cacatcgacg ccacactgta caccgagagc   1320
gacgtgcacc ctagctgtaa agtgaccgcc atgaagtgct ttctgctgga actgcaagtg   1380
atcagcctgg aaagcggcga cgccagcatc cacgacaccg tggaaaacct gatcatcctg   1440
gccaacgaca gcctgagcag caacggcaat gtgaccgagt ccggctgcaa agagtgcgag   1500
gaactggaag agaagaatat caaagagttc ctgcagagct cgtgcacat cgtgcagatg    1560 ttcatcaaca ccagctga                                                  1578
```

<210> SEQ ID NO 12
<211> LENGTH: 525
<212> TYPE: PRT
<213> ORGANISM: artificial
<220> FEATURE:
<223> OTHER INFORMATION: anti-IL-10ER-P2A-IL-15 hyper-agonist protein

<400> SEQUENCE: 12

```
Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Ser Phe
        35                  40                  45

Ala Thr Tyr Gly Val His Trp Val Arg Gln Ser Pro Gly Lys Gly Leu
    50                  55                  60

Glu Trp Leu Gly Val Ile Trp Arg Gly Gly Ser Thr Asp Tyr Ser Ala
65                  70                  75                  80

Ala Phe Met Ser Arg Leu Thr Ile Ser Lys Asp Asn Ser Lys Asn Thr
                85                  90                  95

Val Tyr Leu Gln Met Asn Ser Leu Arg Ala Glu Asp Thr Ala Val Tyr
            100                 105                 110

Phe Cys Ala Lys Gln Ala Tyr Gly His Tyr Met Asp Tyr Trp Gly Gln
        115                 120                 125

Gly Thr Ser Val Thr Val Ser Ser Gly Gly Gly Ser Gly Gly Gly
    130                 135                 140

Gly Ser Gly Gly Gly Gly Ser Asp Val Val Met Thr Gln Ser Pro Leu
145                 150                 155                 160

Ser Leu Pro Val Thr Leu Gly Gln Pro Ala Ser Ile Ser Cys Arg Ser
                165                 170                 175

Ser Gln Asn Ile Val His Ser Asn Gly Asn Thr Tyr Leu Glu Trp Tyr
            180                 185                 190

Leu Gln Arg Pro Gly Gln Ser Pro Arg Leu Leu Ile Tyr Lys Val Ser
        195                 200                 205

Asn Arg Phe Ser Gly Val Pro Asp Arg Phe Ser Gly Ser Gly Ser Gly
    210                 215                 220

Thr Asp Phe Thr Leu Lys Ile Ser Arg Val Glu Ala Glu Asp Val Gly
225                 230                 235                 240
```

```
Val Tyr Tyr Cys Phe Gln Gly Ser His Val Pro Trp Thr Phe Gly Gln
                245                 250                 255

Gly Thr Lys Val Glu Ile Lys Tyr Pro Tyr Asp Val Pro Asp Tyr Ala
            260                 265                 270

Lys Asp Glu Leu Ala Thr Asn Phe Ser Leu Leu Lys Gln Ala Gly Asp
        275                 280                 285

Val Glu Glu Asn Pro Gly Pro Met Asp Trp Ile Trp Arg Ile Leu Phe
    290                 295                 300

Leu Val Gly Ala Ala Thr Gly Ala His Ser Ile Thr Cys Pro Pro Pro
305                 310                 315                 320

Met Ser Val Glu His Ala Asp Ile Trp Val Lys Ser Tyr Ser Leu Tyr
                325                 330                 335

Ser Arg Glu Arg Tyr Ile Cys Asn Ser Gly Phe Lys Arg Lys Ala Gly
            340                 345                 350

Thr Ser Ser Leu Thr Glu Cys Val Leu Asn Lys Ala Thr Asn Val Ala
        355                 360                 365

His Trp Thr Thr Pro Ser Leu Lys Cys Ile Arg Asp Pro Ala Leu Val
    370                 375                 380

His Gln Arg Pro Ala Pro Pro Gly Gly Ser Gly Gly Gly Ser
385                 390                 395                 400

Gly Gly Gly Ser Gly Gly Gly Ser Leu Gln Asn Trp Val Asn Val
                405                 410                 415

Ile Ser Asp Leu Lys Lys Ile Glu Asp Leu Ile Gln Ser Met His Ile
            420                 425                 430

Asp Ala Thr Leu Tyr Thr Glu Ser Asp Val His Pro Ser Cys Lys Val
        435                 440                 445

Thr Ala Met Lys Cys Phe Leu Leu Glu Leu Gln Val Ile Ser Leu Glu
    450                 455                 460

Ser Gly Asp Ala Ser Ile His Asp Thr Val Glu Asn Leu Ile Ile Leu
465                 470                 475                 480

Ala Asn Asp Ser Leu Ser Ser Asn Gly Asn Val Thr Glu Ser Gly Cys
                485                 490                 495

Lys Glu Cys Glu Glu Leu Glu Glu Lys Asn Ile Lys Glu Phe Leu Gln
            500                 505                 510

Ser Phe Val His Ile Val Gln Met Phe Ile Asn Thr Ser
        515                 520                 525

<210> SEQ ID NO 13
<211> LENGTH: 828
<212> TYPE: DNA
<213> ORGANISM: artificial
<220> FEATURE:
<223> OTHER INFORMATION: anti-IL-6ER DNA

<400> SEQUENCE: 13
atggactgga tttggagaat cctgttcctc gtgggagccg ccacaggcgc tcattctgaa      60
gtgcagctgg tggaatctgg cggcggactt gttcaacctg gcggctctct gagactgagc     120
tgtgccgcca gcggcttcaa cttcaacgac tacttcatga actgggtccg acaggcccct     180
ggcaaaggcc ttgaatgggt tgcccagatg cggaacaaga actaccagta cggcacctac     240
tacgccgaga gcctggaagg cagattcacc atcagccggg acgacagcaa gaacagcctg     300
tacctgcaga tgaactccct gaaaaccgag gacaccgccg tgtactactg cgccagagag     360
agctactacg gcttcaccag ctattggggc cagggcacac tggtcacagt ttctagcgga     420
```

```
ggcggaggat caggtggcgg aggtagtggt ggtggcggaa gcgatatcca gatgacacag        480
agccctagca gcctgtctgc cagcgtggga gacagagtga ccattacctg tcaggccagc        540
caggacatcg gcatcagcct gagttggtat cagcagaagc tggcaaggc ccctaagctg         600 ctgatctaca acgccaacaa cctggccgat ggcgtgccca gcagatttc tggctctggc         660 agcggcaccg acttcacct gaccatatct agcctgcagc ctgaggactt cgccacctac         720
tattgcctgc agcacaacag cgccccttac acctttggac agggcaccaa gctggaaatc        780
aagagatacc cctacgacgt gcccgactac gccaaggatg aactgtga                     828
```

<210> SEQ ID NO 14
<211> LENGTH: 275
<212> TYPE: PRT
<213> ORGANISM: artificial
<220> FEATURE:
<223> OTHER INFORMATION: anti-IL-6ER protein

<400> SEQUENCE: 14

```
Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Phe
        35                  40                  45

Asn Asp Tyr Phe Met Asn Trp Val Arg Gln Ala Pro Gly Lys Gly Leu
    50                  55                  60

Glu Trp Val Ala Gln Met Arg Asn Lys Asn Tyr Gln Tyr Gly Thr Tyr
65                  70                  75                  80

Tyr Ala Glu Ser Leu Glu Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Glu Ser Tyr Tyr Gly Phe Thr Ser Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Gln Ala Ser Gln Asp Ile Gly Ile Ser Leu Ser Trp Tyr Gln Gln
            180                 185                 190

Lys Pro Gly Lys Ala Pro Lys Leu Leu Ile Tyr Asn Ala Asn Asn Leu
        195                 200                 205

Ala Asp Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Leu Gln His Asn Ser Ala Pro Tyr Thr Phe Gly Gln Gly Thr
                245                 250                 255

Lys Leu Glu Ile Lys Arg Tyr Pro Tyr Asp Val Pro Asp Tyr Ala Lys
            260                 265                 270

Asp Glu Leu
        275
```

<210> SEQ ID NO 15
<211> LENGTH: 816
<212> TYPE: DNA
<213> ORGANISM: artificial
<220> FEATURE:
<223> OTHER INFORMATION: anti-IL-6S DNA

<400> SEQUENCE: 15

```
atggactgga tttggagaat cctgttcctc gtgggagccg ccacaggcgc tcattctgaa      60
gtgcagctgg tggaatctgg cggcggactt gttcaacctg gcggctctct gagactgagc     120
tgtgccgcca gcggcttcaa cttcaacgac tacttcatga actgggtccg acaggcccct     180
ggcaaaggcc ttgaatgggt tgcccagatg cggaacaaga actaccagta cggcacctac     240
tacgccgaga gcctggaagg cagattcacc atcagccggg acgacagcaa gaacagcctg     300
tacctgcaga tgaactccct gaaaaccgag gacaccgccg tgtactactg cgccagagag     360
agctactacg gcttcaccag ctattgggc cagggcacac tggtcacagt ttctagcgga     420
ggcggaggat caggtggcgg aggtagtggt ggtggcggaa gcgatatcca gatgacacag     480
agccctagca gcctgtctgc cagcgtggga cacagagtga ccattacctg tcaggccagc     540
caggacatcg gcatcagcct gagttggtat cagcagaagc tggcaaggc ccctaagctg     600
ctgatctaca cgccaacaa cctggccgat ggcgtgccca gcagattttc tggctctggc     660
agcggcaccg acttcaccct gaccatatct agcctgcagc ctgaggactt cgccacctac     720
tattgcctgc agcacaacag cgccccttac acctttggac agggcaccaa gctggaaatc     780
aagagatacc cctacgacgt gcccgattac gcctga                              816
```

<210> SEQ ID NO 16
<211> LENGTH: 271
<212> TYPE: PRT
<213> ORGANISM: artificial
<220> FEATURE:
<223> OTHER INFORMATION: anti-IL-6S protein

<400> SEQUENCE: 16

```
Met Asp Trp Ile Trp Arg Ile Leu Phe Leu Val Gly Ala Ala Thr Gly
1               5                   10                  15

Ala His Ser Glu Val Gln Leu Val Glu Ser Gly Gly Gly Leu Val Gln
            20                  25                  30

Pro Gly Gly Ser Leu Arg Leu Ser Cys Ala Ala Ser Gly Phe Asn Phe
        35                  40                  45

Asn Asp Tyr Phe Met Asn Trp Val Arg Gln Ala Pro Gly Lys Gly Leu
    50                  55                  60

Glu Trp Val Ala Gln Met Arg Asn Lys Asn Tyr Gln Tyr Gly Thr Tyr
65                  70                  75                  80

Tyr Ala Glu Ser Leu Glu Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Glu Ser Tyr Tyr Gly Phe Thr Ser Tyr
        115                 120                 125

Trp Gly Gln Gly Thr Leu Val Thr Val Ser Ser Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175
```

Cys Gln Ala Ser Gln Asp Ile Gly Ile Ser Leu Ser Trp Tyr Gln Gln
            180                 185                 190

Lys Pro Gly Lys Ala Pro Lys Leu Leu Ile Tyr Asn Ala Asn Asn Leu
            195                 200                 205

Ala Asp Gly Val Pro Ser Arg Phe Ser Gly Ser Gly Ser Gly Thr Asp
            210                 215                 220

Phe Thr Leu Thr Ile Ser Ser Leu Gln Pro Glu Asp Phe Ala Thr Tyr
225                 230                 235                 240

Tyr Cys Leu Gln His Asn Ser Ala Pro Tyr Thr Phe Gly Gln Gly Thr
                245                 250                 255

Lys Leu Glu Ile Lys Arg Tyr Pro Tyr Asp Val Pro Asp Tyr Ala
            260                 265                 270

<210> SEQ ID NO 17
<211> LENGTH: 1110
<212> TYPE: DNA
<213> ORGANISM: artificial
<220> FEATURE:
<223> OTHER INFORMATION: anti-IL-6TM DNA

<400> SEQUENCE: 17

```
atggactgga tttggagaat cctgttcctc gtgggagccg ccacaggcgc tcattctgaa      60
gtgcagctgg tggaatctgg cggcggactt gttcaacctg gcggctctct gagactgagc     120
tgtgccgcca gcggcttcaa cttcaacgac tacttcatga actgggtccg acaggcccct     180
ggcaaaggcc ttgaatgggt tgcccagatg cggaacaaga actaccagta cggcacctac     240
tacgccgaga gcctggaagg cagattcacc atcagccggg acgacagcaa gaacagcctg     300
tacctgcaga tgaactccct gaaaaccgag gacaccgccg tgtactactg cgccagagag     360
agctactacg gcttcaccag ctattgggc cagggcacac tggtcacagt ttctagcgga     420
ggcggaggat caggtggcgg aggtagtggt ggtggcggaa gcgatatcca gatgacacag     480
agccctagca gcctgtctgc cagcgtggga cacagagtga ccattacctg tcaggccagc     540
caggacatcg gcatcagcct gagttggtat cagcagaagc ctggcaaggc ccctaagctg     600
ctgatctaca acgccaacaa cctggccgat ggcgtgccca gcagattttc tggctctggc     660
agcggcaccg acttcaccct gaccatatct agcctgcagc ctgaggactt cgccacctac     720
tattgcctgc agcacaacag cgcccctac accttggac agggcaccaa gctggaaatc     780
aagagatacc cctacgacgt gcccgattac gccgccctga gcaacagcat catgtacttc     840
agccacttcg tgcccgtgtt tctgcccgcc aagcctacca aaccctgc ccctagacct     900
cctaccccag cccctacaat cgccagccag cctctgtctc tgaggcccga ggcttctaga     960
cctgctgctg gcggagccgt gcacaccaga ggactggaca gcccttctg ggtgctggtg    1020
gtcgtgggcg gagtgctggc ctgttacagc ctgctcgtga cagtggcctt catcatcttt    1080
tgggtgcgca gcaagcggag ccggccctaa                                    1110
```

<210> SEQ ID NO 18
<211> LENGTH: 369
<212> TYPE: PRT
<213> ORGANISM: artificial
<220> FEATURE:
<223> OTHER INFORMATION: anti-IL-6TM protein

<400> SEQUENCE: 18

Met Asp Trp Ile Trp Arg Ile Leu Phe Leu Val Gly Ala Ala Thr Gly
1               5                   10                  15

-continued

Ala His Ser Glu Val Gln Leu Val Glu Ser Gly Gly Leu Val Gln
        20                  25                  30

Pro Gly Gly Ser Leu Arg Leu Ser Cys Ala Ala Ser Gly Phe Asn Phe
    35                  40                  45

Asn Asp Tyr Phe Met Asn Trp Val Arg Gln Ala Pro Gly Lys Gly Leu
50                  55                  60

Glu Trp Val Ala Gln Met Arg Asn Lys Asn Tyr Gln Tyr Gly Thr Tyr
65                  70                  75                  80

Tyr Ala Glu Ser Leu Glu Gly Arg Phe Thr Ile Ser Arg Asp Asp Ser
                85                  90                  95

Lys Asn Ser Leu Tyr Leu Gln Met Asn Ser Leu Lys Thr Glu Asp Thr
            100                 105                 110

Ala Val Tyr Tyr Cys Ala Arg Glu Ser Tyr Tyr Gly Phe Thr Ser Tyr
        115                 120                 125

Trp Gly Gln Gly Thr Leu Val Thr Val Ser Ser Gly Gly Gly Gly Ser
    130                 135                 140

Gly Gly Gly Gly Ser Gly Gly Gly Ser Asp Ile Gln Met Thr Gln
145                 150                 155                 160

Ser Pro Ser Ser Leu Ser Ala Ser Val Gly Asp Arg Val Thr Ile Thr
                165                 170                 175

Cys Gln Ala Ser Gln Asp Ile Gly Ile Ser Leu Ser Trp Tyr Gln Gln
            180                 185                 190

Lys Pro Gly Lys Ala Pro Lys Leu Leu Ile Tyr Asn Ala Asn Asn Leu
        195                 200                 205

Ala Asp Gly Val Pro Ser Arg Phe Ser Gly Ser Gly Ser Gly Thr Asp
    210                 215                 220

Phe Thr Leu Thr Ile Ser Ser Leu Gln Pro Glu Asp Phe Ala Thr Tyr
225                 230                 235                 240

Tyr Cys Leu Gln His Asn Ser Ala Pro Tyr Thr Phe Gly Gln Gly Thr
                245                 250                 255

Lys Leu Glu Ile Lys Arg Tyr Pro Tyr Asp Val Pro Asp Tyr Ala Ala
            260                 265                 270

Leu Ser Asn Ser Ile Met Tyr Phe Ser His Phe Val Pro Val Phe Leu
        275                 280                 285

Pro Ala Lys Pro Thr Thr Thr Pro Ala Pro Arg Pro Pro Thr Pro Ala
    290                 295                 300

Pro Thr Ile Ala Ser Gln Pro Leu Ser Leu Arg Pro Glu Ala Ser Arg
305                 310                 315                 320

Pro Ala Ala Gly Gly Ala Val His Thr Arg Gly Leu Asp Lys Pro Phe
                325                 330                 335

Trp Val Leu Val Val Val Gly Gly Val Leu Ala Cys Tyr Ser Leu Leu
            340                 345                 350

Val Thr Val Ala Phe Ile Ile Phe Trp Val Arg Ser Lys Arg Ser Arg
        355                 360                 365

Pro

<210> SEQ ID NO 19
<211> LENGTH: 20
<212> TYPE: DNA
<213> ORGANISM: artificial
<220> FEATURE:
<223> OTHER INFORMATION: IL-10 gRNA 1f (gDNA)

<400> SEQUENCE: 19

```
gtgagggcca gcccaggcca                                                20

<210> SEQ ID NO 20
<211> LENGTH: 20
<212> TYPE: DNA
<213> ORGANISM: artificial
<220> FEATURE:
<223> OTHER INFORMATION: IL-10 gRNA 1r (gDNA)

<400> SEQUENCE: 20
tggcctgggc tggccctcac                                                20

<210> SEQ ID NO 21
<211> LENGTH: 20
<212> TYPE: DNA
<213> ORGANISM: artificial
<220> FEATURE:
<223> OTHER INFORMATION: IL-10 gRNA 2f (gDNA)

<400> SEQUENCE: 21
gcgccgtagc ctcagcctga                                                20

<210> SEQ ID NO 22
<211> LENGTH: 20
<212> TYPE: DNA
<213> ORGANISM: artificial
<220> FEATURE:
<223> OTHER INFORMATION: IL-10 gRNA 2r (gDNA)

<400> SEQUENCE: 22
tcaggctgag gctacggcgc                                                20

<210> SEQ ID NO 23
<211> LENGTH: 20
<212> TYPE: DNA
<213> ORGANISM: artificial
<220> FEATURE:
<223> OTHER INFORMATION: IL-10 gRNA 3f (gDNA)

<400> SEQUENCE: 23
ggcgcatgtg aactccctgg                                                20

<210> SEQ ID NO 24
<211> LENGTH: 20
<212> TYPE: DNA
<213> ORGANISM: artificial
<220> FEATURE:
<223> OTHER INFORMATION: IL-10 gRNA 3r (gDNA)

<400> SEQUENCE: 24
ccagggagtt cacatgcgcc                                                20

<210> SEQ ID NO 25
<211> LENGTH: 20
<212> TYPE: DNA
<213> ORGANISM: artificial
<220> FEATURE:
<223> OTHER INFORMATION: IL-10 gRNA 4f (gDNA)

<400> SEQUENCE: 25
tgaaaacaag agcaaggccg                                                20

<210> SEQ ID NO 26
<211> LENGTH: 20
<212> TYPE: DNA
<213> ORGANISM: artificial
```

```
<220> FEATURE:
<223> OTHER INFORMATION: IL-10 gRNA 4r (gDNA)

<400> SEQUENCE: 26
cggccttgct cttgttttca                                               20

<210> SEQ ID NO 27
<211> LENGTH: 19
<212> TYPE: DNA
<213> ORGANISM: artificial
<220> FEATURE:
<223> OTHER INFORMATION: IL-10 shRNA mature antisense

<400> SEQUENCE: 27
ttcgtatctt cattgtcat                                                19

<210> SEQ ID NO 28
<211> LENGTH: 178
<212> TYPE: PRT
<213> ORGANISM: Homo sapiens

<400> SEQUENCE: 28
```

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn

```
<210> SEQ ID NO 29
<211> LENGTH: 212
<212> TYPE: PRT
<213> ORGANISM: Homo sapiens

<400> SEQUENCE: 29
```

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

-continued

```
Ser Ser Glu Arg Ile Asp Lys Gln Ile Arg Tyr Ile Leu Asp Gly Ile
    50              55                  60
Ser Ala Leu Arg Lys Glu Thr Cys Asn Lys Ser Asn Met Cys Glu Ser
65              70                  75              80
Ser Lys Glu Ala Leu Ala Glu Asn Asn Leu Asn Leu Pro Lys Met Ala
                85              90              95
Glu Lys Asp Gly Cys Phe Gln Ser Gly Phe Asn Glu Glu Thr Cys Leu
            100             105             110
Val Lys Ile Ile Thr Gly Leu Leu Glu Phe Glu Val Tyr Leu Glu Tyr
        115             120             125
Leu Gln Asn Arg Phe Glu Ser Ser Glu Glu Gln Ala Arg Ala Val Gln
    130             135             140
Met Ser Thr Lys Val Leu Ile Gln Phe Leu Gln Lys Lys Ala Lys Asn
145             150             155             160
Leu Asp Ala Ile Thr Thr Pro Asp Pro Thr Thr Asn Ala Ser Leu Leu
                165             170             175
Thr Lys Leu Gln Ala Gln Asn Gln Trp Leu Gln Asp Met Thr Thr His
            180             185             190
Leu Ile Leu Arg Ser Phe Lys Glu Phe Leu Gln Ser Ser Leu Arg Ala
        195             200             205
Leu Arg Gln Met
    210
```